United States Patent
Qiu et al.

(10) Patent No.: US 10,702,528 B2
(45) Date of Patent: *Jul. 7, 2020

(54) HEPATITIS B ANTIVIRAL AGENTS

(71) Applicant: Enanta Pharmaceuticals, Inc., Watertown, MA (US)

(72) Inventors: Yao-Ling Qiu, Andover, MA (US); Hui Cao, Belmont, MA (US); Wei Li, Lexington, MA (US); Xiaowen Peng, Sudbury, MA (US); Meizhong Jin, Wellesley, MA (US); Jorden Kass, Arlington, MA (US); Xuri Gao, Newton, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/204,166

(22) Filed: Nov. 29, 2018

(65) Prior Publication Data

US 2019/0216808 A1 Jul. 18, 2019

Related U.S. Application Data

(63) Continuation of application No. 15/209,150, filed on Jul. 13, 2016, now Pat. No. 10,179,131.

(60) Provisional application No. 62/192,012, filed on Jul. 13, 2015.

(51) Int. Cl.

| | | |
|---|---|---|
| *C07D 401/14* | (2006.01) | |
| *A61K 31/506* | (2006.01) | |
| *A61K 45/06* | (2006.01) | |
| *C07D 417/14* | (2006.01) | |
| *C07D 417/12* | (2006.01) | |
| *C07F 9/6558* | (2006.01) | |
| *A61K 31/683* | (2006.01) | |
| *C07D 403/04* | (2006.01) | |
| *C07D 239/20* | (2006.01) | |
| *A61K 31/505* | (2006.01) | |
| *C07D 498/08* | (2006.01) | |
| *A61K 31/5386* | (2006.01) | |
| *A61K 31/5377* | (2006.01) | |
| *C07D 451/06* | (2006.01) | |
| *C07D 487/04* | (2006.01) | |

(52) U.S. Cl.
CPC .......... *A61K 31/506* (2013.01); *A61K 31/505* (2013.01); *A61K 31/5377* (2013.01); *A61K 31/5386* (2013.01); *A61K 31/683* (2013.01); *A61K 45/06* (2013.01); *C07D 239/20* (2013.01); *C07D 403/04* (2013.01); *C07D 417/12* (2013.01); *C07D 417/14* (2013.01); *C07D 451/06* (2013.01); *C07D 487/04* (2013.01); *C07D 498/08* (2013.01); *C07F 9/65583* (2013.01)

(58) Field of Classification Search
CPC .. C07D 401/14; C07D 403/14; C07D 413/14; C07D 417/14; C07D 401/04; C07D 403/04; C07D 413/04; C07D 417/04
See application file for complete search history.

(56) References Cited

U.S. PATENT DOCUMENTS

| | | | |
|---|---|---|---|
| 3,385,756 | A | 5/1968 | Early et al. |
| 3,975,532 | A | 8/1976 | Miller et al. |
| 4,285,946 | A | 8/1981 | Kampe et al. |
| 4,507,481 | A | 3/1985 | Davidson et al. |
| 5,510,387 | A | 4/1996 | Leonidov et al. |
| 5,656,644 | A | 8/1997 | Adams et al. |
| 6,498,165 | B1 | 12/2002 | Armstrong et al. |
| 6,503,913 | B1 | 1/2003 | Goldmann et al. |

(Continued)

FOREIGN PATENT DOCUMENTS

| | | |
|---|---|---|
| CN | 106810548 A | 6/2017 |
| CN | 106928215 A | 7/2017 |

(Continued)

OTHER PUBLICATIONS

CAS Abstract and Indexed Compounds WO 01/68647 (2001) (Year: 2001).*

(Continued)

*Primary Examiner* — Alexander R Pagano
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

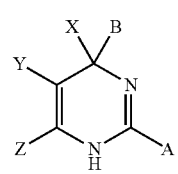

which inhibit the protein(s) encoded by hepatitis B virus (HBV) or interfere with the function of the HBV life cycle of the hepatitis B virus and are also useful as antiviral agents. The present invention further relates to pharmaceutical compositions comprising the aforementioned compounds for administration to a subject suffering from HBV infection. The invention also relates to methods of treating an HBV infection in a subject by administering a pharmaceutical composition comprising the compounds of the present invention.

14 Claims, No Drawings

(56) References Cited

U.S. PATENT DOCUMENTS

| | | |
|---|---|---|
| 6,525,069 B1 | 2/2003 | Ko et al. |
| 6,667,342 B1 | 12/2003 | Clarke et al. |
| 7,232,825 B2 | 6/2007 | Chen et al. |
| 7,312,214 B2 | 12/2007 | Qiao et al. |
| 7,411,003 B1* | 8/2008 | Liu ................ C07C 403/02 514/690 |
| 7,615,569 B2 | 11/2009 | Fulp et al. |
| 7,741,494 B2 | 6/2010 | Bressi et al. |
| 8,202,876 B2 | 6/2012 | Albaugh et al. |
| 8,420,823 B2 | 4/2013 | Sato et al. |
| 9,447,086 B2 | 9/2016 | Liu et al. |
| 9,498,479 B2 | 11/2016 | Zhang et al. |
| 9,573,941 B2 | 2/2017 | Liu et al. |
| 9,617,252 B2 | 4/2017 | Liu |
| 9,938,301 B2 | 4/2018 | He et al. |
| 10,179,131 B2* | 1/2019 | Qiu ................ A61K 31/505 |
| 10,189,846 B2 | 1/2019 | Qiu et al. |
| 10,253,030 B2 | 4/2019 | He et al. |
| 10,428,070 B2* | 10/2019 | Qiu ................ C07D 471/04 |
| 2002/0068838 A1 | 6/2002 | Demassey et al. |
| 2003/0232842 A1 | 12/2003 | Goldmann et al. |
| 2004/0209930 A1 | 10/2004 | Carboni et al. |
| 2005/0203119 A1 | 9/2005 | Ono et al. |
| 2007/0219239 A1 | 9/2007 | Mjalli et al. |
| 2007/0225373 A1 | 9/2007 | Chen et al. |
| 2008/0120759 A1 | 5/2008 | Tolton et al. |
| 2009/0023740 A1 | 1/2009 | Fulp et al. |
| 2011/0009622 A1 | 1/2011 | Jitsuoka et al. |
| 2011/0165118 A1 | 7/2011 | Chan et al. |
| 2011/0281950 A1 | 11/2011 | Baiocchi et al. |
| 2012/0009142 A1 | 1/2012 | Karp et al. |
| 2013/0251673 A1 | 9/2013 | Hartman et al. |
| 2013/0267517 A1 | 10/2013 | Guo et al. |
| 2014/0343032 A1 | 11/2014 | Zhu et al. |
| 2015/0005295 A1 | 1/2015 | Haché et al. |
| 2015/0119362 A1 | 4/2015 | Gurney et al. |
| 2015/0152073 A1 | 6/2015 | Hartman et al. |
| 2015/0152096 A1 | 6/2015 | Zhang et al. |
| 2015/0197493 A1 | 7/2015 | Hartman et al. |
| 2015/0252057 A1 | 9/2015 | Zhu et al. |
| 2015/0274653 A1 | 10/2015 | Verschueren et al. |
| 2016/0185777 A1 | 6/2016 | Hartman et al. |
| 2016/0206616 A1 | 7/2016 | Zhang et al. |
| 2016/0237078 A9 | 8/2016 | Guo et al. |
| 2016/0264562 A1 | 9/2016 | Liu et al. |
| 2016/0264563 A1 | 9/2016 | Ren et al. |
| 2016/0289212 A1 | 10/2016 | Gao et al. |
| 2016/0296515 A1 | 10/2016 | Han et al. |
| 2016/0332996 A1 | 11/2016 | Gao et al. |
| 2016/0347746 A1 | 12/2016 | Zhang |
| 2017/0014408 A1* | 1/2017 | Qiu ................ A61K 45/06 |
| 2017/0022150 A1 | 1/2017 | Gao et al. |
| 2017/0197986 A1 | 7/2017 | He et al. |
| 2017/0217974 A1 | 8/2017 | Gao et al. |
| 2017/0253609 A1 | 9/2017 | Gao et al. |
| 2017/0355701 A1 | 12/2017 | Qiu et al. |
| 2018/0312512 A1 | 11/2018 | He et al. |
| 2019/0084994 A1 | 3/2019 | Qiu et al. |
| 2019/0119288 A1* | 4/2019 | Qiu ................ C07D 487/04 |
| 2019/0177316 A1* | 6/2019 | Qiu ................ C07D 471/04 |
| 2019/0177320 A1 | 6/2019 | Qiu et al. |

FOREIGN PATENT DOCUMENTS

| | | | |
|---|---|---|---|
| CN | 106928245 A | 7/2017 | |
| WO | 8702367 A2 | 4/1987 | |
| WO | 9504046 A1 | 2/1995 | |
| WO | 0168641 A1 | 9/2001 | |
| WO | 0168647 A1 | 9/2001 | |
| WO | WO-0168647 A1 * | 9/2001 | ........... C07D 401/14 |
| WO | 2006033995 A2 | 3/2006 | |
| WO | 2008120759 A1 | 10/2008 | |
| WO | WO-2009158473 A1 * | 12/2009 | ........... C07D 401/04 |
| WO | 2013006394 A1 | 1/2013 | |
| WO | 2013096744 A1 | 6/2013 | |
| WO | 2013130703 A2 | 9/2013 | |
| WO | 2013144129 A1 | 10/2013 | |
| WO | 2013181584 A2 | 12/2013 | |
| WO | 2014106019 A2 | 7/2014 | |
| WO | 2014184350 A1 | 11/2014 | |
| WO | 2014184365 A1 | 11/2014 | |
| WO | 2015074546 A1 | 5/2015 | |
| WO | 2015113990 A1 | 8/2015 | |
| WO | 2015173164 A1 | 11/2015 | |
| WO | 2015180631 A1 | 12/2015 | |
| WO | 2016016370 A1 | 2/2016 | |
| WO | 2016071215 A1 | 5/2016 | |
| WO | 2016128335 A1 | 8/2016 | |
| WO | 2017013046 A1 | 1/2017 | |
| WO | 2017017042 A1 | 2/2017 | |
| WO | 2017017043 A1 | 2/2017 | |
| WO | 2017140821 A1 | 8/2017 | |
| WO | 2017205115 A1 | 11/2017 | |
| WO | 2017216685 A1 | 12/2017 | |
| WO | 2017216686 A1 | 12/2017 | |
| WO | 2018019297 A1 | 2/2018 | |
| WO | 2018022282 A1 | 2/2018 | |
| WO | 2018047109 A1 | 3/2018 | |
| WO | 2018073753 A1 | 4/2018 | |
| WO | 2018085619 A1 | 5/2018 | |
| WO | 2018196805 A1 | 11/2018 | |

OTHER PUBLICATIONS

Z. Qiu et al., Journal of Medicinal Chemistry (2016) (Year: 2016).*

W. El-Hamouly et al., 2 International Journal of Pharmaceutical Sciences and Research, 1054-1062 (2011) (Year: 2011).*

U.S. Appl. No. 16/194,608, filed Nov. 19, 2018.

U.S. Appl. No. 16/210,472, filed Dec. 5, 2018.

Janetka, J. W. et al., "Discovery of a novel class of 2-ureido thiophene carboxamide checkpoint kinase inhibitors", Bioorganic & Medicinal Chemistry Letters, 18, 2008, 4242-4248.

Yang, et al., "Enzyme-mediated hydrolytic activation of prodrugs", Acta Pharmaceutical Sinica B., vol. 1(3), Sep. 9, 2011, 143-159.

Li, X. et al., 8 ACS Medicinal Chemistry Letters, 8, 2017, 969-974.

Noguchi, Chiemi et al., "G to A Hypermutation of Hepatitis B Virus", Hepatology, vol. 41, No. 3, 2005, 2005, 626-633.

Chemical Abstract Service STN Database Registry No. 1578268-77-5 [online][Entered STN: Apr. 1, 2014].

Chemical Abstracts Registry No. 1026741-09-2, indexed in the Registry file on Jun. 9, 2008.

Chemical Abstracts Registry No. 115280-56-3, indexed in the Registry file on STN CAS Online Jul. 16, 1988.

Chemical Abstracts Registry No. 1269203-67-9, indexed in the Registry file on STN CAS Online Mar. 21, 2011.

Chemical Abstracts Registry No. 1350251-34-1, indexed in the Registry file on STN CAS Online Dec. 7, 2011.

Chemical Abstracts Registry No. 397288-41-1, indexed in the Registry file on Mar. 1 (Year: 2002).

Chemical Abstracts Registry No. 792901-47-4, indexed in the Registry file on STN CAS Online Dec. 6, 2004.

Chemical Abstracts Registry No. 92555-24-3, indexed in the Registry file on Dec. 17, 1984.

Chemical Abstracts Registry No. 950067-32-0, indexed in the Registry file on Oct. 10, 2007.

PubChem CID 57036978, National Center for Biotechnology Information. PubChem Compound Database; CID=57036978, https://pubchem.ncbi.nlm.nih.gov/compound/57036978 (accessed May 19, 2017), create date Jun. 13, 2012.

PubChem CID 69095846 {National Center for Biotechnology Information. PubChem Compound Database; CID=69095846, https://pubchem.ncbi.nlm.nih.gov/compound/69095846 (accessed May 23, 2017), create date Nov. 30, 2012.

PubChem CI D 10194182, National Center for Biotechnology Information. PubChem Compound Database; CI 0=10194182, https://pubchem.ncbi.nlm.nih.gov/ compound/10194182 (accessed May 19, 2017), create date Oct. 25, 2006.

(56) References Cited

OTHER PUBLICATIONS

Pubchem—'428' Create Date: Sep. 11, 2005 (Sep. 11, 2005) Date Accessed: Jun. 17, 2016.
PUBCHEM—CID 23201920, Create Date: Dec. 5, 2007, p. 3.
PUBCHEM—CID 63186259, Create Date: Oct. 22, 2012 (Oct. 22, 2012) p. 3.
PUBCHEM—SID 15224030 Deposit Date: Oct. 25, 2006.
Pubchem—57224610 ('610') Create Date: Jun. 14, 2012 (Jun. 14, 2012) Date Accessed: Jun. 17, 2016.
Chemical Abstract Service STN CAplus [online database], Accession No. 2003:1014580. (Year: 2003).
Ballatore, et al., "Carboxylic Acid (Bio)Isosteres in Drug Design", ChemMedChem., vol. 8, No. 3, 2013, 385-395.
Clark, et al., "5-(aLKYLSULFONYL)Salicylanilides as Potential Dental Antiplaque Agents", Journal of Medicinal Chemistry, 29(1), 1986, 25-29.

* cited by examiner

HEPATITIS B ANTIVIRAL AGENTS

RELATED APPLICATIONS

This application is a continuation of U.S. application Ser. No. 15/209,150, filed on Jul. 13, 2016, which claims the benefit of U.S. Provisional Application No. 62/192,012, filed on Jul. 13, 2015. The entire teachings of the above applications are incorporated herein by reference.

TECHNICAL FIELD

The present invention relates generally to novel antiviral agents. Specifically, the present invention relates to compounds which can inhibit the protein(s) encoded by hepatitis B virus (HBV) or interfere with the function of the HBV life cycle, compositions comprising such compounds, methods for inhibiting HBV viral replication, methods for treating or preventing HBV infection, and processes for making the compounds.

BACKGROUND OF THE INVENTION

HBV infection remains a major public health problem, affecting approximately 2 billion people worldwide. Among them, 350 million people worldwide and 1.4 million in the US develop a chronic infection, which can lead to chronic persistent hepatitis, liver cirrhosis, and hepatocellular carcinoma (HCC). Every year 500,000 to 1 million people die from the end stage of liver diseases caused by HBV infection.

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent HCC. Current therapy goals for HBV-infected patients are directed to reducing serum HBV DNA to low or undetectable levels, and to ultimately reducing or preventing the development of cirrhosis and HCC.

The HBV is an enveloped, partially double-stranded DNA (dsDNA) virus of the hepadnavirus family (Hepadnaviridae). HBV capsid protein (CP) plays essential roles in HBV replication. The predominant biological function of capsid protein is to act as a structural protein to encapsidate pre-genomic RNA and form immature capsid particles, which spontaneously self-assemble from many copies of core dimers in the cytoplasm. Capsid protein also regulates viral DNA synthesis through different phosphorylation status of its C-terminal phosphorylation sites. Also, capsid protein might facilitate the nuclear translocation of viral relaxed circular genome by means of the nuclear localization signals located in the Arginine-rich domain of the C-terminal region of capsid protein. In the nucleus, as a component of viral cccDNA minichromosome, capsid protein could play a structural and regulatory role in the functionality of cccDNA minichromosomes. Capsid protein also interacts with viral large envelope protein in endoplasmic reticulum (ER) and triggers the release of intact viral particles from hepatocytes.

Capsid related anti-HBV inhibitors have been reported. For example, phenylpropen-amide derivatives, including compounds named AT-61 and AT-130 (Feld J. et al. Antiviral Res. 2007, 76, 168), and a class of thiazolidin-4-ones from Valeant (WO 2006/033995), have been shown to inhibit pregenomic RNA (pgRNA) packaging. Heteroaryldihydropyrimi-dines or HAPs were discovered in a tissue culture-based screening (Weber et al., Antiviral Res. 2002, 54, 69). These HAP analogs act as synthetic allosteric activators and are able to induce aberrant capsid formation that leads to degradation of the core protein. A subclass of sulphamoyl-arylamides also shows activity against HBV (WO 2013/006394, WO 2013/096744, and WO 2014184365). It was also shown that the small molecule bis-ANS acts as a molecular 'wedge' and interferes with normal capsid-protein geometry and capsid formation (Zlotnick A. et al. J. Virol. 2002, 4848).

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly HBV) infection in a subject in need of such therapy with said compounds. Compounds of the present invention inhibit the protein(s) encoded by hepatitis B virus (HBV) or interfere with the life cycle of HBV and are also useful as antiviral agents. In addition, the present invention includes the process for the preparation of the said compounds.

In its principal aspect, the present invention provides a compound of Formula (I):

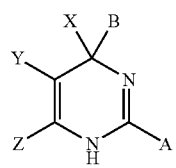

(I)

or a pharmaceutically acceptable salt thereof, wherein:

A is selected from the group consisting of optionally substituted aryl, optionally substituted heteroaryl, optionally substituted —$C_3$-$C_8$ cycloalkyl, optionally substituted 3- to 8-membered heterocyclic, —C(O)$R_1$, —$CO_2R_1$, —C(O)N$R_1R_2$, —O$R_1$, and —N$R_1R_2$; preferably A is optionally substituted heteroaryl, such as optionally substituted azolyl or optionally substituted pyridyl;

B is selected from the group consisting of hydrogen, CN, optionally substituted —$C_1$-$C_6$ alkyl, and optionally substituted —$C_3$-$C_6$ cycloalkyl; preferably B is hydrogen or methyl;

X is selected from the group consisting of optionally substituted —$C_3$-$C_8$ cycloalkyl, optionally substituted 3- to 8-membered heterocyclic, optionally substituted aryl, and optionally substituted heteroaryl; preferably X is optionally substituted phenyl;

Y is selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl, optionally substituted heteroaryl, —CN, —C(O)$R_1$, —$CO_2R_1$, —C(O)$NR_1R_2$, —C(O)N($R_1$)S(O)$_2R_3$, —S(O)$_2R_3$, —S(O)$_2NR_1R_2$, —$NR_1R_2$, —N($R_1$)C(O)$R_3$, —N($R_1$)C(O)$NR_1R_2$, —N($R_1$)C(O)$OR_3$ and —P(O)(O$R_3$)$_2$; preferably Y is optionally substituted azolyl or optionally substituted pyridyl;

Preferably, when Y is —$CO_2R_1$ or —C(O)$NR_1R_2$, at least one of A and X is not optionally substituted aryl or optionally substituted heteroaryl.

Z is selected from the group consisting of hydrogen, optionally substituted —$C_1$-$C_{12}$ alkyl, optionally substituted —$C_2$-$C_{12}$ alkenyl, optionally substituted —$C_2$-$C_{12}$ alkynyl, optionally substituted —$C_3$-$C_8$ cycloalkyl, optionally substituted 3- to 8-membered heterocyclic, optionally substituted aryl and optionally substituted heteroaryl, —C(O)$NR_1R_2$, and —C(O)$OR_1$; preferably Z is hydrogen or optionally substituted methyl;

$R_1$ and $R_2$ at each occurrence are independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl;

Alternatively, $R_1$ and $R_2$ are taken together with the nitrogen atom to which they are attached to form an optionally substituted 3- to 10-membered heterocyclic; and $R_3$ at each occurrence is selected from the group consisting of optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl;

Each preferred group stated above can be taken in combination with one, any or all other preferred groups.

DETAILED DESCRIPTION OF THE INVENTION

In one embodiment of the present invention is a compound of Formula (I) as described above, or a pharmaceutically acceptable salt thereof.

In another embodiment of the present invention is a compound of Formula (I) or a pharmaceutically acceptable salt thereof, is represented by its 4α-enantiomer (I-a) or its 4β-enantiomer (I-b):

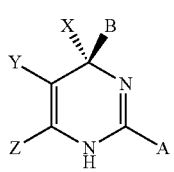
(I-a)

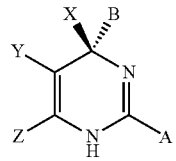
(I-b)

In one particular embodiment, compounds of the present invention preferably have the 4α-configuration as shown in Formula (I-a).

In certain embodiments, the present invention relates to compounds of Formula (I), and pharmaceutically acceptable salts thereof, wherein A is optionally substituted aryl or optionally substituted heteroaryl. In certain embodiments, the present invention relates to compounds of Formula (I), and pharmaceutically acceptable salts thereof, wherein A is an optionally substituted azolyl or optionally substituted pyridyl. In certain embodiments, A is thiazolyl, such as thiazol-2-yl.

In certain embodiments, the present invention relates to compounds of Formula (I), and pharmaceutically acceptable salts thereof, wherein A is optionally substituted —$C_3$-$C_8$ cycloalkyl, optionally substituted 3- to 8-membered heterocyclic, —C(O)$R_1$, —$CO_2R_1$, —C(O)$NR_1R_2$, —$OR_1$, or —$NR_1R_2$, where $R_1$ and $R_2$ are as previously defined.

In certain embodiments, the present invention relates to compounds of Formula (I), and pharmaceutically acceptable salts thereof, wherein B is hydrogen or methyl, preferably hydrogen.

In certain embodiments, the present invention relates to compounds of Formula (I), and pharmaceutically acceptable salts thereof, wherein Z is hydrogen, optionally substituted —$C_1$-$C_4$ alkyl, or optionally substituted —$C_3$-$C_8$ cycloalkyl. In certain embodiments, the present invention relates to compounds of Formula (I), and pharmaceutically acceptable salts thereof, wherein Z is preferably hydrogen or an optionally substituted methyl. In certain embodiments, the present invention relates to compounds of Formula (I), and pharmaceutically acceptable salts thereof, wherein Z is —C(O)$NR_1R_2$ or —C(O)$OR_1$. In certain embodiments, the present invention relates to compounds of Formula (I), and pharmaceutically acceptable salts thereof, wherein Z is methyl or methyl substituted with halo, —CN, $N_3$, —$OR_1$, —$NR_1R_2$, —C(O)$NR_1R_2$, or —C(O)$OR_1$; wherein $R_1$ and $R_2$ are as previously defined. In one embodiment, Z is methyl or trifluoromethyl.

In certain embodiments, Z is $R_1R_2$N—$CH_2$—, where $R_1$, $R_2$ and the nitrogen atom to which they are attached form an optionally substituted heterocycloalkyl group. In certain embodiments, the heterocycloalkyl group is substituted with one or more groups selected from carboxy; alkoxycarbonyl; halo, for example, fluoro; azolyl, for example tetrazolyl; cyano or R—$SO_2$NH—C(O)—, where R is alkyl, preferably $C_1$-$C_6$-alkyl. In certain embodiments, Z is a group selected from those set forth below:

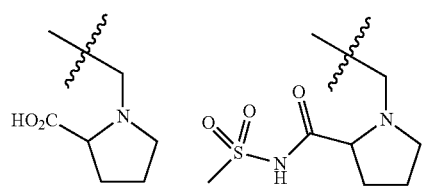

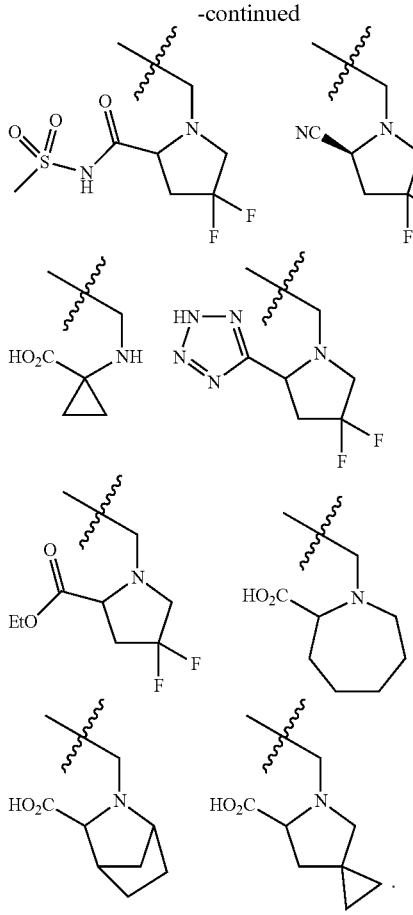

In certain embodiments of the compounds of the invention X is optionally substituted phenyl, for example, phenyl substituted with one or more halogen atoms preferably independently selected from chloro and fluoro. In one embodiment X is 2-chloro-4-fluorophenyl. In certain embodiments, the present invention relates to compounds of Formula (I), and pharmaceutically acceptable salts thereof, wherein X is optionally substituted heteroaryl.

In certain embodiments, the present invention relates to compounds of Formula (I), and pharmaceutically acceptable salts thereof, wherein Y is selected from the group consisting of optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl, optionally substituted heteroaryl. In certain embodiments, the present invention relates to compounds of Formula (I), and pharmaceutically acceptable salts thereof, wherein Y is selected from the group consisting of —CN, —C(O)$R_1$, —C(O)N($R_1$)S(O)$_2R_3$, —S(O)$_2R_3$, —S(O)$_2$N$R_1R_2$, —N$R_1R_2$, —N($R_1$)C(O)$R_3$, —N($R_1$)C(O)N$R_1R_2$, —N($R_1$)C(O)O$R_3$, —P(O)(O$R_3$)$_2$; wherein $R_1$, $R_2$, and $R_3$ are as previously defined.

In certain embodiments of the compounds of the invention, Y is optionally substituted phenyl. In certain embodiments of the compounds of the invention, Y is optionally substituted heteroaryl. In certain embodiments, the present invention relates to compounds of Formula (I), and pharmaceutically acceptable salts thereof, wherein Y is optionally substituted azolyl or optionally substituted pyridyl.

In one embodiment of the compounds of the invention, Y is —CO$_2$H, —CO$_2$Et, —C(O)NHMe, —S(O)$_2$Me, —CH$_2$NMe$_2$, —C(O)NHSO$_2$Me, —C(O)N(Me)SO$_2$Me, —P(O)(O$R_3$)$_2$, or selected from the groups set forth below:

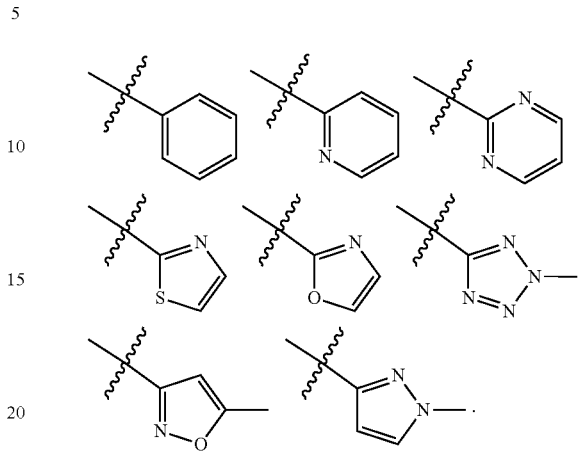

In certain embodiments, the present invention relates to compounds of Formula (I), and pharmaceutically acceptable salts thereof, wherein X is optionally substituted phenyl; Y is an optionally substituted heteroaryl. In certain embodiments, the present invention relates to compounds of Formula (I), and pharmaceutically acceptable salts thereof, wherein X is optionally substituted phenyl; Y is an optionally substituted azolyl or optionally substituted pyridyl.

In certain embodiments, the present invention relates to compounds of Formula (I), and pharmaceutically acceptable salts thereof, wherein X is optionally substituted monocyclic heteroaryl; Y is an optionally substituted azolyl or optionally substituted pyridyl.

In certain embodiments, the present invention relates to compounds of Formula (I), and pharmaceutically acceptable salts thereof, wherein X is optionally substituted —$C_3$-$C_8$ cycloalkyl; Y is an optionally substituted azolyl or optionally substituted pyridyl.

In certain embodiments, the present invention relates to compounds of Formula (I), and pharmaceutically acceptable salts thereof, wherein X is optionally substituted 3- to 8-membered heterocyclic; Y is an optionally substituted azolyl or optionally substituted pyridyl.

In another particular embodiment, the present invention relates to compounds of Formula (I), or a pharmaceutically acceptable salt thereof, wherein A and X are each independently an aryl or heteroaryl group derived from one of the following by removal of one hydrogen atom:

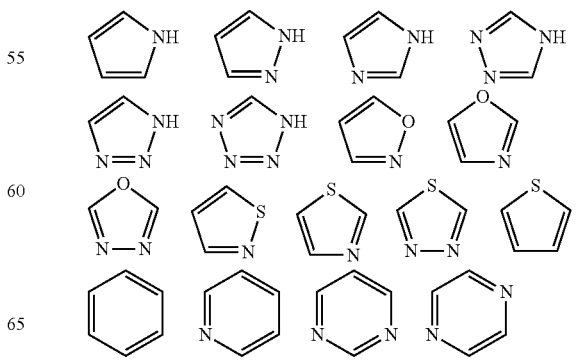

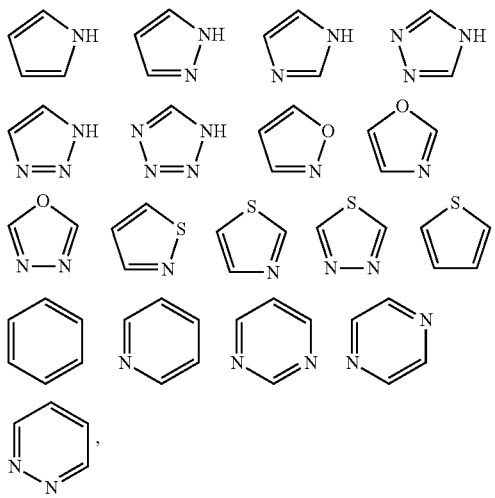

wherein each of the above shown aryl groups is optionally substituted when possible and may be connected to the dihydropypyrimidine core through a carbon atom.

In another particular embodiment, the present invention relates to compounds of Formula (I), or a pharmaceutically acceptable salt thereof, wherein at least one of A and X is an aryl or heteroaryl group derived from one of the following by removal of one hydrogen atom:

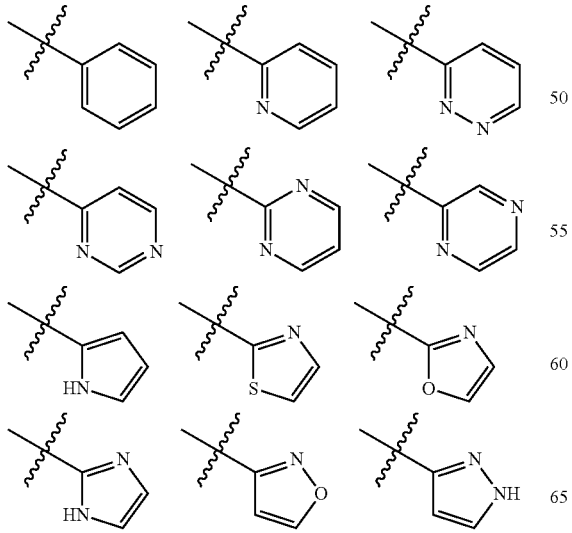

wherein each of the above shown aryl groups is optionally substituted when possible and may be connected to the dihydropypyrimidine core through a carbon atom.

In certain embodiments, A and X are each independently selected from the groups set forth below:

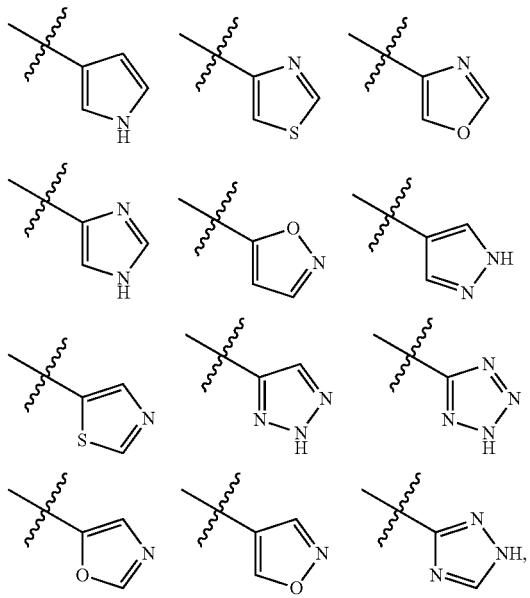

wherein each of the above shown groups is optionally substituted when possible. The preferred substitution groups are optionally substituted methyl, halo, CN, —OR$_1$, —NR$_1$R$_2$; wherein R$_1$ and R$_2$ are as previously defined.

In certain embodiments, at least one of A and X is selected from the groups set forth below:

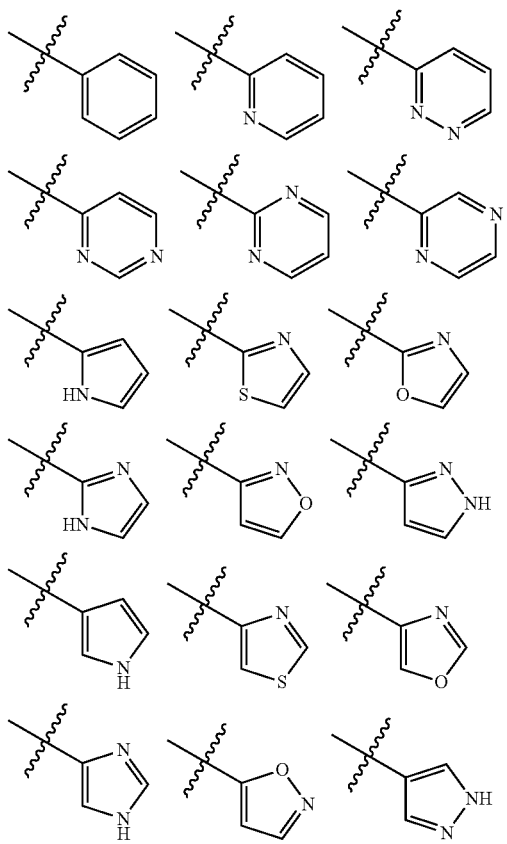

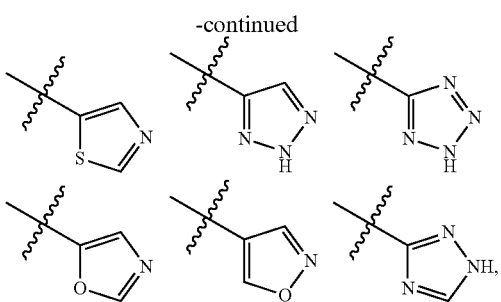

wherein each of the above shown groups is optionally substituted when possible. The preferred substitution groups are optionally substituted methyl, halo, CN, —OR$_1$, —NR$_1$R$_2$; wherein R$_1$ and R$_2$ are as previously defined.

In certain embodiments, the present invention relates to compounds of Formula (I), or a pharmaceutically acceptable salt thereof, A is selected from the group consisting of optionally substituted —C$_3$-C$_5$ cycloalkyl and optionally substituted 3- to 8-membered heterocyclic.

In certain embodiments, the present invention relates to compounds of Formula (I), or a pharmaceutically acceptable salt thereof, X is selected from the group consisting of optionally substituted —C$_3$-C$_5$ cycloalkyl and optionally substituted 3- to 8-membered heterocyclic.

In certain embodiments, the present invention relates to compounds of Formula (I), and pharmaceutically acceptable salts thereof, wherein Y is —CO$_2$R$_1$ or —C(O)NR$_1$R$_2$; A is selected from the group consisting of —C(O)R$_1$, —CO$_2$R$_1$, —C(O)NR$_1$R$_2$, —OR$_1$, —NR$_1$R$_2$, optionally substituted —C$_3$-C$_5$ cycloalkyl, and optionally substituted 3- to 8-membered heterocyclic; R$_1$ and R$_2$ are as previously defined.

In certain embodiments, the present invention relates to compounds of Formula (I), and pharmaceutically acceptable salts thereof, wherein Y is —CO$_2$R$_1$ or —C(O)NR$_1$R$_2$; X is an optionally substituted —C$_3$-C$_8$ cycloalkyl or optionally substituted 3- to 8-membered heterocyclic.

In another embodiment, the compound of Formula (I) is represented by Formula (IIa) (IIb), or (IIc), or a pharmaceutically acceptable salt thereof:

IIa
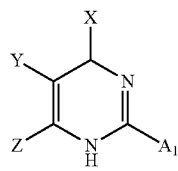

IIb
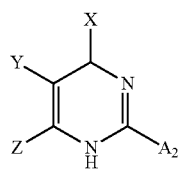

IIc
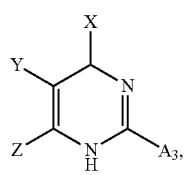

wherein A$_1$ is a 5-membered heteroaryl containing 1 to 4 heteroatoms selected from O, N, and S; preferably A$_1$ is an optionally substituted azole group including but not limited to pyrrolyl, pyrazolyl, imidazolyl, thiazolyl, oxazolyl, isoxazolyl, thiadiazolyl, oxadiazolyl or thiophenyl; each optionally substituted; A$_2$ is an optionally substituted phenyl or 6-membered heteroaryl group including but not limited to pyridinyl, pyrazinyl, or pyrimidinyl; each optionally substituted; A$_3$ is an optionally substituted —C$_3$-C$_8$ cycloalkyl, optionally substituted 3- to 8-membered heterocyclic, —CN, —C(O)R$_1$, —CO$_2$R$_1$, —C(O)NR$_1$R$_2$, —OR$_1$, or —NR$_1$R$_2$; and X, Y, and Z are as previously defined.

In a particular embodiment, the compound of Formula (I) is represented by Formula (IIa-a), (IIb-a), or (IIc-a), or a pharmaceutically acceptable salt thereof:

IIa-a
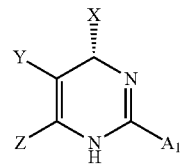

IIb-a
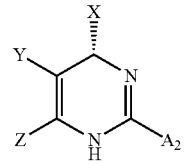

IIc-a
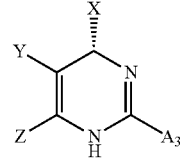

wherein A$_1$, A$_2$, A$_3$, and X, Y, and Z are as previously defined.

In another embodiment, the compound of Formula (I) is represented by Formula (IIa-1), (IIb-1), or (IIc-1), or a pharmaceutically acceptable salt thereof:

IIa-1
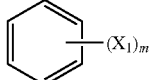
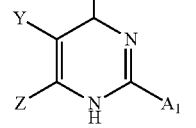

IIb-1
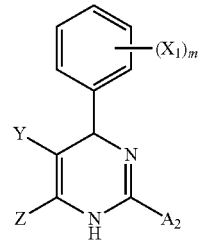

-continued

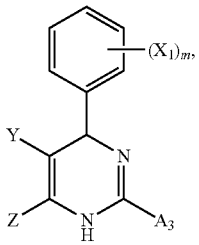

IIc-1

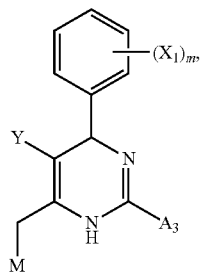

IIc-2 wherein each $X_1$ is independently halo, —CN, —OR$_1$, —NR$_1$R$_2$, or optionally substituted methyl; m is 0, 1, 2, 3, 4 or 5; A$_1$, A$_2$, A$_3$, Y, Z, R$_1$, and R$_2$ are all as previously defined.

In certain embodiments, the compound of Formula (I) is represented by Formula (IIa-1), (IIb-1), or (IIc-1), or a pharmaceutically acceptable salt thereof, wherein m is 0. In another embodiment, each $X_1$ is halo, preferably chloro or fluoro. In certain embodiments, the compound of Formula (I) is represented by Formula (IIa-1), (IIb-1), or (IIc-1), or a pharmaceutically acceptable salt thereof, wherein Y is optionally substituted azolyl. In certain embodiments, the compound of Formula (I) is represented by Formula (IIa-1), (IIb-1), or (IIc-1), or a pharmaceutically acceptable salt thereof, wherein Z is hydrogen or optionally substituted —C$_1$-C$_4$ alkyl. In certain embodiments, the compound of Formula (I) is represented by Formula (IIa-1), (IIb-1), or (IIc-1), or a pharmaceutically acceptable salt thereof, wherein Z is optionally substituted methyl. In certain embodiments, the compound of Formula (I) is represented by Formula (IIa-1), (IIb-1), or (IIc-1), or a pharmaceutically acceptable salt thereof, wherein Z is hydrogen.

In another embodiment, the compound of Formula (I) is represented by Formula (IIa-2), (IIb-2), or (IIc-2), or a pharmaceutically acceptable salt thereof:

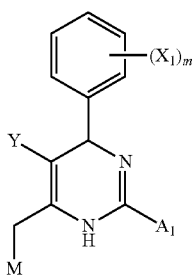

IIa-2

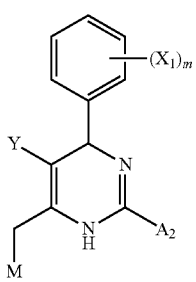

IIb-2 wherein M is hydrogen, —CN, —NO$_2$, —OR$_1$, protected hydroxy, —CR'R$_{1a}$R$_{2a}$, —NR$_1$R$_2$, protected amino, —CO$_2$R$_1$, or —C(O)NR$_1$R$_2$; wherein R' is selected from the group consisting of hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, —CN, —OR$_1$, and —NR$_1$R$_2$; R$_{1a}$ and R$_{2a}$ at each occurrence are independently selected from the group consisting of hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocyclic, optionally substituted aryl and optionally substituted heteroaryl; alternatively, R$_{1a}$ and R$_{2a}$ are taken together with the carbon atom to which they are attached to form an optionally substituted C$_3$-C$_{10}$-cycloalkyl or an optionally substituted 3 to 10-membered heterocyclic; X$_1$, m, A$_1$, A$_2$, A$_3$, Y, Z, R$_1$ and R$_2$ are as previously defined.

In another embodiment, the compound of Formula (I) is represented by Formula (IIa-2), (IIb-2), or (IIc-2), or a pharmaceutically acceptable salt thereof, wherein M is —CR'R$_{1a}$R$_{2a}$ or —NR$_1$R$_2$; wherein R$_{1a}$ and R$_{2a}$ are taken together with the carbon atom to which they are attached to form an optionally substituted C$_3$-C$_8$ cycloalkyl or an optionally substituted 3- to 8-membered heterocyclic, and R$_1$ and R$_2$ are taken together with the nitrogen atom to which they are attached to form an optionally substituted 3- to 8-membered heterocyclic, wherein said cycloalkyl or heterocyclic contains 0 to 3 exocyclic double bonds including =CR$_{1a}$R$_{2a}$, =O, =NR$_1$; and R$_1$, R$_2$, R$_{1a}$ and R$_{2a}$ are as previously defined; wherein each of the said hererocyclic contains 1 to 3 heteroatoms selected from O, N, and S.

In yet another embodiment, the compound of Formula (I) is represented by Formula (IIa-2), (IIb-2), or (IIc-2), or a pharmaceutically acceptable salt thereof, wherein M is —CR'R$_{1a}$R$_{2a}$ or —NR$_1$R$_2$; wherein R$_{1a}$ and R$_{2a}$ are taken together with the carbon atom to which they are attached to form an optionally substituted C$_3$-C$_{10}$ bi- or tri-cycloalkyl or an optionally substituted 3- to 10-membered bi- or tri-heterocyclic, and R$_1$ and R$_2$ are taken together with the nitrogen atom to which they are attached to form an optionally substituted 3- to 10-membered bi- or tri-heterocyclic, wherein in each case (i) the second ring is connected to the first ring at the same carbon atom in a spiro pattern; or (ii) the second ring is connected to the to the first ring at two vicinal 1,2-atoms in a fused pattern; or (iii) the second ring is connected to to the first ring at two 1,3-atoms or 1,4-atoms in a bridged pattern; in such cases the first ring is a 4-, 5-, 6- or 7-membered ring system.

In another embodiment, the compound of Formula (I) is represented by Formula (IIIa), (IIIb), (IIIc), (IIId), (IIIe), or (IIIf), or a pharmaceutically acceptable salt thereof:

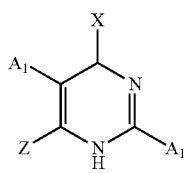
IIIa

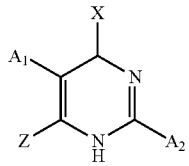
IIIb

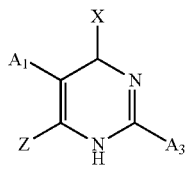
IIIc

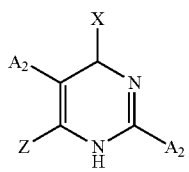
IIId

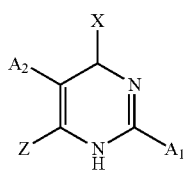
IIIe

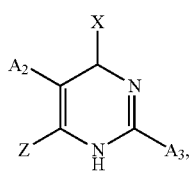
IIIf wherein $A_1$, $A_2$, $A_3$, X and Z are as previously defined.

In another embodiment, the compound of Formula (I) is represented by Formula (IIIa-1), (IIIb-1), (IIIc-1), (IIId-1), (IIIe-1), or (IIIf-1), or a pharmaceutically acceptable salt thereof:

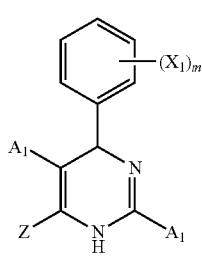
IIIa-1

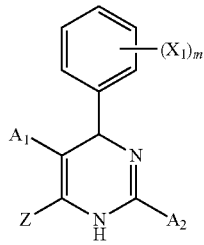
IIIb-1

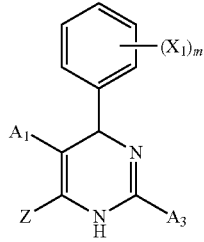
IIIc-1

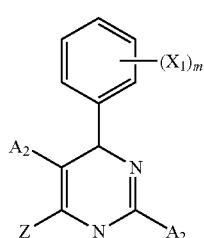
IIId-1

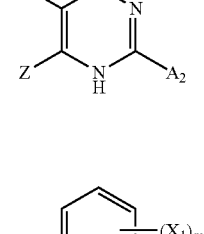
IIIe-1

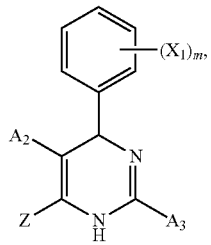
IIIf-1 wherein $A_1$, $A_2$, $A_3$, $X_1$, m, and Z are as previously defined.

In another embodiment, the compound of Formula (I) is represented by Formula (IIIa-2), (IIIb-2), (IIIc-2), (IIId-2), (IIIe-2), or (IIIf-2), or a pharmaceutically acceptable salt thereof:

IIIa-2

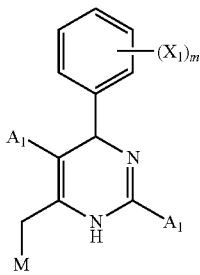

IIIb-2

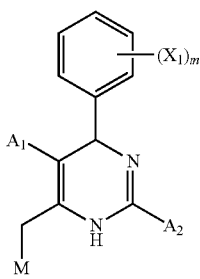

IIIc-2

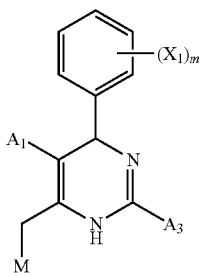

IIId-2

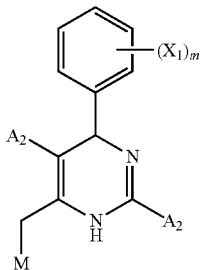

IIIe-2

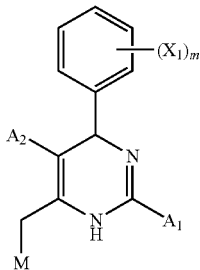

IIIf-2

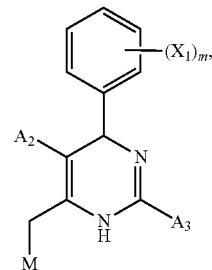

wherein $A_1$, $A_2$, $A_3$, $X_1$, m, M, $R_1$ and $R_2$ are as previously defined.

In another embodiment, the compound of Formula (I) is represented by Formula (IVa), (IVb), or (IVc), or a pharmaceutically acceptable salt thereof:

IVa

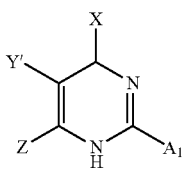

IVb

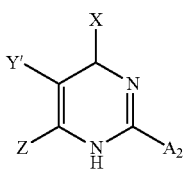

IVc

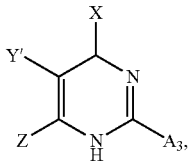

wherein Y' is selected from the group consisting of —$SO_2R_3$, —$SO_2NR_1R_2$, —$C(O)R_3$, —CN, —$N(R_1)C(O)R_3$, —$N(R_1)C(O)NR_1R_2$, —$N(R_1)C(O)OR_3$, —$P(O)(OR_1)_2$; $A_1$, $A_2$, $A_3$, X, Z, $R_1$, $R_2$ and $R_3$ are as previously defined.

In certain embodiments, the present invention relates to compounds of Formula (I) and pharmaceutically acceptable salts thereof, wherein X is selected from the groups set forth below:

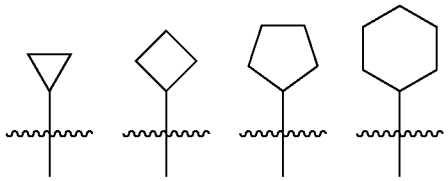

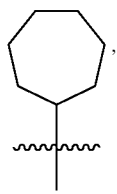

wherein each of the above shown groups is optionally substituted. The preferred substitution groups include optionally substituted methyl, halo, —CN, =O, =NR$_1$, —OR$_1$, and —NR$_1$R$_2$; R$_1$, R$_2$ are as previously defined.

In certain embodiments, the present invention relates to compounds of Formula (I) and pharmaceutically acceptable salts thereof, wherein Z is selected from the groups set forth below:

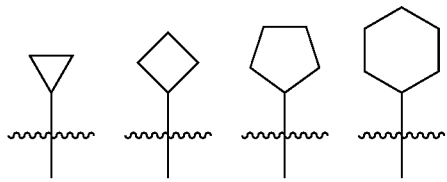

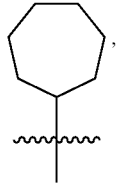

wherein each of the above shown groups is optionally substituted. The preferred substitution groups include optionally substituted methyl, halo, —CN, =O, =NR$_1$, —OR$_1$, and —NR$_1$R$_2$; R$_1$, R$_2$ are as previously defined.

In certain embodiments, the present invention relates to compounds of Formula (I) and pharmaceutically acceptable salts thereof, wherein Z is —CH$_2$M; M is selected from the groups set forth below:

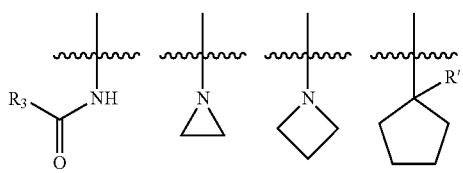

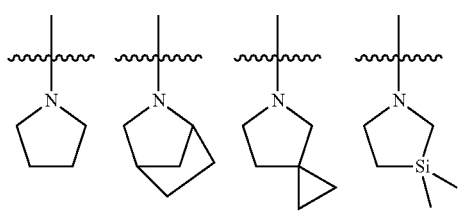

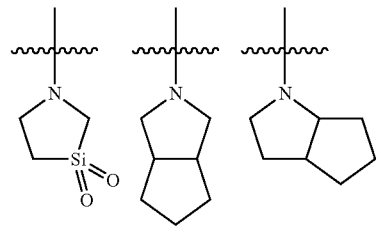

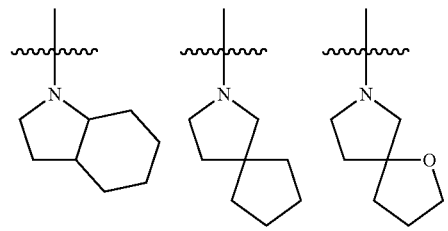

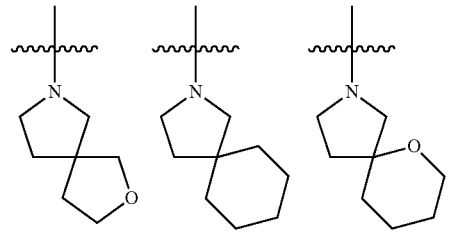

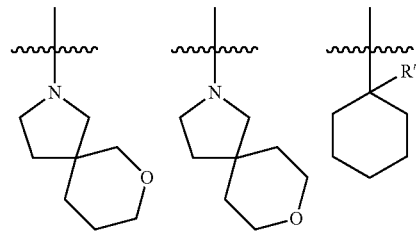

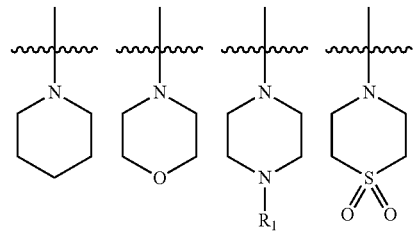

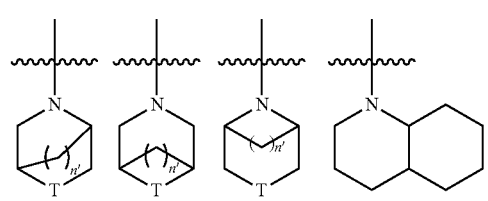

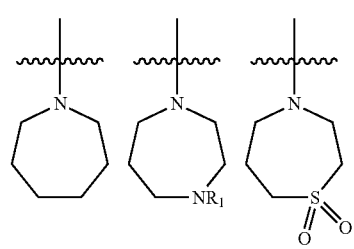

-continued

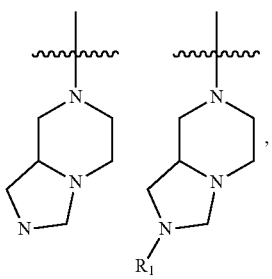

wherein each of the above shown groups is optionally substituted when possible; the preferred substituents include halo, =O, =NR$_1$, —OR$_1$, —NR$_1$R$_2$, —CN, —C(O)NR$_1$R$_2$, —S(O)$_2$R$_3$, —C(O)NR$_1$S(O)$_2$R$_3$, and optionally substituted methyl; T is O, NR$_1$ or CR$_{1a}$R$_{2a}$; wherein n' is 1, 2 or 3; R', R$_1$ R$_{1a}$, R$_2$ and R$_{2a}$ are as previously defined.

In certain embodiments, the present invention relates to compounds of Formula (I) and pharmaceutically acceptable salts thereof, wherein Y is selected from the groups set forth below:

-continued

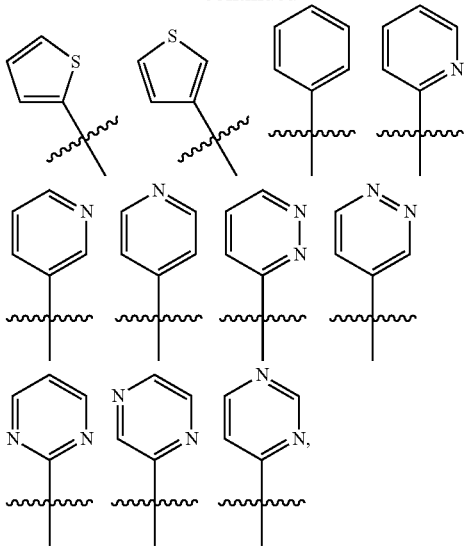

wherein each of the above shown groups is optionally substituted when possible. The preferred substituents include optionally substituted methyl, halo, —CN, —OR$_1$, —NR$_1$R$_2$; R$_1$ and R$_2$ are as previously defined.

In certain embodiments, the present invention relates to compounds of Formula (I) and pharmaceutically acceptable salts thereof, wherein A is optionally substituted phenyl, optionally substituted thiophenyl, optionally substituted imidazolyl, optionally substituted thiazolyl, optionally substituted oxazolyl, optionally substituted pyridyl.

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., R$_1$, R$_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention. For example, at least one tautomer has the structure as shown in Formula (I'):

(I')

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibiting, disrupting or accelerating) the activity of HBV cccDNA. In yet another embodiment, the compounds of the invention can be used in methods of diminishing or preventing the formation of HBV cccDNA. In another embodiment, the additional therapeutic agent is selected from immune modulator or immune stimulator therapies, which includes T-cell response activator AIC649 and biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists; or therapeutic vaccines to stimulate an HBV-specific immune response such as virus-like particles composed of HBcAg and HBsAg, immune complexes of HBsAg and HBsAb, or recombinant proteins comprising HBx, HBsAg and HBcAg in the context of a yeast vector; or immunity activator such as SB-9200 of certain cellular viral RNA sensors such as RIG-I, NOD2, and MDA5 protein, or RNA interference (RNAi) or small interfering RNA (siRNA) such as ARC-520, ARC-521, ARB-1467, and ALN-HBV RNAi, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence such as REP 2139. In an embodiment of the combination therapy, the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl) propyl] amino}methyl)phenyl] acetate), GS-9620 (4-Amino-2-butoxy-8-[3-(1-pyrrolidinylmethyl)benzyl]-7, 8-dihydro-6 (5H)-pteridinone), and RO6864018.

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system radical comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "azolyl group," as used herein, refers to 5-membered heteroaromatic ring containing at least one nitrogen atom. Preferred azolyl groups contain a nitrogen atom and at least one additional heteroatom, preferably a nitrogen, oxygen or sulfur atom. Azolyl groups include, but are not limited to, pyrrolyl, pyrazolyl, imidazolyl, thiazolyl, 1,2,4-thiadiazolyl, 1,2,5-thiadiazolyl, 1,3,4-thiadiazolyl, oxazolyl, isoxazolyl, 1,3,4-oxadiazolyl, 1,2,4-oxadiazolyl, 1,2,5-oxadiazolyl, 1,2,3-triazolyl, 1,2,4-triazolyl, tetrazolyl. An azole group is termed "ortho" substituted in reference to two substituents which are on adjacent ring atoms. An azole group is termed "meta" substituted in reference to two substituents which are not on adjacent ring positions.

The term "bicyclic azolyl" or "bicyclic azolyl group" refers to an aromatic ring system consisting of two rings wherein at least one ring is an azole group; and the two rings can be fused or covalently attached. Preferred bicyclic azolyl groups are those in which an azole ring is fused to a six-membered aromatic or heteroaromatic ring. Such groups include, but are not limited to, benzimidazolyl, benzopyrazolyl, benzotriazolyl, benzoxazolyl, benzisoxazolyl, benzothiazolyl, imidazolopyridyl, pyrazolopyridyl, thiazolopyridyl, oxazolopyridyl, isoxazolopyridyl, triazolopyridyl, and tetrazolopyridyl.

The term "alkyl" as used herein, refers to a saturated, straight- or branched-chain hydrocarbon radical. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to a straight- or branched-chain hydrocarbon radical having at least one carbon-carbon double bond. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring radical. One or more carbon atom in a cycloalkyl group may be optionally oxo-substituted. Preferred cycloalkyl groups include $C_3$-$C_8$ cycloalkyl, $C_3$-$C_{10}$ cycloalkyl and $C_4$-$C_7$ cycloalkyl. Examples of $C_3$-$C_8$ cycloalkyl include, but not limited to, cyclopropyl, cyclobutyl, cyclopentyl, cyclohexyl, cyclopentyl and cyclooctyl; and examples of $C_4$-$C_7$ cycloalkyl include, but are not limited to, cyclopentyl, cyclohexyl, bicyclo [2.2.1] heptyl, and the like.

The term "cycloalkenyl", as used herein, refers to monocyclic or polycyclic carbocyclic ring radical having at least one carbon-carbon double bond and the carbon atoms may be optionally oxo-substituted. A cycloalkenyl group is derived from preferred cycloalkenyl groups include $C_3$-$C_8$ cycloalkenyl or $C_5$-$C_7$ cycloalkenyl groups. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chain, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, spiro, or bridged system, where (i) each ring system contains at least one heteroatom independently selected from oxygen, sulfur and nitrogen, (ii)

each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]heptyl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH— heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, —$CO_2$—$C_3$-$C_{12}$-cycloalkyl, —$CO_2$— aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH— heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$— heterocycloalkyl, —NHC(O)$NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH— heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloro-acetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis*, 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al.,

*Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of straight chain and branched $C_1$-$C_6$-alkanoic acids.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Combination and Alternation Therapy for HBV

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combination are selected from the group consisting of a HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Although the invention has been described with respect to various preferred embodiments, it is not intended to be limited thereto, but rather those skilled in the art will recognize that variations and modifications may be made therein which are within the spirit of the invention and the scope of the appended claims.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; $Boc_2O$ for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; $Bu_3SnH$ for tributyltin hydride; BOP for (benzotriazol-1-yloxy)tris(dimethylamino)phospho-nium Hexafluorophosphate; Brine for sodium chloride solution in water; BSA for N,O-bis(trimethylsilyl)acetamide; CDI for carbonyldiimidazole; DCM or $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; dppb for diphenylphos-phinobutane; DBU for 1,8-diazabicyclo[5.4.0]-undec-7-ene; DCC for N,N'-dicyclohexyl-carbodiimide; DEAD for diethylazodicarboxylate; DIAD for diisopropyl azodicarboxylate; DIPEA or $(i-Pr)_2EtN$ for N,N,-diisopropylethyl amine; Dess-Martin periodinane for 1,1,1-tris(acetyloxy)-1,1-dihydro-1,2-benziodoxol-3-(1H)-one; DMAP for 4-dimethyl-amino-pyridine; DME for 1,2-dimethoxyethane; DMF for N,N-dimethylformamide; DMSO for dimethyl sulfoxide; DMT for di(p-methoxyphenyl)-phenylmethyl or dimethoxytrityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; $Et_2O$ for diethyl ether; HATU for O-(7-azabenzotriazol-1-yl)-N,N,N',N',-tetramethyluronium Hexafluoro-phosphate; HCl for hydrogen chloride; HOBT for 1-hydroxybenzotriazole; $K_2CO_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethyl-piperidinate; MeOH for methanol; Mg for magnesium; MOM for methoxymethyl; Ms for mesyl or $-SO_2-CH_3$; $Ms_2O$ for methanesulfonic anhydride or mesyl-anhydride; MTBE for t-butyl methyl ether; $NaN(TMS)_2$ for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4Cl$ for ammonium chloride; NMO for N-methylmorpholine N-oxide; $NaIO_4$ for sodium periodate; Ni for nickel; OH for hydroxyl; $OsO_4$ for osmium tetroxide; PPA for polyphophoric acid; PTSA for p-toluenesulfonic acid; PPTS for pyridiniump-toluenesulfonate; PhI$(OPiv)_2$ for Bis(tert-butylcarbonyloxy)iodobenzene; $Rh_2(Esp)_2$ for Bis[rhodium(α,α,α',α'-tetramethyl-1,3-benzenedipropionic acid)]; TBAF for tetrabutylammonium fluoride; TEA or $Et_3N$ for triethylamine; TES for triethylsilyl; TESCl for triethylsilyl chloride; TESOTf for triethylsilyl trifluoromethanesulfonate; TFA for trifluoroacetic acid; THF for tetrahydrofuran; TMEDA for N,N,N',N'-tetramethylethylene-diamine; TPP or $PPh_3$ for triphenyl-phosphine; Troc for 2,2,2-trichloroethyl carbonyl; Ts for tosyl or $-SO_2-C_6H_4CH_3$; $Ts_2O$ for tolylsulfonic anhydride or tosyl-anhydride; TsOH for p-tolylsulfonic acid; Pd for palladium; Ph for phenyl; POPd for dihydrogen dichlorobis(di-tert-butylphosphinito-κP)palladate(II); $Pd_2(dba)_3$ for tris (dibenzylideneacetone) dipalladium (0); $Pd(PPh_3)_4$ for tetrakis(triphenylphosphine)-palladium (0); $PdCl_2(PPh_3)_2$ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose, and are not meant to limit the scope of the invention. Equivalent, similar, or suitable solvents, reagents or reaction conditions may be substituted for those particular solvents, reagents, or reaction conditions described herein without departing from the general scope of the method of synthesis.

The nature of the group B in Formula I will have a significant effect on the choice of the synthesis methods, as demonstrated below.

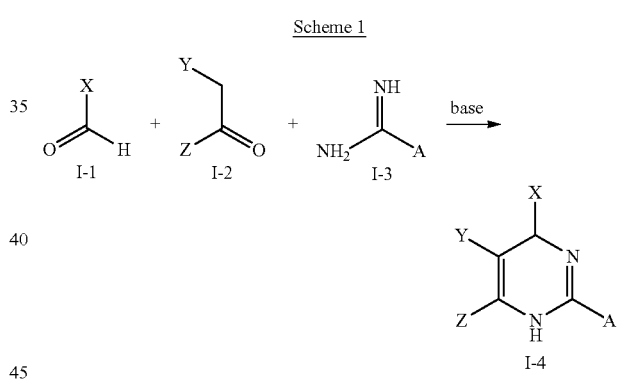

Scheme 1

When B in Formula I is a hydrogen, an illustrative method is shown in Scheme 1, where X, A, Y, Z are as defined previously for formula I. The starting materials, an aldehyde I-1, a ketone I-2, and an amidine I-3 are all either commercially available or can be easily prepared by those of skill in the art. The dihydropyrimidine core I-4 can be prepared in one pot process from an aldehyde I-1, a ketone I-2 and an amidine I-3 (or its salt) in the presence of a suitable base such as potassium acetate or potassium bicarbonate in a solvent such as methanol, or trifluoroethanol. Most frequently, elevated temperature is required for this transformation. Starting from this core I-4, A, X, Y, Z could be individually manipulated and converted to varieties of functional groups.

For instance, when Z in I-4 is a methyl, this methyl could be further functionalized easily. One specific example is shown in scheme 1a, when I-4a was treated with NBS, the methyl bromide I-5 will be obtained. The natural of this allylic bromide indicated it can be displaced efficiently. Therefore, when I-5a is reacted with various nucleophiles, like amines or alcohol (MH), in the presence of a suitable base, such as TEA or pyridine will afford the a more complicated structure I-6a. M is as previously defined.

Scheme 1a

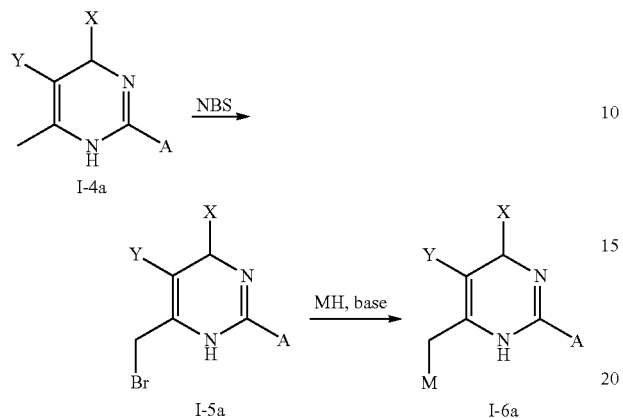

Alternatively, Y in the formula I-4 also can be further manipulated. For instance, as shown in Scheme 1b, wherein Y is an ester, $R_3$ is as defined as previously. The N-3 can be easily protected with a protective group, for instance, -Boc as a preferred group to afford I-5b. In the case while $R_3$ is t-Butyl or allyl, then ester I-5b can be converted to an advanced carboxyl acid intermediate I-6b when treated with strong acid (HCl or TFA) or Pd(PPh$_3$)$_4$/Morpholine, respectively. By taking advantage of this carboxyl acid as a key intermediate, various functional groups can be generated from it. One specific example is shown in the same scheme, this carboxyl acid is condensed with N,O-dimethyl-hydroxylamine hydrochloride in the presence of a dehydration reagent such as EDC or DCC as well as a base like TEA, DIPEA to give the Weinreb amide I-7b. In the next step, this Weinreb amide is reacted with all sorts of Grignard reagents to provide various ketones 1-8b, which could serve as a final targets or later stage intermediate for more complicated structures. It should be noted, the protective group can be introduced or removed at any given step in order to accommodate the need of the synthesis. $R_3$ is as previously defined.

Scheme 1b

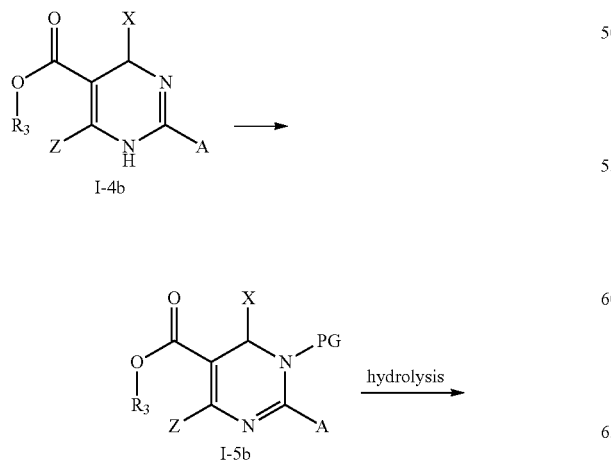

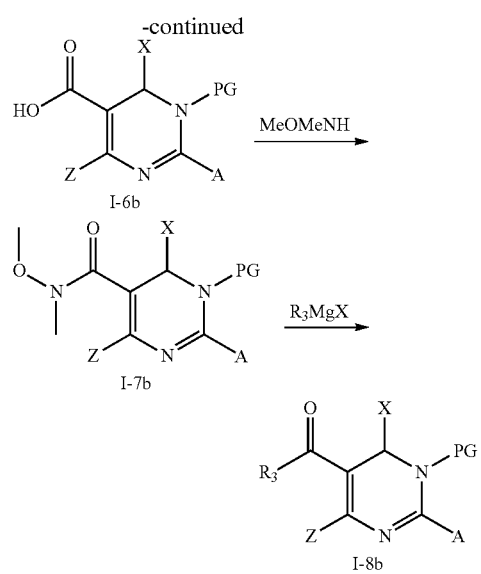

In another specific example as shown in Scheme 1c, the Weinreb amide I-7b can be reduced to afford the aldehyde I-8c, which when reacted with acetone in the presence of a base such as LDA will offer the α,β-unsaturated ketone I-9c. I-9c is treated with hydroxyl amine followed by an iodine induced cyclization to afford the isoxazole I-10c.

Scheme 1c

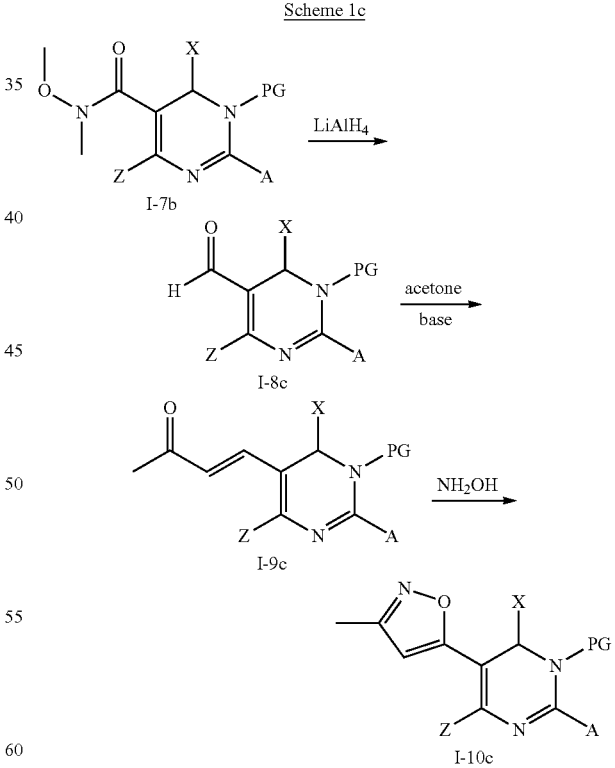

In yet another example as shown in Scheme 1d, the key intermediate carboxyl acid was condensed with an amine to afford various amide in the presence of a dehydration reagent, such as HATU, and a suitable base. Wherein $R_1$ and $R_2$ are as previously defined. In the case when $R_1=R_2=H$, the primary amide is treated with TFAA as a dehydration reagent to afford the nitriles I-8d. This nitrile can served as final target as well as an advanced intermediate. As shown in the same scheme, when treated with sodium azide, the nitrile is converted to a tetrazole I-9d.

chemical procedure described in Scheme 1a, I-7f will be converted to I-8f. I-8f then can be converted to the targets I-9f via the coupling reaction described in scheme 1e.

Scheme 1d

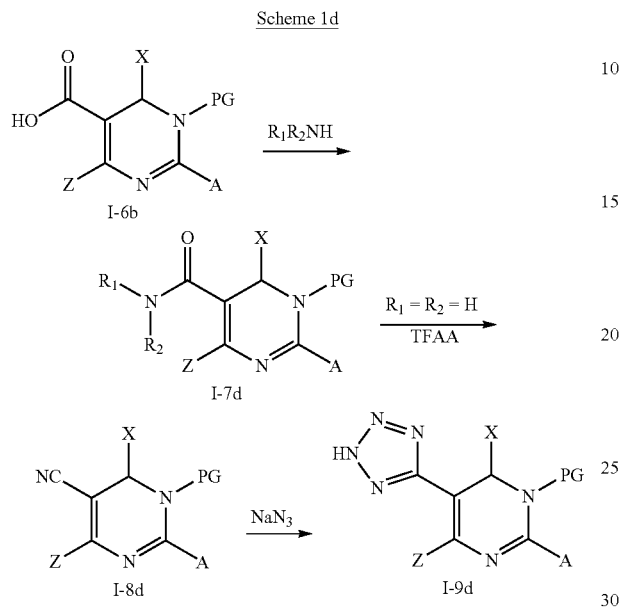

In yet another specific example as shown Scheme 1e, when the carboxyl acid I-6b is treated with pyridinium tribromide in the presence a base such as pyridine, a bromide I-7e will be produced. The bromide reacts with various aryl or heteroaryl boronic ester/acid or tin reagent, which can be commercial available or easily prepared by those familiar with the skill of the arts, under the Pd(0) catalyzed coupling conditions to give the target molecule I-8e. (see reviews: A. Suzuki, Pure Applied Chem., 1991, 63, 419; A. Suzuki, Handbook of Organopalladium Chemistry for Organic Synthesis, 2002, 1, 249; A. Anastasia, et al, Handbook of Organopalladium Chemistry for Organic Synthesis, 2002, 1, 311).

Scheme 1e

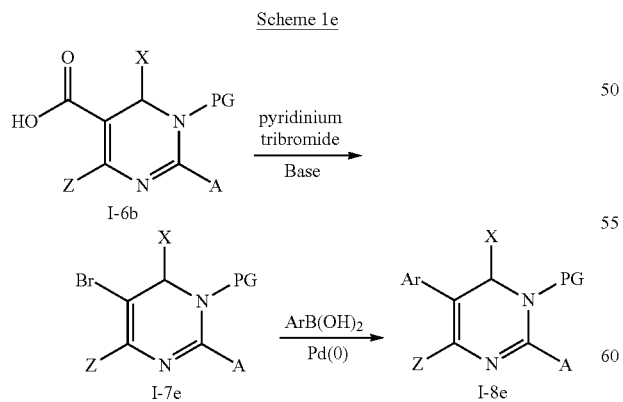

In yet another specific example as shown in Scheme 1f, when the carboxylic acid I-6f, (while Z is methyl, PG is Boc in I-6b) is treated with at least two equivalents of NBS, a di-bromo compound I-7f will be obtained. Following similar Scheme 1f

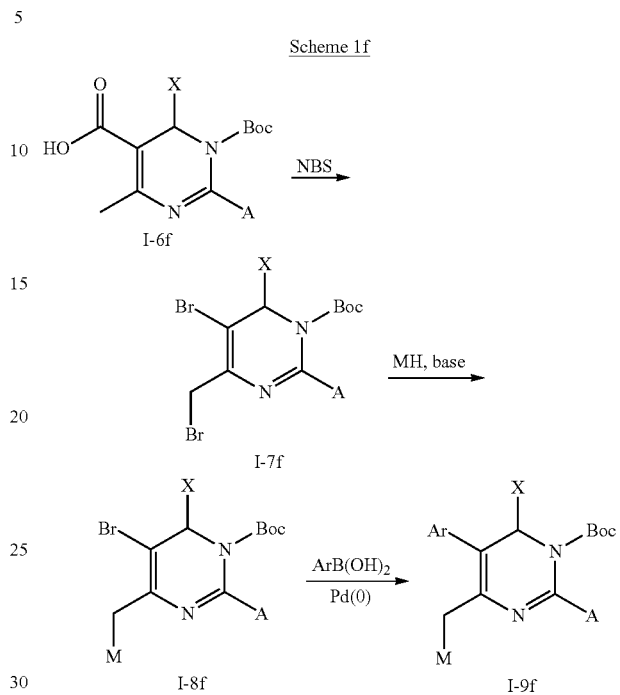

On the other hand when B is CN or an alkyl group, a stepwise route is required for the preparation of the final targets. As illustrated in Scheme 2, aldehyde I-1 and I-2 are reacted with each other in the presence of a catalyst system, such as piperidine/acetic acid to afford the α,β-unsaturated ketone II-1. This α,β-unsaturated ketone II-1 reacts with a copper reagent CuB, which can be commercially available or can be easily generated in situ from CuI and BMgX (or BLi). The newly formed α,β-unsaturated ketone II-2 then reacts with I-3 in a similar process described above as in the one-pot process to afford the desired target I.

Scheme 2

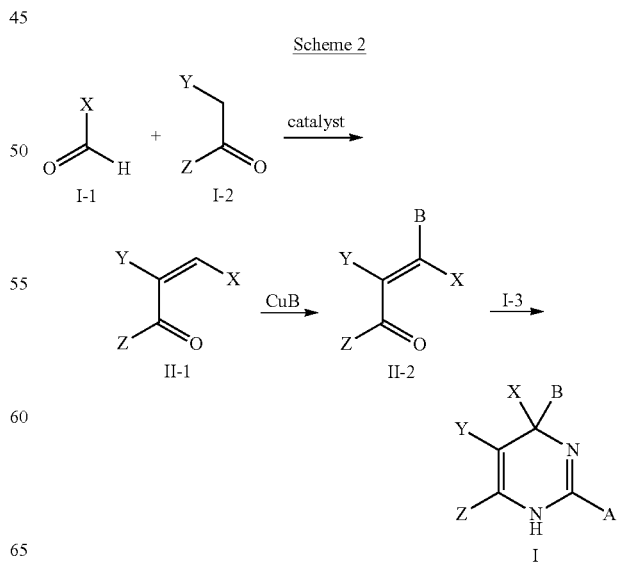

Alternatively, in certain cases, when B is hydrogen, a step wise procedure similar as in Scheme 2 is required to achieve the targets.

A specific example is shown in Scheme 2a, an aromatic aldehyde I-1a is reacted with α-sulfonyl ketone I-2a in the presence of piperidine and acetic acid to afford α,β-unsaturated ketone II-1a, this intermediate in turn reacted with the aryl or heteroaryl amidine (or its salt) in DMF while heated at proper temperature to afford the target I-a.

Scheme 2a

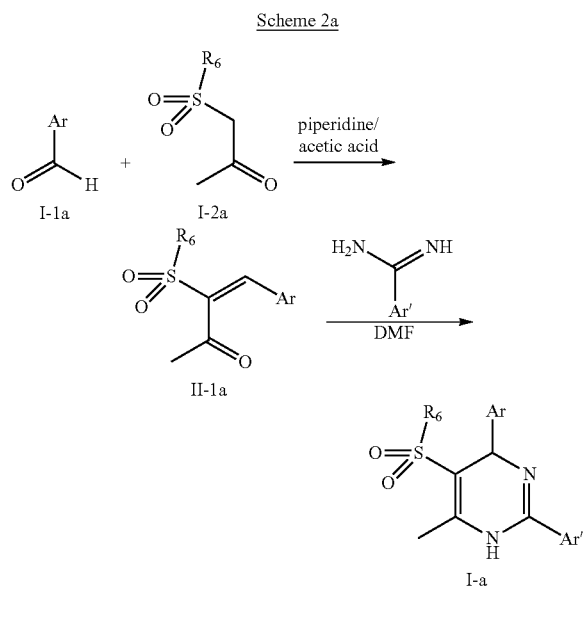

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

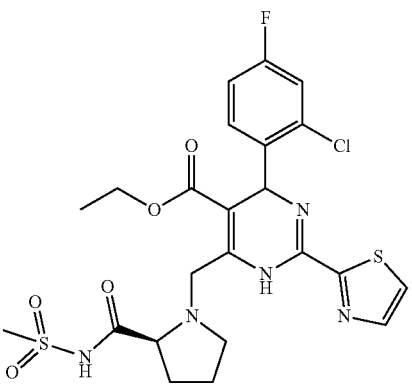 [SMILES: CCOC(=O)C1=C(CN2CCC[C@H]2C(=O)NS(C)(=O)=O)NC(c2nccs2)=NC1c1ccc(F)cc1Cl]

Step 1a.

A mixture of ethyl 3-oxobutanoate (7.61 g, 58.47 mmol), 2-chloro-4-fluorobenzaldehyde (7.76 g, 48.94 mmol), 1,3-thiazole-2-carboximidamide HCl salt (8.0 g, 48.78 mmol) and KOAc (9.56 g, 97.41 mmol) in CF$_3$CH$_2$OH (200 mL) was stirred for 24 hours at 90° C. After being cooled, it was concentrated and the residue was partitioned (EtOAc-brine). The organic was dried (Na$_2$SO$_4$), filtered and concentrated. The residue was chromatographed (silica, ethyl acetate/petroleum ether) to give the desired compound as a yellow solid (8.2 g, 44%). ESIMS m/z=380.2, 382.2 [M+H]$^+$.

Step 1b.

Into a solution of the compound from step 1a (2.3 g, 6.06 mmol) in CCl$_4$ (40 mL) was charged with NBS (864 mg, 4.85 mol) in portions at 0° C. over 30 minutes. The solution was stirred for 30 minutes at rt before being quenched with water and partitioned (CH$_2$Cl$_2$—H$_2$O). The organic was dried (Na$_2$SO$_4$), filtered and concentrated. The residue was chromatographed (silica, ethyl acetate/petroleum ether) to give the desired compound as a yellow solid (1.3 g, 47%). ESIMS m/z=458.1, 460.1 [M+H]$^+$.

Step 1c.

A solution of ((benzyloxy)carbonyl)-L-proline (500 mg, 2.32 mmol), methanesulfonamide (285 mg, 3.00 mmol), EDCI (576 mg, 3.00 mmol), DMAP (369 mg, 3.00 mmol) in DCM (15 mL) was stirred for 4 hours at rt. It was diluted with DCM (100 mL) and washed with H$_2$O (×2) and brine. The organic was dried (Na$_2$SO$_4$), filtered and concentrated. The residue was chromatographed (silica, ethyl acetate/petroleum ether) to give the desired compound as yellow oil (0.5 g, 74%). ESIMS m/z=327.2 [M+H]$^+$.

Step 1d.

A mixture of the compound from step 1c (500 mg, 1.53 mmol), palladium on carbon (10 wt %, 100 mg) in methanol (10 mL) was stirred for 2 hours at rt under $H_2$ atmosphere (balloon) before filtration. The filtrate was concentrated to give 200 mg (68%) of desired compound as yellow oil. ESIMS m/z=193.1[M+H]$^+$. This material was used in the next step without further purification.

Step 1e.

A solution of the compounds from step 1b (100 mg, 0.52 mmol) and step 1d (120 mg, 0.26 mmol) and DIPEA (67 mg, 0.52 mmol) in DCM (6 mL) was stirred for 3 hours at rt before it was concentrated. The residue was chromatographed (silica, ethyl acetate/petroleum ether) to give the title compound (mixture of diastereomers) as a yellow oil (38 mg, 13%). ESIMS m/z=570.10, 572.10 [M+H]+; $^1$H NMR (300 MHz, methanol-d4) δ 7.94 (1H, s), 1.09 (3H, t), 7.80-7.90 (1H, m), 7.50-7.60 (1H, m), 7.10-7.30 (2H, m), 6.20 (1H, d), 4.20-4.80 (2H, m), 4.10 (2H, q), 3.80-4.05 (1H, m), 3.35-3.65 (1H, m), 3.00-3.20 (1H, m), 2.90 (3H, s), 2.40-2.60 (1H, m), 2.00-2.40 (3H, m).

Example 2

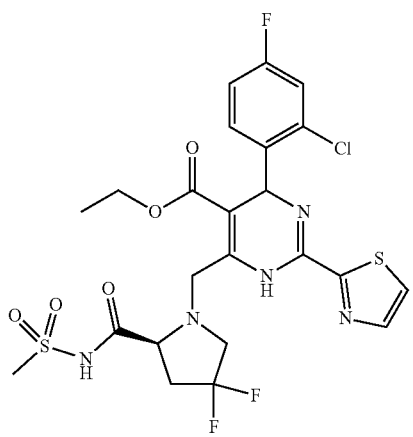 [SMILES: CCOC(=O)C1=C(CN2CC(F)(F)C[C@H]2C(=O)NS(C)(=O)=O)NC(c2nccs2)=NC1c1ccc(F)cc1Cl]

Step 2a.

The mixture of compound from step 1b (200 mg, 0.44 mmol), (S)-4,4-difluoropyrrolidine-2-carboxylic acid (79 mg, 0.52 mmol) and DIPEA (280 mg, 2.17 mmol) in ClCH$_2$CH$_2$Cl (10 mL) was stirred for 3 hours at rt. it was concentrated and the residue was partitioned (EtOAc-brine). The organic was dried (Na$_2$SO$_4$), filtered and concentrated. The residue was Flash-Prep-HPLC (C18, MeCN/H$_2$O) to give the desired compound as a yellow solid (130 mg, 57%). ESIMS m/z=529.15, 531.15 [M+H]$^+$.

Step 2b.

Into a solution of step 2a (160 mg, 0.30 mmol), methanesulfonamide (35 mg, 0.37 mmol) and HATU (140 mg, 0.37 mmol) in CH$_2$Cl$_2$ (5 mL) was added DIEPA (50 mg, 0.39 mmol). The resulting solution was stirred for 3 hours at rt. It was partitioned (DCM-brine). The organic was dried (Na$_2$SO$_4$), filtered and concentrated. The residue was Flash-Prep-HPLC (C18, MeCN/H$_2$O) to give the title compound (mixture of diastereomers) as a yellow solid (53.7 mg, 29%). ESIMS m/z=605.9, 607.9 [M+H]+; $^1$H NMR (DMSO): δ 0.90-1.15 (m, 3H), 2.23-2.45 (m, 1H), 2.50-2.62 (m, 1H), 2.80-3.15 (m, 4H), 3.29-3.55 (m, 1H), 3.55-3.77 (m, 1H), 3.92-4.02 (m, 3H), 4.02-4.27 (m, 1H), 5.70-6.10 (m, 1H), 6.80-7.21 (m, 1H), 7.21-7.52 (m, 2H), 7.57-7.82 (m, 1H), 7.82-8.03 (m, 1H).

Example 3

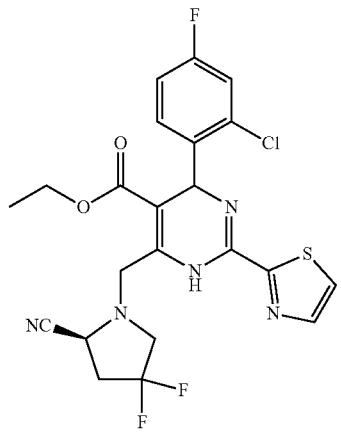 [SMILES: CCOC(=O)C1=C(CN2CC(F)(F)C[C@H]2C#N)NC(c2nccs2)=NC1c1ccc(F)cc1Cl]

Step 3a.

Into a solution of (S)-1-(tert-butoxycarbonyl)-4,4-difluoropyrrolidine-2-carboxylic acid (500 mg, 1.98 mmol), triethylamine (303 mg, 2.99 mmol) in dichloromethane (10 mL) was added pivaloyl chloride (326.4 mg, 2.39 mmol) dropwise at −15° C. over 10 minutes followed by aqueous ammonia (25%, 5 mL) and was stirred for 1 hour at 0° C. before it was partitioned (CH$_2$Cl$_2$—H$_2$O). The organic was dried (Na$_2$SO$_4$), filtered and concentrated to give the desired compound 602 mg (121%) as off-white liquid. ESIMS m/z=151.2 [M-Boc+H]$^+$. This material was used in the next step without further purification.

Step 3b.

A solution of crude compound from step 3a (602 mg, 2.40 mmol) and TFA (3 mL) in DCM (1 mL) was stirred 2 hours at rt. It was concentrated to give 612 mg of the desired compound (170%) as yellow oil. ESIMS m/z=151.2 [M+H]$^+$. The material was used directly in the next step without further purification.

Step 3c.

A solution of compound from step 1b (200 mg, 0.44 mmol), step 3b (130 mg, 0.87 mmol), DIPEA (224 mg, 1.73 mmol) in 1,2-dichloroethane (5 mL) was stirred for 24 hours at rt. The resulting mixture was concentrated under vacuum and purified by Flash-Prep-HPLC(C18, MeCN/H$_2$O) to give 217 mg of the desired compound (93%) as a yellow solid. ESIMS m/z=528.0, 530.0 [M+H]$^+$.

Step 3d.

To the solution of compound from step 3c (240 mg, 0.45 mmol) and pyridine (79 mg, 1.00 mmol) in DCM (5 mL) was added TFAA (210 mg, 1.00 mmol) dropwise at 0° C. The reaction was stirred overnight at rt before was concentrated. The residue was purified by Flash-Prep-HPLC (C18, MeCN/H$_2$O) to give the title compound (mixture of diastereomers) as yellow solid (153.3 mg (66%)). ESIMS m/z=510.2, 512.2 [M+H]+; $^1$H NMR (CD$_3$OD): δ$_H$ (400 MHz, Chloroform-d) 1.17 (3H, t), 2.56-2.95 (2H, m), 3.12-3.59 (2H, m), 3.92-4.60 (5H, m), 6.21 (1H, d), 6.98 (1H, td), 7.17 (1H, dd), 7.36 (1H, dd), 7.53 (1H, s), 7.88 (1H, dd).

Example 4

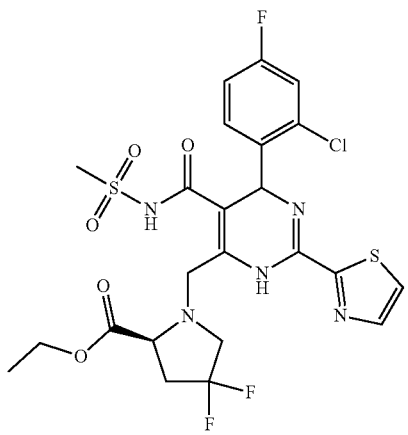 [SMILES: CCOC(=O)[C@@H]1CC(F)(F)CN1CC1=C(C(=O)NS(C)(=O)=O)C(c2ccc(F)cc2Cl)N=C(c2nccs2)N1]

Step 4a.

A mixture of (S)-1-(t-butoxycarbonyl)-4-oxopyrrolidine-2-carboxylic acid (3 g, 13.03 mmol), DMAP (4.8 g, 39.29 mmol), ethanol (720 mg, 15.63 mmol), EDCI (5.1 g, 26.60 mmol) in DCM (25 mL) was stirred for 12 hours at rt before being quenched with water and partitioned (CH$_2$Cl$_2$—H$_2$O). The organic was dried (Na$_2$SO$_4$), filtered and concentrated to give the desired compound as a yellow colorless oil (2 g, 59%). ESIMS m/z=202.0 [M-tBu]$^+$. The material was used directly in the next step without further purification.

Step 4b.

Into the solution of the compound from step 4a (1.9 g, 7.36 mmol) in DCM (15 mL) was charged with DAST (3.2 g, 19.85 mmol) dropwise at 0° C. over 30 minutes. The solution was stirred for 12 hours at rt before being quenched with water and partitioned (CH$_2$Cl$_2$—H$_2$O). The organic was dried (Na$_2$SO$_4$), filtered and concentrated to give the desired compound as a colorless oil (1.4 g, 68%). ESIMS m/z=224 [M-tBu]$^+$. This material was used directly in the next step without further purification.

Step 4c.

A solution of the compound from step 4b (700 mg, 2.50 mmol) in TFA (10 mL) was stirred for 12 hours at rt. It was concentrated to give the desired compound as a yellow solid (0.5 g, 90%). ESIMS m/z=180.00 [M+H]$^+$. This material was used directly in the next step without further purification.

Step 4d.

A mixture of t-butyl 3-oxobutanoate (1.9 g, 12.01 mmol), 2-chloro-4-fluorobenzaldehyde (1.9 g, 11.98 mmol), 1,3-thiazole-2-carboximidamide HCl salt (1.64 g, 10.00 mmol) and KOAc (1.96 g, 19.97 mmol) in CF$_3$CH$_2$OH (50 mL) was stirred for 24 hours at 90° C. After concentrated, the residue was partitioned (EtOAc-brine). The organic was dried (Na$_2$SO$_4$), filtered and concentrated. The residue was chromatographed (silica, ethyl acetate/petroleum ether) to give the desired compound as a yellow solid (1.4 g, 34%). ESIMS m/z=408.0, 410.0 [M+H]$^+$.

Step 4e.

To a solution of the compound from step 4d (1.4 g, 3.43 mmol) in CCl$_4$ (20 mL) was charged with NBS (612 mg, 3.44 mmol) in portions at 0° C. over 30 minutes. The solution was stirred for 30 minutes at rt before being quenched with water and partitioned (CH$_2$Cl$_2$—H$_2$O). The organic was dried (Na$_2$SO$_4$), filtered and concentrated. The residue was chromatographed (silica, ethyl acetate/petroleum ether) to give the desired compound as a yellow solid (824 mg, 49%). ESIMS m/z=487.9, 489.9 [M+H]$^+$.

Step 4f.

A solution of the compound from step 4e (600 mg, 1.23 mmol), step 4c (330 mg, 1.84 mmol), DIPEA (480 mg, 3.71 mmol) in 1,2-dichloroethane (15 mL) was stirred for 12 hours at rt. It was diluted with DCM and washed with aq NH$_4$Cl and brine. The organic was dried (Na$_2$SO$_4$), filtered and concentrated. The residue was chromatographed (silica, DCM/MeOH) to give the desired compound as colorless oil (0.5 g, 69%). ESIMS m/z=585.1, 587.1 [M+H]$^+$.

Step 4g.

A solution of the compound from step 4f (400 mg, 0.68 mmol) in TFA (15 mL) was stirred for 12 hours at rt. it was concentrated. The residue was chromatographed (silica, DCM/MeOH) to give the desired compound as yellow solid (0.15 g, 41%). ESIMS m/z=529.0, 531.0 [M+H]$^+$.

Step 4h.

To a solution of compound from step 4g (130 mg, 0.26 mmol) and CDI (60 mg, 0.37 mmo) in THF (2 mL) was added DIPEA (50 mg, 0.37 mmol) at 0° C. It was stirred for 2 hours at rt to give a solution A. In another flask, LiHMDS (1M, 0.5 ml, 0.5 mmol) was added to a solution of methanesulfonamide (71 mg, 0.74 mmol) in THF (1 mL) at −78. After stirred 30 minutes, solution A was added dropwise. The mixture was stirred for 3 hours at rt, quenched with H$_2$O, partitioned (EtOAc-brine). The organic was dried (Na$_2$SO$_4$), filtered and concentrated. The residue was purified by Prep-HPLC (C18, MeCN/H$_2$O) to give the title compound (mixture of diastereomers) as a yellow solid (29 mg, 19.5%). ESIMS m/z=606.1, 608.1 [M+H]$^+$; $^1$H NMR (CDCl$_3$) δ (300 MHz, CDCl$_3$) 1.04 (3H, t), 0.7-1.0 (1.5H, m), 1.0-1.4 (1.7H, m), 1.8-2.2 (1.6H, m), 2.2-2.8 (4H, m), 2.8-3.5 (2H, m), 3.5-4.5 (4.5H, m), 6.0 (0.2H, s), 6.1-6.3 (0.5H, m), 6.8-7.2 (2.4H, m), 7.26-7.4 (1H, m), 7.4-7.6 (1H, m), 7.7-8.0 (1H, m), 8.9-9.2 (0.2 dbr).

Example 5

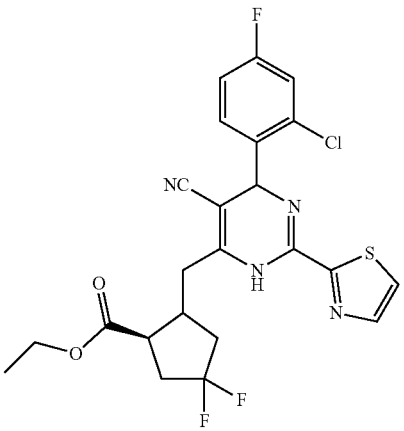 [SMILES: CCOC(=O)[C@@H]1CC(F)(F)CC1CC1=C(C#N)C(c2ccc(F)cc2Cl)N=C(c2nccs2)N1]

Step 5a.

A mixture of compound from 4g (100 mg, 0.19 mmol) HATU (79 mg, 0.21 mmol), DIEA (73 mg, 0.56 mmol), NH$_4$Cl (15 mg, 0.28 mmol) in DMF (8 mL) was stirred for 12 hours at rt before being quenched with water and partitioned (CH$_2$Cl$_2$—H$_2$O). The organic was dried (Na$_2$SO$_4$), filtered and concentrated to give the desired compound as a yellow oil (60 mg, 60%). ESIMS m/z=520, 522 [M+H]+. This material was used directly in the next step without further purification.

Step 5b.

A mixture of the compound from step 5a (55 mg, 0.10 mmol), TFAA (26.25 mg, 0.12 mmol), pyridine (12.3 mg, 0.16 mmol) in DMF (6 mL) was stirred for 4 hours at room temperature. It was concentrated. The residue was chromatographed (silica, ethyl acetate/petroleum ether) to give the title compound (mixture of diastereomers) as a yellow solid (26 mg, 49%). ESIMS m/z=510.2, 512.2 [M+H]+; 1H NMR (300 MHz, CDCl3), δ 1.30-1.40 (3H, m), 2.46-2.63 (1H, m), 2.65-2.80 (1H, m), 2.90-3.18 (1H, m), 3.46-3.64 (1H, m), 3.70-3.88 (3H, m), 4.28-4.37 (2H, m), 5.96 (1H, d), 7.00-7.10 (1H, m), 7.15-7.25 (1H, m), 7.32-7.47 (1H, m), 7.55 (1H, d), 7.95 (1H, d), 8.95-10.00 (1H, br).

Example 6

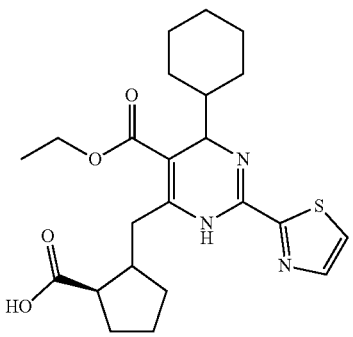 [SMILES: CCOC(=O)C1=C(CC2CCC[C@H]2C(=O)O)NC(c2nccs2)=NC1C1CCCCC1]

Step 6a.

A mixture of ethyl 3-oxobutanoate (0.4 g, 3 mmol), cyclohexanecarbaldehyde (0.34 g, 3 mmol), 1,3-thiazole-2-carboximidamide HCl salt (0.49 g, 3 mmol) and KOAc (0.59 g, 6 mmol) in CF3CH2OH (10 mL) was stirred for 24 hours at 90° C. After being cooled, it was partitioned (EtOAc-brine). The organic was dried (Na2SO4), filtered and concentrated. The residue was chromatographed (silica, ethyl acetate/petroleum ether) to give the desired compound as a yellow solid (0.35 g, 34%). ESIMS m/z=334.1 [M+H]+.

Step 6b.

To solution of the compound from step 6a (0.3 g, 0.9 mmol) in CCl4 (10 mL) was charged with NBS (160 mg, 0.9 mol) in portions at 0° C. over 30 minutes. It was stirred for 30 minutes at rt before being quenched with water and partitioned (CH2Cl2—H2O). The organic was dried (Na2SO4), filtered and concentrated. The residue was chromatographed (silica, ethyl acetate/petroleum ether) to give the desired compound as yellow oil (0.15 g, 40%). ESIMS m/z=412.1, 414.2 [M+H]+.

Step 6c.

A solution of the compound from step 6b (130 mg, 0.31 mmol), (2S)-pyrrolidine-2-carboxylic acid (54.3 mg, 0.47 mmol), DIPEA (119.97 mg, 0.93 mmol) in 1,2-dichloroethane (5 mL) was stirred for 12 hours at rt. It was diluted with DCM (20 mL) and washed with aq NH4Cl and brine. The organic was dried (Na2SO4), filtered and concentrated. The residue was purified by Flash-Prep-HPLC (C18, MeCN/H2O) to give the title compound (mixture of diastereomers) as a yellow solid (35.6 mg, 25%). ESIMS m/z=447.3 [M+H]+. 1H NMR (400 MHz, CDCl3), δ 0.90 (1H, m), 0.97-1.30 (7H, m), 1.34-1.61 (3H, m), 1.59-2.01 (6H, m), 2.15 (1H, td), 2.68 (1H, s), 3.15 (1H, d), 3.51 (1H, s), 3.95 (1H, d), 4.00-4.36 (3H, m), 4.44 (1H, d), 7.88-8.18 (2H, m), 9.98 (2H, s).

Example 7

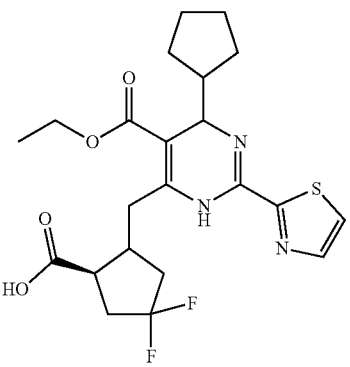 [SMILES: CCOC(=O)C1=C(CC2CC(F)(F)C[C@H]2C(=O)O)NC(c2nccs2)=NC1C1CCCC1]

Step 7a.

A mixture of ethyl 3-oxobutanoate (0.4 g, 3 mmol), cyclopentanecarbaldehyde (0.38 g, 3 mmol), 1,3-thiazole-2-carboximidamide HCl salt (0.49 g, 3 mmol) and KOAc (0.59 g, 6 mmol) in CF3CH2OH (10 mL) was stirred for 24 hours at 90° C. After being cooled, it was partitioned (EtOAc-brine). The organic was dried (Na2SO4), filtered and concentrated. The residue was chromatographed (silica, ethyl acetate/petroleum ether) to give the desired compound as a yellow solid (0.33 g, 31%). ESIMS m/z=320.2 [M+H]+.

Step 7b.

Into a solution of the compound from step 7a (0.28 g, 0.88 mmol) in CCl4 (10 mL) was charged with NBS (156 mg, 0.88 mol) in portions at 0° C. over 30 minutes. The solution was stirred for 30 minutes at rt before being quenched with water and partitioned (CH2Cl2—H2O). The organic was dried (Na2SO4), filtered and concentrated. The residue was chromatographed (silica, ethyl acetate/petroleum ether) to give the desired compound as a yellow solid (0.15 g, 43%). ESIMS m/z=400.2, 402.2 [M+H]+.

Step 7c.

A solution of the compound from step 7b (130 mg, 0.33 mmol), (S)-4,4-difluoropyrrolidine-2-carboxylic acid (122.7 mg, 0.50 mmol), DIPEA (127.7 mg, 0.99 mmol) in 1,2-dichloroethane (5 mL) was stirred for 12 hours at rt. It was diluted with DCM (20 mL) and washed with aq NH4Cl and brine. The organic was dried (Na2SO4), filtered and concentrated. The residue was purified by Flash-Prep-HPLC (C18, MeCN/H2O) to give the title compound (mixture of diastereomers) as a yellow solid (35.6 mg, 25%). ESIMS m/z=469.25 [M+H]+. 1H NMR (400 MHz, CDCl3), δ1.23 (3H, t), 1.26-1.71 (8H, m), 2.02 (1H, s), 2.40 (1H, s), 2.68 (1H, s), 3.07 (1H, s), 3.34 (1H, s), 3.80 (1H, d), 3.93 (1H, d), 3.98-4.24 (3H, m), 4.51 (1H, s), 7.98 (2H, d).

Example 8

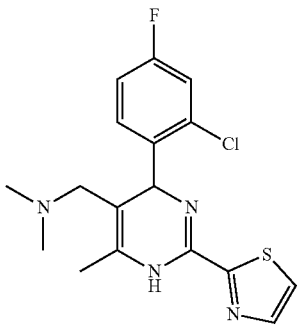 [SMILES: CC1=C(CN(C)C)C(c2ccc(F)cc2Cl)N=C(c2nccs2)N1]

Step 8a

A solution of compound from step 4d (200 mg, 0.49 mmol) in TFA (3 mL) was stirred for 2 hours at rt. it was concentrated and purified by Flash-Prep-HPLC (C18, MeCN/H$_2$O) to give the desired compound 57.5 mg (33.3%) as a yellow solid. ESIMS m/z=352.05, 354.05 [M+H]$^+$.

Step 8b.

A solution of compound from example 8a (1.0 g, 2.84 mmol), N,O-dimethyl-hydroxylamine hydrochloride (556 mg, 5.68 mmol), EDCI (813 mg, 4.26 mmol) and DIEPA (1.46 g, 11.36 mmol) in DCM (20 mL) was stirred for 2 hours at rt. The residue was extracted with DCM, washed with brine. The organic was dried (Na$_2$SO$_4$), filtered and concentrated to give the desired compound (1.02 g, 91%) as yellow solid. ESIMS m/z=395.00, 397.00 [M+H]$^+$. This material was used directly in next step without further purification.

Step 8c.

A solution of compound from step 8b (1.02 g, 2.78 mmol), (Boc)$_2$O (1.21 g, 5.57 mmol), and TEA (280 mg, 2.78 mmol), DMAP (339 mg, 2.78 mmol) in DCM (20 mL) was stirred for 1 hour at rt. The residue was extracted with EA. The mixture was washed with aqueous NH$_4$Cl and H$_2$O. The organic was dried (Na$_2$SO$_4$), filtered and concentrated. The residue was chromatographed (silica gel, ethyl acetate/petroleum ether) to give the desired compound (841 mg, 61.1%) as yellow solid. ESIMS m/z=495.15, 497.15 [M+H]$^+$.

Step 8d.

Into a solution of compound from step 8c (400 mg, 0.87 mmol) in THF (3 mL), was added LiAlH$_4$ (33.12 mg, 0.87 mmol) at −78° C. It was stirred for 0.5 hour at 0° C. before being quenched with H$_2$O (50 mL) and extracted with EtOAc. The organic layer was dried (Na$_2$SO$_4$), filtered and concentrated to give the desired compound (352 mg, 93%) as yellow solid. ESIMS m/z=436.00, 438.00 [M+H]$^+$.

Step 8e.

A solution of compound from step 8d (350 mg, 0.8 mmol) in TFA (3 mL) was stirred for 1 hour at rt and was concentrated. The residue was purified by Flash-Prep-HPLC (C18, MeCN/H$_2$O) to give the desired compound (180 mg, 67%) as yellow solid. ESIMS m/z=336.10, 338.10 [M+H]$^+$.

Step 8f.

A solution of compound from step 8e (100 mg, 0.30 mmol), dimethyl amine (1.19 ml, 2M in THF), NaBH(OAc)$_3$ (252 mg, 1.19 mmol) in THF (3 mL) was stirred for 2 hours at 40° C. The reaction was concentrated. The residue was purified by Flash-Prep-HPLC (C18, MeCN/H$_2$O) to give the title compound (racemic mixture) as yellow solid (67 mg, 62%). ESIMS m/z=365.00, 367.00[M+H]$^+$; $^1$H NMR (300 MHz, Methanol-d$_4$) δ 8.46 (s, 1H), 7.93 (d, 1H), 7.73 (d, 1H), 7.49 (dd, 1H), 7.29 (dd, 1H), 7.11 (td, 1H), 3.39-3.17 (m, 3H), 5.81 (s, 1H), 3.89 (ddd, 1H), 3.33 (d, 1H), 2.83 (d, 6H), 2.16 (s, 3H).

Example 9

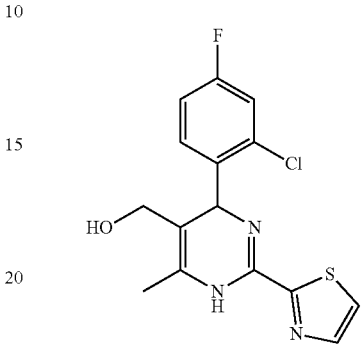

A mixture of compound from step 8e (35 mg, 0.1 mmol), NaBH$_4$ (15 mg, 0.41 mmol) in MeOH (2 mL) was stirred for 1 hour at rt. it was concentrated and the residue was purified by Flash-Prep-HPLC (C18, MeCN/H$_2$O) to give the title compound (racemic mixture) as a yellow solid (27.8 mg, 79%). ESIMS m/z=338.15, 340.15 [M+H]$^+$; $^1$H NMR (400 MHz, Methanol-d$_4$) δ 8.03-7.78 (m, 1H), 7.70 (d, 1H), 7.50 (t, 1H), 7.33-7.15 (m, 1H), 7.07 (t, 1H), 5.88 (s, 1H), 4.18 (d, 1H), 3.78 (d, 1H), 2.08 (s, 3H).

Example 10

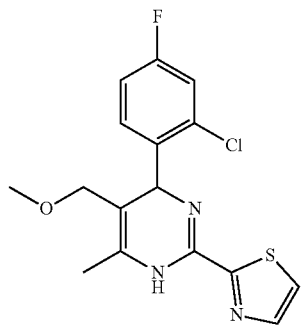 [SMILES: COCC1=C(C)NC(c2nccs2)=NC1c1ccc(F)cc1Cl]

Step 10a.

Into a solution of the compound from step 8d (0.25 g, 0.57 mmol) in EtOH (10 ML) was added NaBH$_4$ (0.021 g, 0.57 mmol) was added at rt and stirred 2 hours. It was quenched by addition of aq. NH$_4$Cl and partitioned (EtOAc/brine). The organic was dried (Na$_2$SO$_4$) and concentrated to give desired product (0.2 g, 80%) as yellow oil. This material was used in the next reaction directly without purification.

Step 10b.

Into a solution of compound from step 10a (0.2 g, 0.46 mmol) in DMF (10 mL) was charged with NaH (30 mg, 0.75 mol) at 0° C. The mixture was stirred for 30 minutes at 0° C. before MeI (53.3 mg, 0.38 mmol) was added. It was stirred for 30 minutes at rt before being quenched with water and partitioned (CH$_2$Cl$_2$—H$_2$O). The organic was dried (Na$_2$SO$_4$), filtered and concentrated. The residue was chromatographed (silica, ethyl acetate/petroleum ether) to give the desired compound as yellow oil (75 mg, 36%). ESIMS m/z=452.05, 454.05 [M+H]+.

Step 10b.

A solution of the compound from step 10a (60 mg, 0.58 mmol) in TFA (8 mL) and DCM (8 mL) was stirred for 2 hours at rt. It was concentrated and the residue was chromatographed (silica, ethyl acetate/petroleum ether) to give the title compound (racemic mixture) as a white solid (4.4 mg, 9.5%). ESIMS m/z=352.1, 354.1 [M+H]+; $^1$H NMR (400 MHz, methanol-d4), δ2.05 (3H, s), 3.21 (3H, s), 3.69 (1H, d), 4.00 (1H, d), 5.77 (1H, s), 7.06 (1H, td), 7.21 (1H, dd), 7.49 (1H, dd), 7.70 (1H, d), 7.90 (1H, d).

Example 11

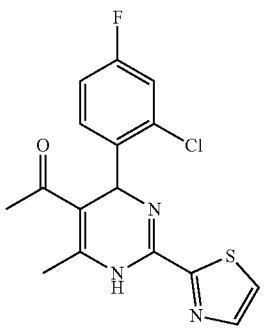 [SMILES: CC(=O)C1=C(C)NC(c2nccs2)=NC1c1ccc(F)cc1Cl]

A solution of pentane-2,4-dione (310 mg, 3.05 mmol), 2-chloro-4-fluorobenzaldehyde (485 mg, 3.05 mmol), thiazole-2-carboximidamide hydrochloride (500 mg, 3.05 mmol), KOAc (600 mg, 6.098 mmol) in $CF_3CH_2OH$ (10 mL) was stirred for 16 hours at 90° C. The mixture was cooled, quenched by water and partitioned (EtOAc-brine). The organic was dried ($Na_2SO_4$), filtered and concentrated. The residue was chromatographed (silica, ethyl acetate/petroleum ether) to give the title compound (racemic mixture) as a yellow solid (220 mg, 21%). ESIMS m/z=350.00, 352.00 [M+H]+; $^1$H NMR (300 MHz, DMSO-$d_6$) δ: 2.08 (s, 3H), 3.47-3.50 (m, 3H), 6.04 (s, 1H), 6.99-7.26 (m, 1H), 7.26-7.38 (m, 1H), 7.39-7.51 (m, 1H), 7.83-8.14 (m, 2H).

Example 12

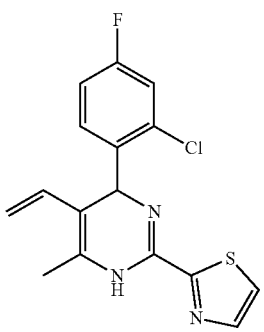 [SMILES: C=CC1=C(C)NC(c2nccs2)=NC1c1ccc(F)cc1Cl]

Step 12a.

To the solution of compound from example 11 (200 mg, 0.57 mmol) in MeOH (5 mL) was added $NaBH_4$ (86.8 mg, 2.28 mmol) portion wise. The mixture was stirred for 1 hour at rt. it was concentrated and the residue was purified by Flash-Prep-HPLC to give the desired compound as a yellow solid (40 mg, 20%) ESIMS m/z=352.15 [M+H]+.

Step 12b.

A mixture of compound from step 12a (25 mg, 0.07 mmol) in TFA (1 mL) was stirred for 1 hour at rt. it was concentrated and the residue was purified by Flash-Prep-HPLC (C18, MeCN/$H_2O$) to give the title compound (racemic mixture) as a yellow solid (5.3 mg, 22.7%); NMR showed a mixture of two unidentified olefinic isomers or tautomers of the title compound with a minor unknown impurity. ESIMS m/z=334.15, 334.15 [M+H]+.

Example 13

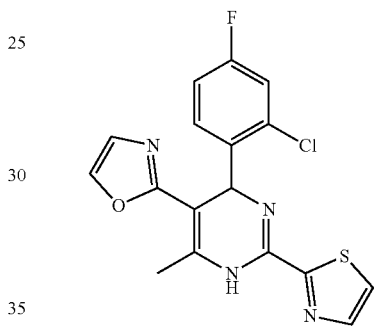

Step 13a.

A mixture of 3-oxobutanamide (3 g, 29 mmol), 2-chloro-4-fluorobenzaldehyde (4.9 g, 29 mmol), 1,3-thiazole-2-carboximidamide HCl salt (5 g, 29 mmol) and KOAc (6 g, 58 mmol) in $CF_3CH_2OH$ (50 mL) was stirred for 24 hours at 90° C. After being cooled, it was concentrated and partitioned (EtOAc-brine). The organic was dried ($Na_2SO_4$), filtered and concentrated. The residue was chromatographed (silica, ethyl acetate/petroleum ether) to give the desired compound as a yellow solid (1.2 g, 21%). ESIMS m/z=350.95, 352.95 [M+H]+.

Step 13b.

A solution of the compound from step 13a (0.2 g, 0.57 mmol), 1,3-dioxol-2-one (49 mg, 0.57 mmol) in polyphosphoric acid (10 mL) was stirred for 3 hours at 170° C. After being cooled, it was diluted with DCM (20 mL) and washed with brine. The organic layer was dried ($Na_2SO_4$), filtered and concentrated. The residue was purified by Flash-Prep-HPLC (C18, MeCN/$H_2O$) to give the title compound (racemic mixture) as a yellow solid (38 mg, 18%). ESIMS m/z=375.15, 377.15 [M+H]+.

Alternatively, this title compound was prepared by reacting the compound from step 20d and 2-(tributylstannyl)oxazole by following the similar procedure described in step 33a and 33b.

Example 13a

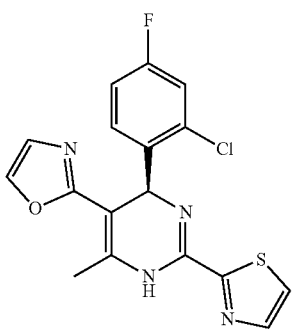 [SMILES: CC1=C(c2ncco2)[C@@H](c2ccc(F)cc2Cl)N=C(c2nccs2)N1]

The title compound was obtained through SFC (R,R-WHELK-O1) chiral separation of the example 13. Rt=6.51 minutes. ESIMS m/z=375.20, 377.20 [M+H]$^+$.

Example 13b

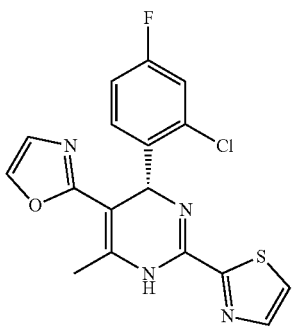 [SMILES: CC1=C(c2ncco2)[C@H](c2ccc(F)cc2Cl)N=C(c2nccs2)N1]

The title compound was obtained through SFC (R,R-WHELK-O1) chiral separation of the example 13. Rt=7.59 minutes. ESIMS m/z=375.15, 377.15 [M+H]$^+$;

Example 14

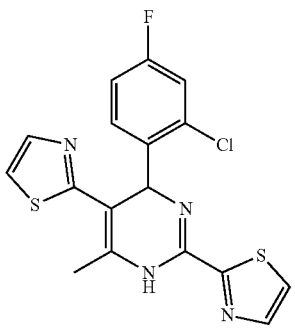 [SMILES: CC1=C(c2nccs2)C(c2ccc(F)cc2Cl)N=C(c2nccs2)N1]

Step 14a.

A mixture of compound from step 13a (1 g, 2.85 mmol), di-tert-butyl dicarbonate (0.62 g, 2.85 mmol) and DMAP (0.17 g, 1.43 mmol) in DCM (20 mL) was stirred for 24 hours at rt. It was concentrated and partitioned (DCM-brine). The organic was dried (Na$_2$SO$_4$), filtered and concentrated. The residue was chromatographed (silica, ethyl acetate/petroleum ether) to give the desired compound as an yellow oil (0.5 g, 39%). ESIMS m/z=451.3, 453.3[M+H]$^+$.

Step 14b.

Into a solution of the compound from step 14a (0.6 g, 1.33 mmol) in THF (10 mL) was charged with Lawesson reagent (324.9 mg, 0.8 mol) in portions at 0° C. over 5 minutes. The solution was stirred for 2 days at rt. The reaction was quenched with water, partitioned (CH$_2$Cl$_2$—H$_2$O). The organic was dried (Na$_2$SO$_4$), filtered and concentrated. The residue was chromatographed (silica, ethyl acetate/petroleum ether) to give the desired compound as a yellow solid (0.16 g, 26%). ESIMS m/z=467.15, 469.15 [M+H]$^+$.

Step 14c.

A solution of the compound from step 14b (160 mg, 0.34 mmol), 2-bromo-1,1-diethoxyethane (84.71 mg, 0.43 mmol) and PTSA (5.2 mg, 0.03 mmol) in HOAc (5 mL) was stirred for 2 hours at 170° C. It was concentrated and the residue was partitioned (DCM-brine). The organic was dried (Na$_2$SO$_4$), filtered and concentrated. The residue was purified by Flash-Prep-HPLC (C18, MeCN/H$_2$O) to give the title compound (racemic mixture) as a yellow solid (42.5 mg, 32%). ESIMS m/z=390.95, 392.95 [M+H]$^+$; $^1$H NMR (400 MHz, methanol-d4), δ2.49 (3H, s), 6.30 (1H, s), 7.02 (1H, t), 7.19-7.30 (1H, m), 7.39-7.51 (2H, m), 7.68-7.77 (2H, m), 7.88-8.01 (1H, m).

Example 15

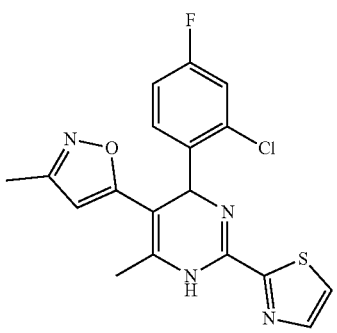 [SMILES: CC1=C(c2cc(C)no2)C(c2ccc(F)cc2Cl)N=C(c2nccs2)N1]

Step 15a.

To a solution of acetone (174 mg, 3 mmol) in THF (5 mL) was added LDA (1.5 mL, 2M in THF) at −78° C. and stirred for 0.5 hour. The compound from example 11 (436 mg, 1 mmol) in THF (5 mL) was added dropwise. The mixture was stirred for 1 hour at 0° C. before being quenched with water. The mixture was extracted with DCM, washed with brine. The organic was dried (Na$_2$SO$_4$), filtered and concentrated to give the desired compound as yellow solid (142 mg, 29.8%). ESIMS m/z=476.00, 478.00 [M+H]$^+$. This material was used directly in the next step without further purification.

Step 15b.

A solution of compound from step 15a (142 mg, 0.3 mmol), hydroxylamine (62 mg, 0.9 mmol) and pyridine (95 mg, 1.2 mmol) in EtOH (4 mL) was stirred for 18 hours at 80° C. After cooled, the reaction was diluted with EtOAc and washed with brine. The organic layer was dried (Na$_2$SO$_4$), filtered and concentrated to give the desired compound as yellow oil (152 mg, 103%). ESIMS m/z=491.05, 493.05 [M+H]$^+$. This material was used directly in the next step without further purification.

Step 15c.

A solution of compound from step 15b (152 mg, 0.31 mmol), NaHCO$_3$ (1 g), KI (154 mg, 0.92 mmol), 12 (78.7 mg, 0.31 mmol) in H$_2$O (2 mL) and THF (2 mL) was stirred for 4 hours at 100° C. After cooling to rt, the reaction was concentrated. The residue was extracted with DCM and washed with brine. The organic layer was dried (Na$_2$SO$_4$), filtered and concentrated. The residue was chromatographed (silica, ethyl acetate/petroleum ether) to give the desired compound 66 mg (43.5%) as yellow solid. ESIMS m/z=489.20, 491.20 [M+H]$^+$.

Step 15d.

A solution of compound from step 15c (66 mg, 0.8 mmol) in TFA (1 mL) and DCM (1 mL) was stirred for 1 hour at rt. The solvent was concentrated. The residue was purified by Flash-Prep-HPLC (C18, MeCN/H$_2$O) to give the title compound (racemic mixture) as yellow solid (14.4 mg, 27.4%). ESIMS m/z=389.20, 391.20 [M+H]$^+$; $^1$H NMR (400 MHz, Methanol-d$_4$) δ 7.93 (d, 1H), 7.72 (s, 1H), 7.48 (t, 1H), 7.26 (d, 1H), 7.05 (td, 1H), 6.09 (s, 1H), 5.95 (s, 1H), 2.43 (s, 3H), 2.22 (s, 3H).

Example 16

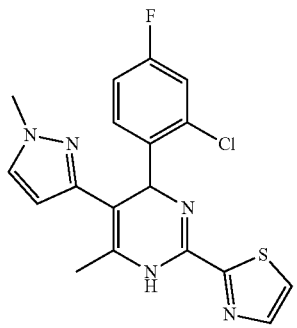 [SMILES: CC1=C(c2ccn(C)n2)[C@H](c2ccc(F)cc2Cl)N=C(c2nccs2)N1]

Step 16a.

To a solution of example 11 (g, 2.86 mmol) in DCM (10 mL) was added (Boc)$_2$O (1.25 g, 5.71 mmol), DMAP (1.75 g, 1.43 mmol) and TEA (600 mg, 5.71 mmol). It was stirred for 30 minutes at r.t before being quenched by water and partitioned (DCM-brine). The organic was dried (Na$_2$SO$_4$), filtered and concentrated. The residue was chromatographed (silica, ethyl acetate/petroleum ether) to give the desire compound as yellow solid (900 mg, 70%). ESIMS m/z=450.10, 452.10 [M+H]$^+$.

Step 16b.

Into the solution of compound from step 16a (300 mg, 0.667 mmol) in toluene (5 ml) was added DMF-DMA (250 mg, 2.00 mmol). It was stirred for 16 hours at 115° C. After cooled, it was concentrated and diluted by H$_2$O and partitioned (EtOAc-brine). The organic was dried (Na$_2$SO$_4$), filtered and concentrated. The residue was chromatographed (silica, ethyl acetate/petroleum ether) to give the desire compound as a grey solid (150 mg, 45%). ESIMS m/z=505.14, 507.14 [M+H]$^+$.

Step 16c.

To a solution of compound from step 16b (150 mg, 0.279 mmol) in EtOH (5 ml) was added methylhydrazine*sulfuric acid (61 mg, 0.42 mmol). The mixture was stirred for 16 hours at 80° C. It was cooled, quenched by water and partitioned (EtOAc-brine). The organic was dried (Na$_2$SO$_4$), filtered and concentrated. The residue was chromatographed (silica, ethyl acetate/petroleum ether) to give the desire compounds (two regio-isomers) as a yellow solid (120 mg, 83%). ESIMS m/z=488.12, 490.12 [M+H]$^+$.

Step 16d.

To a solution of compound from step 16c (120 mg, 0.25 mmol) in DCM (5 mL) was added TFA (5 mL). The solution was stirred for 1 hour at r.t before it was quenched by water and partitioned (EtOAc-brine). The organic was dried (Na$_2$SO$_4$), filtered and concentrated. The residue was Flash-Prep-HPLC (Cis, MeCN/H$_2$O) to give the title compound (racemic mixture) as a yellow solid (8.2 mg, 8.6%). ESIMS m/z=388.05, 390.05 [M+H]$^+$; $^1$H NMR (300 MHz, CDCl$_3$, ppm): 1.81 (s, 3H), 1.90 (s, 1H), 3.63 (s, 3H), 3.25-3.30 (m, 1H), 3.72 (s, 1H), 5.65-5.80 (m, 2H), 5.80-5.97 (m, 1H), 6.90-7.10 (m, 3H), 7.30-7.40 (m, 1H), 7.40-7.50 (m, 1H), 7.50-7.52 (m, 1H), 7.56-7.68 (m, 1H), 7.68-7.77 (m, 1H), 7.80-7.93 (m, 1H).

Alternatively, this title compound was prepared by reacting of the compound from step 20d and 1-methyl-2-(tributylstannyl)-1H-imidazole by following the similar procedure described in step 33a and 33b.

Example 16a

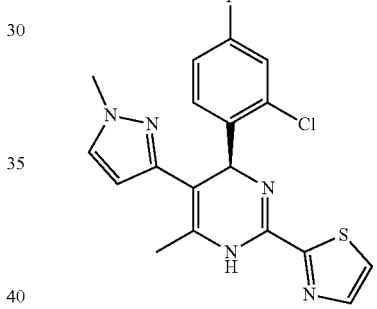

This title compound was obtained through SFC (chiral pack IC-3) chiral separation of the example 16. Rt=1.54 minutes. ESIMS m/z=388.00, 390.00 [M+H]$^+$.

Example 16b

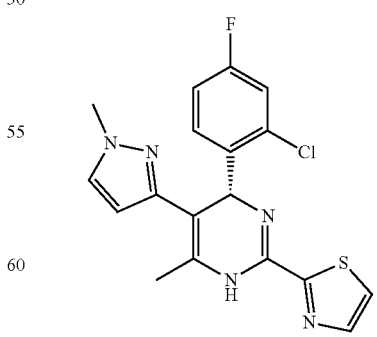

This title compound was obtained through SFC (chiral pack IC-3) chiral separation of the example 16. Rt=2.23 minutes. ESIMS m/z=388.00, 390.10, [M+H]$^+$.

Example 17

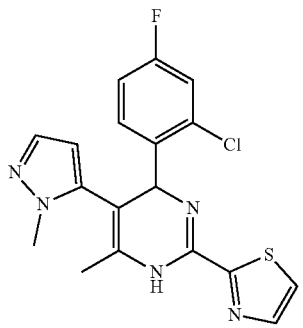 [SMILES: CC1=C(c2ccnn2C)C(c2ccc(F)cc2Cl)N=C(c2nccs2)N1]

The title compound (racemic mixture) was isolated from step 16d as a yellow solid (26.6 mg, 28%). ESIMS m/z=388.00, 390.00 [M+H]+. 1H NMR (300 MHz, CDCl3, ppm): δ 1.81 (s, 3H), 1.90 (s, 1H), 3.63 (s, 3H), 3.25-3.30 (m, 1H), 3.72 (s, 1H), 5.65-5.80 (m, 2H), 5.80-5.97 (m, 1H), 6.90-7.10 (m, 3H), 7.30-7.40 (m, 1H), 7.40-7.50 (m, 1H), 7.50-7.52 (m, 1H), 7.56-7.68 (m, 1H), 7.68-7.77 (m, 1H), 7.80-7.93 (m, 1H).

Example 18

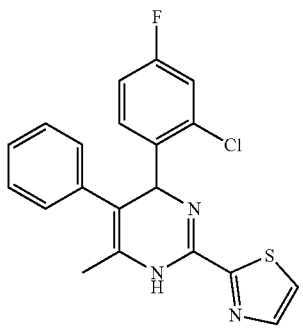 [SMILES: CC1=C(c2ccccc2)C(c2ccc(F)cc2Cl)N=C(c2nccs2)N1]

Step 18a.

A solution of 1-phenylpropan-2-one (486 mg, 3.63 mmol), 2-chloro-4-fluorobenzaldehyde (577 mg, 3.63 mmol) and H2SO4 (0.1 mL) in HOAc (5 mL) was stirred for 14 hours at rt. The solution was diluted with EtOAc, washed with H2O, brine and concentrated. The residue was chromatographed (silica, petroleum ether/ethyl acetate) to give the desired compound as yellow oil (320 mg, 32%). ESIMS m/z=275.15, 277.15 [M+H]+.

Step 18b.

A mixture of the compound from step 18a (275 mg, 1.0 mmol), 1,3-thiazole-2carboximidamide HCl salt (164 mg, 1.0 mmol) and K2CO3 (138 mg, 1.0 mmol) in DMF (5 mL) in microwave tube was irradiated for 1 hour at 100° C. The mixture was partitioned (EtOAc-brine). The residue was chromatographed (silica, petroleum ether/ethyl acetate) to give the title compound (racemic mixture) as off-white solid (45 mg, 11.7%). ESIMS m/z=383.95, 385.95 [M+H]+; 1H NMR (400 MHz, DMSO), δ 1.83 (1H, s), 1.94 (1H, s), 5.84 (1H, s), 3.46-3.47 (2H, d), 7.04-7.06 (2H, m), 7.13-7.15 (4H, m), 7.18-7.20 (1H, m), 7.22-7.24 (1H, m), 7.29-7.32 (1H, m), 7.89-7.94 (1H, m), 9.31 (1H, s).

Example 19

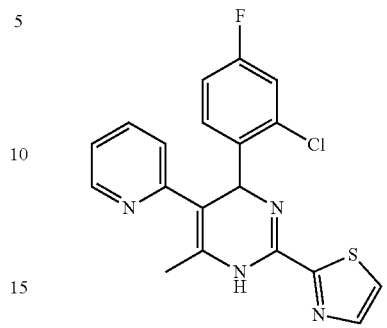

A mixture of methyl pyridin-2-ylmethyl ketone (98.5 mg, 0.73 mmol), 2-chloro-4-fluorobenzaldehyde (116 mg, 0.73 mmol), 1,3-thiazole-2-carboximidamide HCl salt (100 mg, 0.61 mmol) and KOAc (119.56 mg, 1.22 mmol) in CF3CH2OH (10 mL) was stirred for 18 hours at 90° C. After being cooled, it was concentrated and partitioned (EtOAc-brine). The organic was dried (Na2SO4), filtered and concentrated. The residue was purified by Flash-Prep-HPLC (C18, MeCN/H2O) to give the title compound (racemic mixture) as a yellow solid (61.6 mg, 26.2%) ESIMS m/z=385.10, 387.10 [M+H]+; 1H NMR (400 MHz, Methanol-d4) δ 8.48 (ddd, 1H), 7.95 (d, 1H), 7.75 (d, 1H), 7.71 (td, 1H), 7.59 (dd, 1H), 7.26-7.15 (m, 2H), 7.11 (dd, 1H), 7.05 (td, 1H), 6.24 (d, 1H), 2.07 (d, 3H).

Example 20

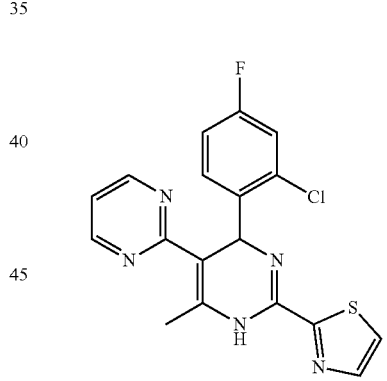

Step 20a.

A solution of thiazole-2-carboximidamide hydrochloride (3.0 g, 18.40 mmol), allyl 3-oxobutanoate (2.87 g, 20.24 mmol), 2-chloro-4-fluorobenzaldehyde (3.20 g, 20.24 mmol) and KOAc (3.61 g, 36.80 mmol) in CF3CH2OH (100 mL) was stirred for 14 hours at 80° C. The solution was diluted with EtOAc and washed with brine. The residue was chromatographed (silica, petroleum ether/ethyl acetate) to give the desired compound as yellow solid (5.0 g, 69%). ESIMS m/z=391.95, 393.95 [M+H]+.

Step 20b.

A mixture of the compound from step 20a (3.0 g, 7.67 mmol), (Boc)2O (1.84 g, 8.44 mmol), TEA (0.77 g, 7.67 mmol) and DMAP (187 mg, 1.53 mmol) in DCM (100 mL) was stirred for 14 hours at rt. The solution was diluted with DCM and washed with H2O, brine. The organic was dried (Na2SO4), filtered and concentrated. The residue was chromatographed (silica, petroleum ether/ethyl acetate) to give the desired compound as yellow solid (2.54 g, 67%). ESIMS m/z=492.20, 494.20 [M+H]+.

Step 20c.

A solution of the compound from step 20b (2.5 g, 5.09 mmol), morpholine (657 mg, 7.64 mmol), Pd(PPh$_3$)$_4$ (294 mg, 0.25 mmol) in THF (50 mL) was stirred for 2 hours at rt. The solution was diluted with EtOAc and washed with NaHCO$_3$ and brine. The organic was dried (Na$_2$SO$_4$), filtered and concentrated. The residue was chromatographed (silica, petroleum ether-ethyl acetate) to give the desired compound as yellow solid (2.23 g, 96%). ESIMS m/z=452.15, 454.15 [M+H]+.

Step 20d.

A mixture of compound from step 20c (150 mg, 0.33 mmol), pyridinium bromide perbromide (105 mg, 0.33 mmol), pyridine (26 mg, 0.33 mmol) in MeCN (4 mL) was stirred for 4 hours at rt. It was concentrated and the residue was partitioned (DCM-NH$_4$Cl). The organic was dried (Na$_2$SO$_4$) filtered and concentrated. The residue was chromatographed (silica, ethyl acetate/petroleum ether) to give the desired compound as a yellow solid (121 mg, 95%). ESIMS m/z=488.15, 490.15 [M+H]+.

Step 20e.

A mixture of compound from step 20d (500 mg, 1.033 mmol), 2-(tri-n-butylstannyl)-pyrimidine (395 mg, 1.03 mmol), CsF (313 mg, 2.06 mmol) and Pd(PPh$_3$)$_4$ (115.5 mg, 0.10 mmol), CuI (38 mg, 0.20 mmol) in DMF (7 mL) was stirred for 48 hours at 40° C. After being cooled to rt, it was concentrated and the residue was partitioned (EtOAc/brine). The organic was dried (Na$_2$SO$_4$), filtered and concentrated. The residue was chromatographed (silica, ethyl acetate/ petroleum ether) to give the desired compound as a yellow solid (300 mg, 60%). ESIMS m/z=486.25, 488.25 [M+H]+.

Step 20f.

A solution of compound from step 20e (100 mg, 2.3 mmol) in TFA (2 mL) and DCM (2 mL) was stirred for 2 hours at rt. The solution was concentrated. The residue was purified by Flash-Prep-HPLC (Cis, MeCN/H$_2$O) to give the title compound (racemic mixture) as a yellow solid (39.4 mg, 49.6%). ESIMS m/z=386.15, 388.15 [M+H]+; $^1$H NMR (300 MHz, Methanol-d$_4$) δ 8.63 (d, 2H), 7.93 (d, 1H), 7.72 (s, 1H), 7.45 (m, 1H), 7.18 (m, 2H), 6.95 (m, 1H), 6.54 (s, 1H), 2.56 (s, 3H).

Example 21

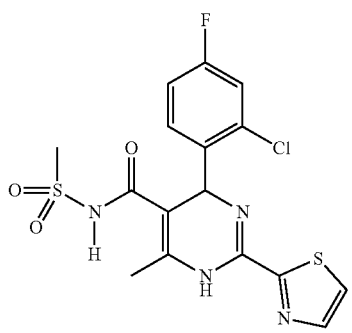 [SMILES: CC1=C(C(=O)NS(C)(=O)=O)C(c2ccc(F)cc2Cl)N=C(c2nccs2)N1]

Step 21a.

A mixture of compound from step 8d (300 mg, 0.69 mmol), Methanesulfonamide (65. mg, 0.69 mmol), PhI (OPiv)$_2$ (222 mg, 0.69 mmol), Rh$_2$(Esp)$_2$ (26.1 mg, 0.03 mmol) in t-BuOH (6 mL) was stirred for 3 hour at rt. it was concentrated and the residue was partitioned (EtOAc-brine). The organic was dried (Na$_2$SO$_4$), filtered and concentrated. The residue was chromatographed (silica, ethyl acetate/ petroleum ether) to give the desired compound as a yellow solid (286 mg, 78.3%). ESIMS m/z=529.1. 531.1 [M+H]+.

Step 21b.

A mixture of compound from step 21a (100 mg, 0.19 mmol), TFA (3 ml) in DCM (2 ml) was stirred for 1 hour at rt. it was concentrated and the residue was purified by Flash-Prep-HPLC (C18, MeCN/H$_2$O) to give the title compound (racemic mixture) as a yellow solid (34.9 mg, 42.8%). ESIMS m/z=429.10, 431.10 [M+H]+; $^1$H NMR (400 MHz, Methanol-d$_4$) δ 8.08-7.95 (m, 1H), 7.87 (d, 1H), 7.50 (dd, 1H), 7.27 (dd, 1H), 7.11 (td, 1H), 6.16 (d, 1H), 3.11 (s, 3H), 2.29 (d, 3H).

Example 22

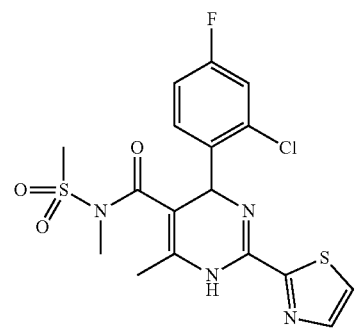 [SMILES: CC1=C(C(=O)N(C)S(C)(=O)=O)C(c2ccc(F)cc2Cl)N=C(c2nccs2)N1]

Step 22a.

A mixture of compound from step 21a (120 mg, 0.23 mmol), CH$_3$I (193 mg, 1.36 mmol), K$_2$CO$_3$ (127 mg, 0.92 mmol) in CH$_3$CN (3 mL) was stirred for 3 hours at 40° C. The mixture was concentrated and partitioned (DCM-brine). The organic was dried (Na$_2$SO$_4$) filtered and concentrated to give the desired compound as a yellow solid (120 mg, 96.7%) ESIMS m/z=543.20, 545.20 [M+H]+. This material was used directly in the next step without further purification.

Step 22b.

A mixture of compound from step 22a (100 mg, 0.19 mmol) in TFA (2 mL) and DCM (2 mL) was stirred for 1 hour at rt. It was concentrated. The residue was purified by Flash-Prep-HPLC (C18, MeCN/H$_2$O) to give the title compound (racemic mixture) as a yellow solid (34.9 mg, 80%). ESIMS m/z=443.15, 445.15 [M+H]+; $^1$H NMR (400 MHz, Methanol-d$_4$) δ 7.97 (d, 1H), 7.77 (d, 1H), 7.47 (m, 1H), 7.25 (m, 1H), 7.11 (m, 1H), 6.05 (s, 1H), 3.23 (s, 3H), 3.19 (s, 3H), 2.12 (s, 3H).

Example 23

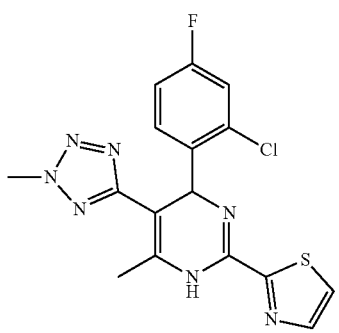 [SMILES: CC1=C(c2nnn(C)n2)C(c2ccc(F)cc2Cl)N=C(c2nccs2)N1]

Step 23a.
Into a solution of compound from step 13a (500 mg, 1.43 mmol) and Py (170 mg, 2.14 mmol) in DCM (10 ml) was added TFAA at 0° C. It was stirred for 4 hours at rt. The reaction was quenched by water and partitioned (DCM-brine). The organic was dried (Na$_2$SO$_4$), filtered and concentrated to give the desired compound as a red oil (500 mg, crude). ESIMS m/z=333.03, 335.03 [M+H]$^+$. This material was used in next step directly without further purification.

Step 23b.
To a solution of compound from step 23a (500 mg, 1.50 mmol), TEA (300 mg, 3.00 mmol) and DMAP (90 mg, 0.75 mmol) in DCM (10 ml) was added (Boc)$_2$O (655 mg, 3.00 mmol) in DCM (3 mL) dropwise. It was stirred for 16 hours at rt. before being quenched by water and partitioned (DCM-brine). The organic layer was dried (Na$_2$SO$_4$), filtered and concentrated. The residue was purified by Flash-Prep-HPLC (Cis, MeCN/H$_2$O) to give the desired compound as yellow solid (500 mg, 64%). ESIMS m/z=433.03, 435.03 [M+H]$^+$.

Step 23c.
The mixture of compound from step 23b (900 mg, 2.08 mmol), NaN$_3$ (350 mg, 5.41 mmol) and Et$_3$N. HCl (850 mg, 6.25 mmol) in toluene (5 mL) was stirred for 16 hour at 120° C. The mixture was quenched by water and partitioned (EtOAc-brine), the organic layer was dried (Na$_2$SO$_4$), filtered and concentrated. The residue was purified by Flash-Prep-HPLC (C18, MeCN/H$_2$O) to give the desired product as a yellow solid (900 mg, 91%). ESIMS m/z=476.10, 478.10 [M+H]$^+$.

Step 23d.
To the mixture of compound from step 23c (100 mg, 0.74 mmol) and K$_2$CO$_3$ (60 mg, 0.42 mmol) in MeCN (10 mL) was added iodomethane (40 mg, 0.25 mmol). The mixture was stirred for 2 hours at rt. It was quenched by water and partitioned (EtOAc-brine). The organic was dried (Na$_2$SO$_4$), filtered and concentrated. The residue was chromatographed (silica, ethyl acetate/petroleum ether) to give the desired mixture as an off-white solid (80 mg, 80%). ESIMS m/z=489.11, 491.11 [M+H]$^+$.

Step 23e.
A solution of compound from step 23d (80 mg, 0.16 mmol) in TFA (2 mL) and DCM (2 mL) was stirred for 30 minutes at rt. It was concentrated. The residue was diluted by water and partitioned (EtOAc-brine). The organic was dried (Na$_2$SO$_4$), filtered and concentrated. The residue was chromatographed (MeCN/H$_2$O) to give title compound (racemic mixture; tentatively assigned regio-isomer) as a white solid (27.0 mg, 42%). ESIMS m/z=390.10, 392.10 [M+H]$^+$; $^1$H NMR (300 MHz, CDCl$_3$, ppm): δ 2.63 (s, 3H), 4.27 (s, 3H), 6.40 (s, 1H), 6.80-6.95 (m, 1H), 7.10-7.20 (m, 1H), 7.30-7.40 (m, 1H), 7.43-7.52 (m, 1H), 7.84 (s, 1H).

Example 24

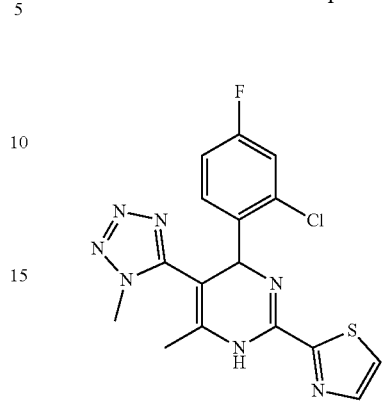

The title compound (racemic mixture; tentatively assigned regio-isomer) was isolated from step 23e as a white solid (2.4 mg, 4%), ESIMS m/z=390.05, 390.05 [M+H]$^+$; $^1$H NMR (300 MHz, CDCl$_3$, ppm): δ 1.90 (s, 3H), 3.81 (s, 3H), 6.02 (s, 1H), 6.90-7.11 (m, 2H), 7.43-7.51 (m, 1H), 7.51-7.59 (m, 1H), 7.82-7.95 (m, 1H).

Example 25

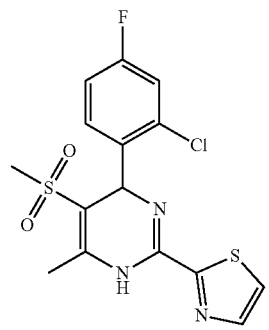 [SMILES: CC1=C(S(C)(=O)=O)C(c2ccc(F)cc2Cl)N=C(c2nccs2)N1]

Step 25a.
A mixture of 1-(methylsulfonyl)propan-2-one (0.5 g, 3.7 mmol), 2-chloro-4-fluorobenzaldehyde (0.59 g, 3.7 mmol), piperidine (0.05 mL) and HOAc (0.05 mL) in toluene (15 mL) was stirred for 24 hours at 120° C. After being cooled, it was concentrated and partitioned (EtOAc-brine). The organic was dried (Na$_2$SO$_4$), filtered and concentrated. The residue was chromatographed (silica, ethyl acetate/petroleum ether) to give the desired compound as yellow oil (0.2 g, 20%). ESIMS m/z=276.90, 278.90 [M+H]$^+$.

Step 25b.
A solution of the compound from step 25a (160 mg, 0.58 mmol) and 1,3-thiazole-2-carboximidamide HCl salt (95.12 mg, 0.58 mmol) in DMF (8 mL) was stirred for 24 hours at 80° C. After being cooled, it was concentrated and partitioned (EtOAc-brine). The organic was dried (Na$_2$SO$_4$), filtered and concentrated. The residue was chromatographed (silica, ethyl acetate/petroleum ether) to give the desired compound (racemic mixture) as a white solid (44.6 mg, 20%). ESIMS m/z=386.10, 388.10 [M+H]$^+$; $^1$H-NMR (300

MHz, DMSO): δ 10.00 (br, 1H), 2.90 (3H, s), 6.00 (1H, s), 7.25 (1H, td), 7.40-7.52 (2H, m), 7.96 (2H, dd), 10.24 (1H, s).

Example 26

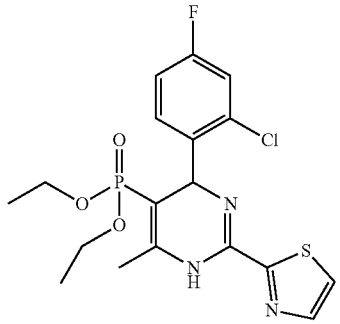 [SMILES: CCOP(=O)(OCC)C1=C(C)NC(c2nccs2)=NC1c1ccc(F)cc1Cl]

A solution of diethyl (2-oxopropyl)phosphonate (92 mg, 0.5 mmol), 2-chloro-4-fluorobenzaldehyde (79 mg, 0.5 mmol), thiazole-2-carboximidamide hydrochloride (82 mg, 0.5 mmol), KOAc (60 mg, 1.0 mmol) in EtOH (10 mL) was stirred for 16 hours at 60° C. The mixture was cooled, quenched by water and partitioned (EtOAc-brine). The organic was dried (Na$_2$SO$_4$), filtered and concentrated. The residue was chromatographed (silica, ethyl acetate/petroleum ether) to give the title compound (racemic mixture) as a yellow solid (45 mg, 20%). ESIMS m/z=444.07, 446.07 [M+H]$^+$; $^1$H NMR (500 MHz, DMSO-d 6) δ 9.92 (d, J=3.7 Hz, 1H), 7.94 (d, J=3.0 Hz, 1H), 7.87 (d, J=3.3 Hz, 1H), 7.39 (t, J=6.5 Hz, 2H), 7.20 (t, J=8.5 Hz, 1H), 5.68 (d, J=6.0 Hz, 1H), 3.85 (p, J=7.3 Hz, 2H), 3.71 (dq, J=14.2, 7.2, 6.8 Hz, 1H), 3.49 (h, J=7.7, 7.1 Hz, 1H), 2.35 (s, 3H), 1.17 (t, J=7.1 Hz, 3H), 0.88 (t, J=7.1 Hz, 3H).

Example 27

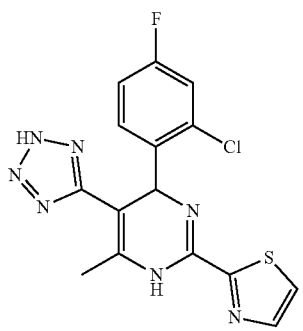 [SMILES: CC1=C(c2nn[nH]n2)C(c2ccc(F)cc2Cl)N=C(c2nccs2)N1]

The title compound was prepared from the compound of step 23c following similar procedure described in step 23e. ESIMS m/z=376.05, 378.05 [M+H]$^+$. $^1$H NMR (300 MHz, DMSO-d$_6$): δ 10.09 (s, 1H), 7.97 (d, 1H), 7.91 (d, 1H), 7.38 (m, 2H), 7.15 (dt, 1H), 6.12 (s, 1H), 2.19 (s, 3H).

Example 28

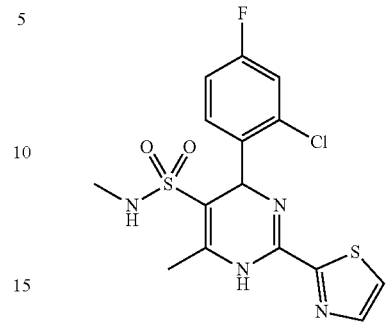

Step 28a.
Et$_3$N (1.4 mL, 10 mmol) was added into a solution of methylsulfamoyl chloride (1 g, 7.75 mmol) and trimethyl (prop-1-en-2-yloxy)silane (1 g, 8.52 mmol) in MeCN (20 mL) under 0° C. It was stirred for 5 hours at 90° C. before cooled. It was concentrated and purified by chromatograph (EtOAc/petroleum ether) to give the desired compound (330 mg, 28%) as brown oil. ESIMS m/z=152.03 [M+H]$^+$.

Step 28b.
A solution of compound form step 28a (330 mg, 2.19 mmol), Piperidine (cat.), AcOH (cat.) and 2-chloro-4-fluorobenzaldehyde (650 mg, 4.11 mmol) in toluene (10 ml) was stirred at 100° C. for overnight. The mixture was quenched by water and partitioned (EtOAc-brine). The organic was dried (Na$_2$SO$_4$), filtered and concentrated. The residue was chromatographed (MeCN/H$_2$O) to give the desire compound as yellow oil (250 mg, 39%). ESIMS m/z=292.15 [M+H]$^+$ Step 28c.
A solution of compound from step 28b (250 mg, 0.86 mmol), thiazole-2-carboximidamide hydrochloride salt (130 mg, 0.78 mmol) and K$_2$CO$_3$ (100 mg, 0.78 mmol) in DMF (5 mL) was stirred at 100° C. for 2 hours. The mixture was cooled and partitioned (EtOAc-brine). The organic was dried (Na$_2$SO$_4$), filtered and concentrated. The residue was purified by Flash-Prep-HPLC (MeCN/water) to give the title compound as a yellow solid (77.7 mg, 23%). ESIMS m/z=434.03 436.03[M+H]$^+$;

$^1$H NMR (300 MHz, DMSO-d$_6$): δ 10.09 (s, 1H), 7.97 (m, 1H), 7.91 (m, 1H), 7.39 (m, 2H), 7.21 (m, 1H), 7.06 (m, 1H), 5.86 (m, 1H), 2.43 (s, 3H), 2.34 (m, 3H).

Example 29

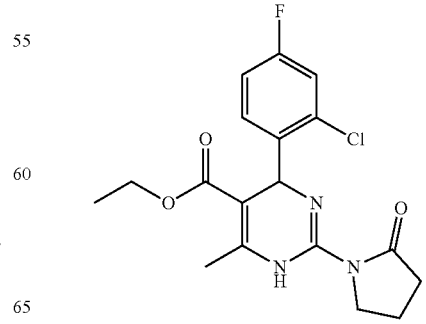

Step 29a.

A mixture of 2-chloro-4-fluorobenzaldehyde (500 mg, 3.16 mmol), ethyl 3-oxobutanoate (452.4 mg, 3.48 mmol), piperidine (0.02 mL) and HOAc (0.02 mL) in toluene (11 mL) was stirred for 24 hours at 120° C. before being cooled. It was concentrated and partitioned (EtOAc-brine). The organic was dried (Na$_2$SO$_4$), filtered and concentrated. The residue was chromatographed (silica, ethyl acetate/petroleum ether) to give the desired compound as yellow oil (270 mg, 32%). ESIMS m/z=271.12 273.12[M+H]$^+$.

Step 29b.

A mixture of 4-guanidinobutanoic acid (300 mg, 2.07 mmol), thionyl chloride (1.22 g, 10.35 mmol) in toluene (10 mL) was stirred for 16 hours at 80° C. before being cooled. The reaction was diluted by EtOAc and filtered to give desired compound as a taupe solid (314 mg, 92.5%). ESIMS m/z=128.10 [M+H]$^+$. This material was used directly in next step without further purification.

Step 29c.

A mixture of compound step 29a (162.5 mg, 0.6 mmol), step 29b (100 mg, 0.6 mmol) in DMF (10 mL) was stirred for 16 hours at 100° C. before being cooled. It was concentrated and partitioned (EtOAc-brine). The organic was dried (Na$_2$SO$_4$), filtered and concentrated. The residue was chromatographed (silica, ethyl acetate/petroleum ether) to give the title compound as a light yellow solid (28.2 mg, 12.4%). ESIMS m/z=380.05, 382.05 [M+H]$^+$; $^1$H NMR (300 MHz, DMSO-d6), δ 9.49 (s, 1H), 7.26 (m, 1H), 7.12 (m, 1H), 6.95 (m, 1H), 5.95 (s, 1H), 4.08 (m, 2H), 3.86 (m, 2H), 2.66 (m, 2H), 2.45 (m, 3H), 2.05 (m, 2H), 1.12 (m, 3H).

Example 30

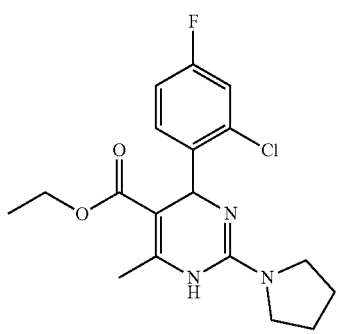 [SMILES: CCOC(=O)C1=C(C)NC(N2CCCC2)=NC1c1ccc(F)cc1Cl]

A mixture of compound step 29a (128.5 mg, 0.47 mmol), pyrrolidine-1-carboximidamide (100 mg, 0.47 mmol), K$_2$CO$_3$ (64.3 mg, 0.47 mmol) in DMF (10 mL) was stirred for 2 hours at 100° C. before being cooled. It was concentrated and partitioned (EtOAc-brine). The organic was dried (Na$_2$SO$_4$), filtered and concentrated. The residue was chromatographed (silica, ethyl acetate/petroleum ether) to give the title compound as an off-white solid (52 mg, 30.2%). ESIMS m/z=366.05, 368.05[M+H]$^+$; $^1$H NMR (300 MHz, DMSO-d6), δ 8.21 (s, 1H), 7.34 (m, 2H), 7.15 (m, 2H), 5.65 (s, 1H), 3.86 (m, 2H), 3.35 (m, 2H), 3.24 (m, 2H), 2.28 (m, 3H), 1.78 (m, 4H), 1.03 (m, 3H).

Example 31

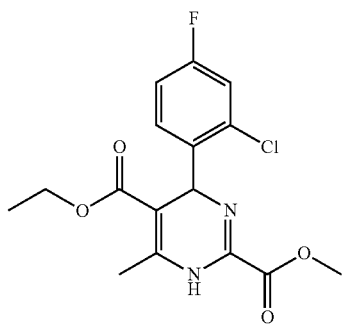 [SMILES: CCOC(=O)C1=C(C)NC(C(=O)OC)=NC1c1ccc(F)cc1Cl]

A mixture of compound step 29a (128.5 mg, 0.47 mmol), methyl 2-amino-2-iminoacetate (64.8 mg, 0.47 mmol), K$_2$CO$_3$ (65.3 mg, 0.47 mmol) in DMF (10 mL) was stirred for 2 hours at 100° C. before being cooled. It was concentrated and partitioned (EtOAc-brine). The organic was dried (Na$_2$SO$_4$), filtered and concentrated. The residue was chromatographed (silica, ethyl acetate/petroleum ether) to give the title compound as an off-white solid (60.2 mg, 36.1%). ESIMS m/z=355.15 357.15[M+H]$^+$; $^1$H NMR (300 MHz, DMSO-d6), δ 9.81 (s, 1H), 7.42 (m, 1H), 7.32 (m, 1H), 7.20 (m, 1H), 5.98 (s, 1H), 3.91 (m, 2H), 3.75 (m, 3H), 2.38 (m, 3H), 1.03 (m, 3H).

Example 32

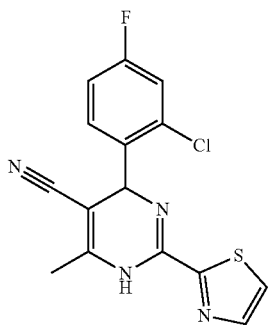 [SMILES: CC1=C(C#N)C(c2ccc(F)cc2Cl)N=C(c2nccs2)N1]

This title compound is the purified product of step 23a. ESIMS m/z=333.15, 335.15 [M+H]$^+$; $^1$H NMR (400 MHz, Methanol-d$_4$) δ 10.55 (s, 1H), 8.01 (d, 1H), 7.99 (d, 1H), 7.48 (m, 1H), 7.31 (m, 1H), 5.82 (s, 1H), 2.19 (s, 3H).

Example 33

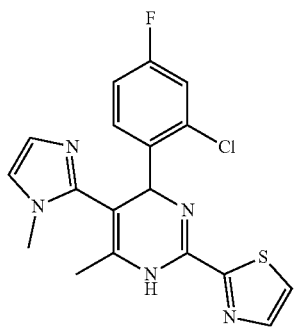

Step 33a.

A mixture of compound from step 20d (150 mg, 0.31 mmol), 1-methyl-2-(tributylstannyl)-1H-imidazole (229 mg, 0.62 mmol), Pd(PPh$_3$)$_4$ (34.6 mg, 0.03 mmol) in 1,4-dixane (3 mL) was irradiated in a microwave reactor for 1 hour at 140° C. before being cooled and concentrated. The residue was partitioned (DCM-NH$_4$Cl). The organic layer was dried (Na$_2$SO$_4$) filtered and concentrated. The residue was chromatographed (silica, ethyl acetate/petroleum ether) to give the desired compound as yellow solid (147 mg, 98%) ESIMS m/z=488.30, 490.30 [M+H]$^+$.

Step 33b.

A solution of compound from step 33a (147 mg, 0.3 mmol) in TFA/DCM (3 mL/3 mL) was stirred for 2 hours at rt before it was concentrated. The residue was purified by Flash (C$_{18}$ column, MeCN/H$_2$O) to give the title compound as yellow solid (55.4 mg, 47%) ESIMS m/z=388.05, 390.05 [M+H]$^+$; $^1$H NMR (400 MHz, Methanol-d$_4$) δ: 8.88 (s, 1H), 8.11 (d, 1H), 7.99 (d, 1H), 7.68 (m, 1H), 7.24 (m, 2H), 7.13 (s, 1H), 5.98 (d, 1H), 3.70 (s, 3H), 1.93 (d, 3H).

Example 34

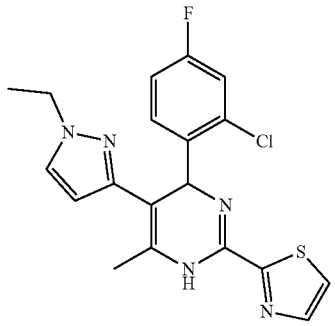 [SMILES: CCn1ccc(C2=C(C)NC(c3nccs3)=NC2c2ccc(F)cc2Cl)n1]

The title compound was prepared from the compound of step 20d and 1-ethyl-3-(tetramethyl-1,3,2-dioxaborolan-2-yl)-1H-pyrazole following similar procedure described in step 32a and 32b. ESIMS m/z=402.00, 404.00 [M+H]$^+$; $^1$H NMR (400 MHz, Methanol-d$_4$) δ: 7.94 (d, 1H), 7.76 (d, 1H), 7.52 (m, 2H), 7.19 (dd, 1H), 7.03 (m, 1H), 6.12 (d, 1H), 6.06 (d, 1H), 4.11 (q, 2H), 2.26 (d, 3H), 1.40 (t, 3H).

Example 35

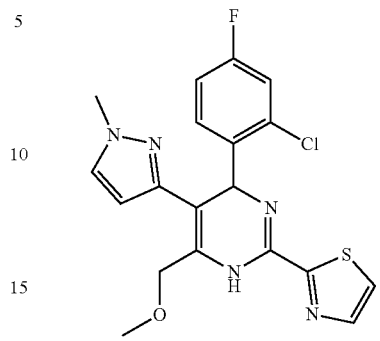

Step 35a.

A mixture of compounds from example 16 (2.23 g, 5.74 mmol) and NBS (1.02 g, 5.74 mmol) in DCM (100 mL) was stirred for 1 hour at 0° C. and additional 18 hours at rt. It was partitioned (DCM-H$_2$O). The organic phase was dried (Na$_2$SO$_4$), filtered and concentrated. The residue was chromatographed (C$_{18}$, column, MeCN/H$_2$O) to give the desired compound as yellow solid (1.62 g, 60.4%). ESIMS m/z=484.20, 468.20, 470.20 [M+H]$^+$.

Step 35b.

A mixture of compound from step 35b (100 mg, 0.21 mmol) and CH$_3$ONa/CH$_3$OH (1M, 0.3 mL) in CH$_3$OH (5 mL) was stirred for 1 hour at 0° C., It was partitioned (DCM-H$_2$O). The organic layer was dried (Na$_2$SO$_4$) filtered and concentrated. The residue was purified by Flash-Prep-HPLC (C$_{18}$ column, MeCN/H$_2$O) to give the title compound as yellow solid (5.8 mg, 6%) ESIMS m/z=418.00, 420.00 [M+H]$^+$; $^1$H NMR (400 MHz, Methanol-d$_4$) δ: 8.57 (s, 1H), 7.92 (d, 1H), 7.73 (d, 1H), 7.55 (t, 1H), 7.47 (d, 1H), 7.21 (m, 1H), 7.03 (t, 1H), 6.13 (d, 2H), 4.51 (s, 2H), 3.84 (s, 2H), 3.46 (s, 3H).

Example 36

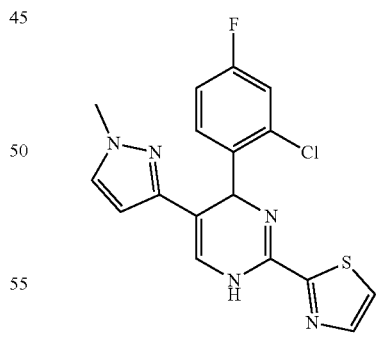

Step 36a.

A solution of ethyl 3-oxopropanoate (2.0 g, 17.2 mmol) in AcOH (30 mL) was added dropwise to the mixture of CeCl$_3$.7H$_2$O (1.3 g, 3.45 mmol) in MeOH (20 mL) and AcOH (20 mL) at room temperature. After stirring 0.5 hour, 2-chloro-4-fluorobenzaldehyde (5.4 g, 34.5 mmol) in AcOH (30 mL) was added dropwise. The mixture was stirred for 2 hours at 60° C. It was concentrated and partitioned (DCM-water). The organic was dried (Na$_2$SO$_4$), filtered and concentrated to give the desired compound as a yellow solid (1.6 g, 36%). ESIMS m/z=257.05, 259.05 [M+H]+.

Step 36b.

The mixture of compound from step 1a (1.6 g, 6.13 mmol), thiazole-2-carboximidamide hydrochloride (1.0 g, 6.13 mmol) and K$_2$CO$_3$ (2.1 g, 15.3 mmol) in DMF (50 mL) was stirred for 2 hours at 90° C. The solvent was removed in vacuum. The residue was purified by Flash-Prep-HPLC (C18, MeCN/water) to give the desired compound as yellow solid (1.0 g, 45%). ESIMS m/z=366.20, 368.20 [M+H]+.

Step 36c.

To a solution of step 36b (900 mg, 2.46 mmol), (Boc)$_2$O (804 mg, 3.69 mmol) and DMAP (30 mg, 0.246 mmol) in DCM (30 mL) was added Et$_3$N (497 mg, 4.92 mmol) slowly. The mixture was stirred for 16 hours at rt. It was concentrated and the residue was chromatographed (silica, ethyl acetate/petroleum ether) to give the desired compound as yellow solid (1.0 g, 88%). ESIMS m/z=466.30, 468.30 [M+H]+.

Step 36d.

To solution of step 36c (500 mg, 1.07 mmol) in EtOH (20 mL) was added NaOH (1M, 2.1 ml). The mixture was stirred for 16 hours at rt. The solvent was concentrated and the residue was purified by Flash-Prep-HPLC (C18, MeCN/water) to give the desired compound as yellow solid (200 mg, 43%). ESIMS m/z=438.10, 440.10 [M+H]+.

Step 36e.

To the solution of step 36d (100 mg, 0.228 mmol) and Pyridinium tribromide (86 mg, 0.274 mmol) in MeCN (10 mL) was added pyridine (18 mg, 0.228 mmol). The mixture was stirred for 3 hours at rt. It was concentrated, and the residue was chromatographed (silica, ethyl acetate/petroleum ether) to give the desired compound as yellow solid (60 mg, 56%). ESIMS m/z=472.00, 474.00 [M+H]+.

Step 36f.

A solution of step 36e (80 mg, 0.169 mmol), 1-methyl-3-(tributylstannyl)-1H-pyrazole (63 mg, 39 mmol) and Pd(PPh$_3$)$_4$ (39 mg, 0.034 mmol) in dioxane (2 mL) was irradiated in a microwave reactor for 1 hour at 140° C. It was concentrated. The residue was chromatographed (silica, ethyl acetate/petroleum ether) to give the desired compound as yellow solid (60 mg, 75%). ESIMS m/z=474.00, 476.00 [M+H]+.

Step 36g.

A solution of step 36f (55 mg, 0.116 mmol) in dioxane-HCl (10 mL) was stirred for 2 hours at rt. It was concentrated. The residue was purified by Flash-Prep-HPLC(C18, MeCN/water) to give the title compound as yellow solid (10.1 mg, 24%). ESIMS m/z=374.00, 376.00 [M+H]+; $^1$H NMR (300 MHz, DMSO-d$_6$): δ 9.20 (m, 1H), 7.90 (m, 2H), 7.55 (m, 1H), 7.30 (m, 4H), 6.30 (m, 1H), 6.10 (m, 1H), 3.84 (d, 3H).

Example 37

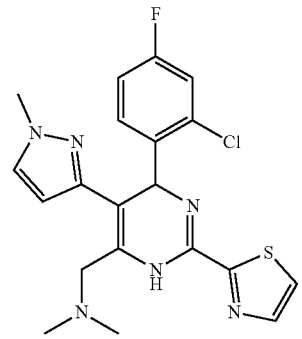 [SMILES: CN(C)CC1=C(c2ccn(C)n2)C(c2ccc(F)cc2Cl)N=C(c2nccs2)N1]

A mixture of compound from 35a (30 mg, 0.06 mmol), dimethylamine (0.12 mL, 0.12 mmol) and DIPEA (24.7 mg, 0.19 mmol) in DCM (2 mL) was stirred for 1 hour at 0° C. It was partitioned (DCM-H$_2$O). The organic phase was dried (Na$_2$SO$_4$), filtered and concentrated. The residue was purified by prep-HPLC (C$_{18}$ column, MeCN/H$_2$O) to give the title product as yellow solid (6.6 mg 24%) ESIMS m/z=431.10, 433.10 [M+H]+.

Example 38

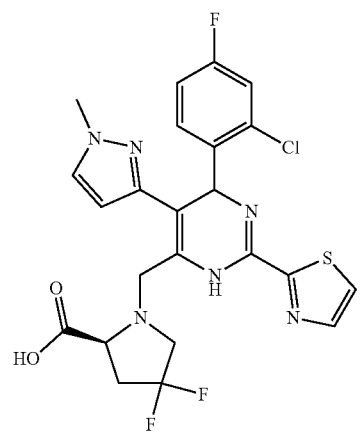 [SMILES: Cn1ccc(C2=C(CN3CC(F)(F)C[C@H]3C(=O)O)NC(c3nccs3)=NC2c2ccc(F)cc2Cl)n1]

A mixture of compound from step 35a (120 mg, 0.257 mmol), DIPEA (100 mg) and (S)-4,4-difluoropyrrolidine-2-carboxylic acid (50 mg, 0.308 mmol) in DCM (10 mL) was stirred for 1 hour at rt. The mixture was concentrated. The residue was purified by prep-HPLC (C$_{18}$ column, MeCN/H$_2$O) to give the title compound as yellow solid (30.1 mg, 24%). ESIMS m/z=537.20 [M+H]+; $^1$H NMR (300 MHz, DMSO-d$_6$) δ: 8.34 (s, 1H), 7.97 (m, 1H), 7.87 (m, 1H), 7.55 (m, 1H), 7.41 (m, 2H), 7.17 (m, 1H), 6.00 (m, 2H), 3.97 (m, 2H), 3.75 (s, 3H), 3.41 (m, 2H), 2.91 (m, 2H), 2.35 (m, 1H).

Example 39

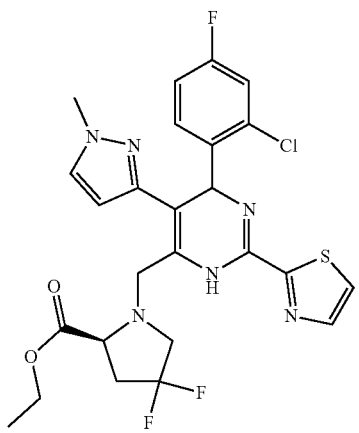 [SMILES: CCOC(=O)[C@@H]1CC(F)(F)CN1CC1=C(c2ccn(C)n2)C(c2ccc(F)cc2Cl)N=C(c2nccs2)N1]

A mixture of example 38 (25 mg, 0.047 mmol), ethanol (2.2 mg, 0.047 mmol), EDCI (18.05 mg, 0.094 mmol) and DMAP (17.2 mg, 0.141 mmol) in DCM (10 mL) was stirred for 4 hours at rt. It was concentrated. The residue was chromatographed (silica, DCM/MeOH) to give the title compound as yellow solid (14.8 mg, 56.3%). ESIMS m/z=565.30, 567.30 [M+H]$^+$. $^1$H NMR (300 MHz, DMSO-d6) δ: 8.34 (s, 1H), 7.97 (m, 1H), 7.87 (m, 1H), 7.55 (m, 1H), 7.41 (m, 2H), 7.17 (m, 1H), 6.00 (m, 2H), 3.97 (m, 2H), 3.75 (s, 3H), 3.41 (m, 2H), 2.91 (m, 2H), 2.35 (m, 1H).

Example 40

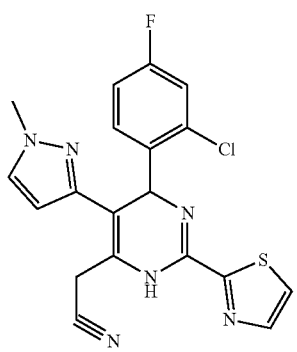 [SMILES: Cn1ccc(C2=C(CC#N)NC(c3nccs3)=NC2c2ccc(F)cc2Cl)n1]

A mixture of compound from step 35a (100 mg, 0.21 mmol), NaCN (13 mg, 0.27 mmol) in DMF (10 mL) was stirred for 3 hour at room temperature. It was diluted with EtOAc (20 mL) and washed with brine. The organic layer was dried (Na$_2$SO$_4$), filtered and concentrated. The residue was purified by prep-HPLC (MeCN/H2O, 0.1% NH$_4$CO$_3$) to give the title compound as white solid (6.5 mg, 7.37%). ESIMS m/z=413.10, 415.10[M+H]$^+$. $^1$H NMR (300 MHz, DMSO-d$_6$), δ8.89 (s, 1H), 7.96 (m, 2H), 7.91 (m, 1H), 7.63 (m, 2H), 7.42 (m, 1H), 6.16 (d, 1H), 6.01 (m, 2H), 4.11 (m, 2H), 3.80 (s, 3H).

Example 41

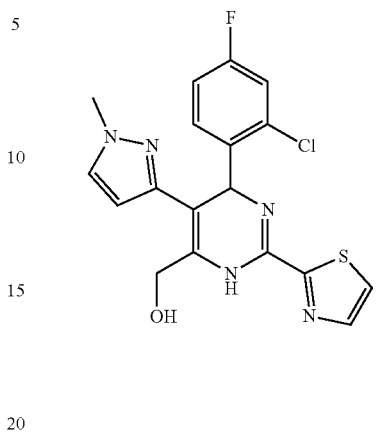

A mixture of compound from of step 35a (300 mg, 0.64 mmol), CF$_3$COOAg (155.8 mg, 0.70 mmol) in acetone/water (9 mL/3 mL) was stirred for 3 hours at 50° C. It was partitioned (DCM-H$_2$O). The organic phase was dried (Na$_2$SO$_4$) filtered and concentrated. The residue was purified by Flash (C$_{18}$ column, MeCN/H$_2$O) to give the title compound as yellow solid (11.8 mg, 5%) ESIMS m/z=404.00, 406.00 [M+H]$^+$; $^1$H NMR (300 MHz, DMSO-d$_6$) δ: 8.85 (s, 1H), 7.95 (d, 1H), 7.88 (d, 1H), 7.55 (d, 1H), 7.48 (m, 2H), 7.13 (m, 1H), 6.04 (s, 1H), 5.97 (d, 1H), 5.60 (t, 1H), 4.63 (m, 2H), 3.75 (s, 3H).

Example 42

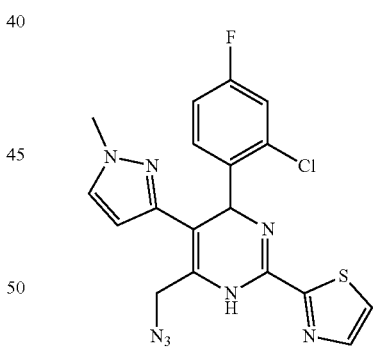

A mixture of step 35a (120 mg, 0.26 mmol) and sodium azide (34 mg, 0.52 mmol) in DMF (2 mL) was stirred for 1 hour at rt. It was partitioned (EtOAc-brine). The organic layer was dried (Na$_2$SO$_4$), filtered and concentrated. The residue was chromatographed (C$_{18}$ column, MeCN/water) to give the title compound as yellow solid (7.5 mg, 6.7%). ESIMS m/z=429.15, 431.15 [M+H]$^+$; $^1$H NMR (300 MHz, DMSO-d$_6$): δ 7.86 (s, 1H), 7.46 (m, 2H), 7.26 (m, 1H), 7.14 (m, 1H), 6.92 (m, 1H), 6.10 (d, 2H) 4.50 (br, 2H), 3.88 (s, 3H).

Example 43

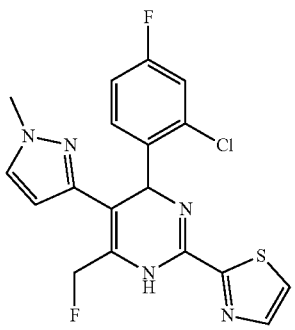 [SMILES: Cn1ccc(C2=C(CF)NC(c3nccs3)=NC2c2ccc(F)cc2Cl)n1]

A mixture of example 41 (60 mg, 0.15 mmol) and DAST (35.9 mg, 0.22 mmol) in DCM (4 mL) was stirred for 2 hours at −78° C. It was partitioned (DCM-H$_2$O). The organic was dried (Na$_2$SO$_4$), filtered and concentrated. The residue was purified by prep-HPLC (Cis column, MeCN/H$_2$O) to give the title compound as yellow solid (19.4 mg, 32%) ESIMS m/z=406.10, 408.10[M+H]$^+$; $^1$H NMR (300 MHz, Methanol-d$_4$) δ: 7.92 (m, 1H), 7.80 (m, 1H), 7.43 (s, 1H), 7.02 (m, 3H), 5.54 (m, 2H), 4.63 (m, 1H), 4.92 (d, 1H), 5.29 (m, 1H), 3.77 (m, 3H).

Example 44

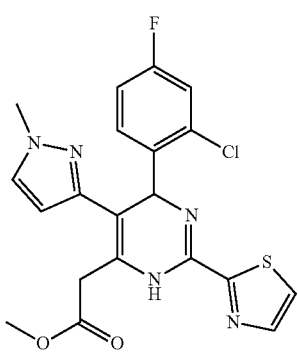 [SMILES: COC(=O)CC1=C(c2ccn(C)n2)C(c2ccc(F)cc2Cl)N=C(c2nccs2)N1]

The mixture of step 35a (300 mg, 0.644 mmol), DIPEA (249 mg, 1.93 mmol), Pd(PPh$_3$)$_4$ (149 mg, 0.129 mmol) in MeOH (30 mL) was stirred for 3 hours at 50° C. under CO atmosphere (2atm). The solvent was concentrated. The residue was purified by PREP-HPLC to give the title compound (4 mg, 0.02%) as yellow solid. ESIMS, m/z=446.00, 448.00 [M+H]$^+$; $^1$H NMR (300 MHz, DMSO-d$_6$), δ 9.57 (s, 0.6H), 8.57 (s, 0.4H), 7.90 (m, 2H), 7.60 (m, 2H), 7.40 (m, 1H), 7.15 (m, 1H), 6.10 (d, 0.4H), 6.00 (s, 1H), 5.87 (d, 0.6H), 3.75 (m, 3H), 3.65 (m, 3H).

Example 45

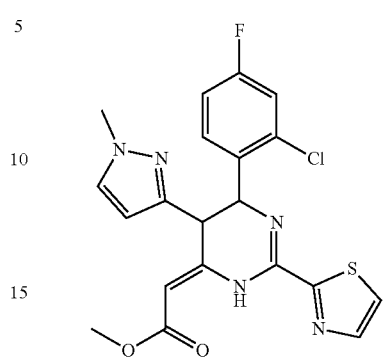

The title compound was isolated from the reaction prepared in example 44. ESIMS, m/z=446.10, 448.10 [M+H]$^+$; $^1$H-NMR (300 MHz, DMSO-d$_6$), δ 11.57 (s, 1H), 8.45 (m, 0.6H), 8.05 (m, 2H), 7.40 (m, 2H), 7.20 (m, 1H), 7.10 (m, 1H), 5.50 (m, 2H), 4.25 (d, 1H), 3.65 (m, 3H), 3.55 (m, 3H).

Example 46

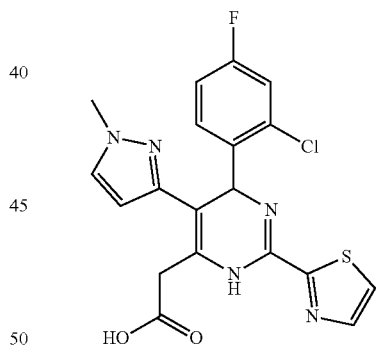

A mixture of example 44 and 45 (50 mg, 0.112 mmol) in MeOH (5 mL) and NaOH (1M, 0.4 ml) was stirred for 16 hours at rt. The PH value was adjusted to 3~4 with HCl (1M). It was partitioned (EtOAc-brine). The organic was dried (Na$_2$SO$_4$), filtered and concentrated. PREP-HPLC (C18, MeCN/water) to give the title compound as yellow solid (5.0 mg, 10%). ESIMS m/z=432.20, 434.10 [M+H]$^+$; $^1$H-NMR (300 MHz, methanol-d$_4$): δ 7.89 (s, 1H), 7.73 (m, 2H), 7.42 (d, 1H), 7.18 (m, 1H), 7.00 (m, 1H), 6.10 (s, 2H), 3.81 (s, 3H), 3.70 (d, 1H), 3.55 (d, 1H).

Example 47

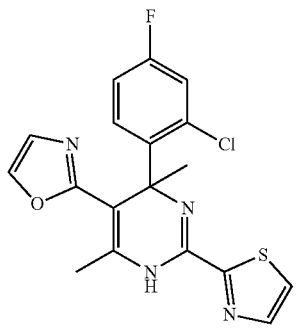 [SMILES: CC1=C(c2ncco2)C(C)(c2ccc(F)cc2Cl)N=C(c2nccs2)N1]

Step 47a.

A mixture of 2-chloro-1-ethynyl-4-fluorobenzene (4 g, 25.8 mmol), allyl 3-oxobutanoate (3.7 g, 25.8 mmol), and indium(III) chloride (0.57 g, 2.58 mmol) in o-xylene (25 mL) was stirred for 3 hours at 130° C. It was concentrated and the residue was chromatographed (silica, ethyl acetate/petroleum ether) to give the desired product as white solid (0.9 g, 11.7%). ESIMS m/z=297.20, 299.20 [M+H]$^+$.

Step 47b.

A mixture of the compound from step 47a (0.87 g, 2.9 mmol), thiazole-2-carboximidamide HCl salt (0.48 g, 2.9 mmol) and NaHCO$_3$ (0.73 g, 8.7 mmol) in NMP (10 mL) was stirred for 12 hours at 90° C. It was concentrated and the residue was chromatographed (silica, ethyl acetate/petroleum ether) to give the desired product as yellow oil (0.35 g, 29.4%). ESIMS m/z=406.20, 408.20 [M+H]$^+$.

Step 47c.

A mixture of the compound from step 47b (335 mg, 0.83 mmol), morpholine (72.21 mg, 0.83 mmol) and Pd(PPh$_3$)$_4$ (46.2 mg, 0.04 mmol) in THF (10 mL) was stirred for 4 hours at rt. It was concentrated to give the desired product as yellow oil (240 mg, 79.5%). ESIMS m/z=366.15, 368.15 [M+H]$^+$.

Step 47d.

A mixture of the compound from step 47c (0.22 g, 0.6 mmol)), NBS (0.13 g, 0.72 mmol)) and Et$_3$N (0.09 g, 0.9 mmol)) in DCM (10 mL) was stirred for 4 hours at rt. It was concentrated and the residue was chromatographed (silica, ethyl acetate/petroleum ether) to give the desired compound as yellow oil (0.165 g, 68.5%). ESIMS m/z=402.10, 404.10 [M+H]$^+$.

Step 47e.

The title compound was prepared by reacting of the compound from step 47d and 2-(tributylstannyl)oxazole by following the similar procedure described in step 33a and 33b. ESIMS m/z=389.07, 391.07 [M+H]$^+$; $^1$H NMR (300 MHz, CD$_3$OD, ppm): δ 8.03 (s, 1H), 7.85 (s, 1H), 7.68 (t, 1H), 7.61 (s, 1H), 7.15 (d, 1H), 7.04 (t, 1H), 6.98 (s, 1H), 2.18 (S, 3H), 2.09 (S, 3H).

Example 48

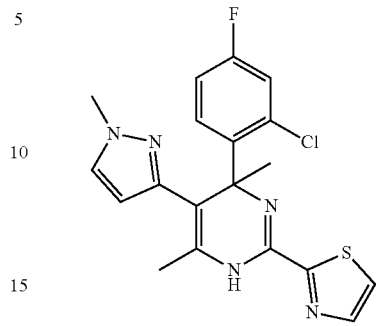

The title compound was prepared by reacting of the compound from step 47d and 1-methyl-2-(tributylstannyl)-1H-imidazole by following the similar procedure described in step 33a and 33b. ESIMS m/z=402.10, 404.10 [M+H]$^+$; $^1$H NMR (300 MHz, CD$_3$OD, ppm): δ 7.95 (s, 1H), 7.70 (s, 1H), 7.39 (t, 1H), 7.27 (s, 1H), 7.17 (d, 1H), 6.94 (t, 1H), 5.42 (s, 1H), 3.77 (S, 3H), 1.85 (S, 3H), 1.78 (s, 3H).

Example 49

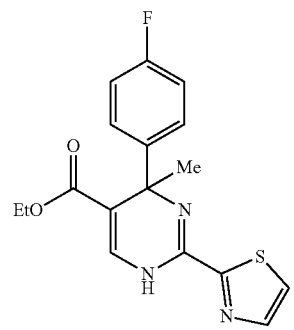 [SMILES: CCOC(=O)C1=CNC(c2nccs2)=NC1(C)c1ccc(F)cc1]

Step 49a.

To a solution of ethyl 2-(diethoxyphosphoryl)acetate (8.36 g, 37.3 mmol) in THF (62 mL, 0.4 M) at 0° C. was added NaH (1.49 g, 60% wt %, 37.3 mmol). The mixture was stirred at 0° C. for 0.5 hour. Then 1-(4-fluorophenyl)ethan-1-one (3.43 g, 24.9 mmol) was added. The solution was stirred at 0° C. for 2 hours, warmed to rt and stirred for overnight. The reaction was quenched with saturated NH$_4$Cl aqueous solution. It was partitioned (EtOAc-brine). The organic was dried (Na$_2$SO$_4$), filtered and concentrated. The residue was chromatographed (silica gel, EtOAc/hexanes) to give the desired product (4.14 g, 80%). $^1$H NMR (500 MHz, CDCl$_3$) δ 7.51-7.43 (m, 2H), 7.14-7.08 (m, 2H), 6.10 (d, J=1.4 Hz, 1H), 4.22 (q, J=7.1 Hz, 2H), 2.57 (d, J=1.3 Hz, 3H), 1.33 (t, J=7.1 Hz, 3H).

Step 49b.

A mixture of the compound from Step 49a (1.71 g, 8.23 mmol) and bromine (2.89 g, 18.1 mmol) in CCl$_4$ (41 mL, 0.2 M) was stirred at rt for 4 days. Then the mixture was treated with saturated Na$_2$S$_2$O$_3$ aqueous solution. It was partitioned (EtOAc-brine). The organic was dried (Na$_2$SO$_4$), filtered and concentrated to give the residue, which was taken into the next step without further purification.

Step 49c.

A mixture of the compound from Step 49b in THF (41 mL, 0.2 M) was treated with 1.0M TBAF solution in THF at 0° C. and the mixture was stirred at 0° C. for 3 hours. It was partitioned (EtOAc—NaHCO₃aq.). The organic was dried (Na₂SO₄), filtered and concentrated to give the residue, which was chromatographed (silica gel, EtOAc/hexanes) to give the desired product as a mixture of Z and E diastereomers (2.17 g, 92% over 2 steps). ¹H NMR (500 MHz, CDCl₃) δ 7.24-6.99 (m, 4H), 4.04-3.97 (m, 2H), 2.38-2.28 (m, 3H), 1.03-0.98 (m, 3H).

Step 49d.

To a solution of the compound from Step 49c (2.17 g, 7.57 mmol) at rt was added tributyl(vinyl)stannane (4.80 g, 15.1 mmol), tetrakis(triphenylphosphine)palladium(0) (1.75 g, 1.51 mmol). The mixture was degassed by N₂, then heated to 90° C. and kept for overnight. It was concentrated and the residue was chromatographed (silica gel, EtOAc/hexanes) to give the desired product (1.49 g, 84%). ¹H NMR (500 MHz, CDCl₃) δ 7.28-6.99 (m, 4H), 6.70 (dd, J=17.3, 11.1 Hz, 0.5H), 6.25 (dd, J=17.6, 11.1 Hz, 0.5H), 5.37-5.30 (m, 1H), 5.18-5.08 (m, 1H), 4.04-3.97 (m, 2H), 2.38-2.28 (m, 3H), 1.03-0.98 (m, 3H).

Step 49e.

To a solution of the compound from Step 49d (878 mg, 3.75 mmol) in CH₂Cl₂ (100 mL, 0.038 M) at −78° C. was induced ozone until the color of solution turned into light blue. Then the excess ozone was purged with N₂. Me₂S (5 mL) was added and the mixture was warmed to rt and stirred for overnight. It was concentrated and the residue was chromatographed (silica gel, EtOAc/hexanes) to give a mixture of Z and E diastereomers (632 mg, 71%). ¹H NMR (500 MHz, CDCl₃) δ 10.15 (s, 0.5H), 9.35 (s, 0.5H), 7.35-6.99 (m, 4H), 4.35 (q, J=7.2 Hz, 1H), 3.97 (q, J=7.2 Hz, 1H), 2.20-2.10 (m, 3H), 1.00-0.90 (m, 3H).

Step 49f.

To a solution of the compound from Step 49e in N-methyl-2-pyrrolidone (14 mL, 0.1M) at rt was added thiazole-2-carboximidamide hydrochloride (246 mg, 1.50 mmol) and NaHCO₃ (230 mg, 2.73 mmol) at rt. Then the mixture was heated to 90° C. and kept for 2 days. It was partitioned (EtOAc-brine). The organic was dried (Na₂SO₄), filtered and concentrated to give the residue, which was chromatographed (silica gel, EtOAc/hexanes) to give the title product (172 mg, 37%). ESIMS m/z=346.12 [M+H]⁺. ¹H NMR (500 MHz, CD₃OD) δ 7.70-7.45 (m, 2H), 7.25-7.00 (m, 5H), 4.03-3.91 (m, 2H), 2.30 (s, 3H), 1.01 (t, J=7.2 Hz, 3H).

Step 50a.

A mixture of the compound from Step 49f (161 mg, 0.466 mmol) with MeOH (6 mL) and 2N NaOH aqueous solution (4 mL) was stirred under reflux for overnight. The mixture was cooled to rt and treated with NH₄Cl solution. It was partitioned (CH₂Cl₂—NH₄Cl aq). The organic was dried (Na₂SO₄), filtered and concentrated to give the residue, which was chromatographed (silica gel, CH₂Cl₂/MeOH) to give the desired product (60 mg, 41%). ESIMS m/z=318.08 [M+H]⁺.

Step 50b.

A mixture of the compound from Step 50a (58.9 mg, 0.167 mmol), NEt₃ (25.3 mg, 0.251 mmol) and NBS (29.8 mg, 0.167 mmol) in CH₂Cl₂ (5.6 mL, 0.03 M) was stirred at rt for 1 h. The mixture was partitioned (CH₂Cl₂-brine). The organic was dried (Na₂SO₄), filtered and concentrated to give the residue, which was chromatographed (silica gel, EtOAc/hexanes) to give the desired product (31 mg, 47%). ESIMS m/z=352.00, 354.00 [M+H]⁺.

Step 50c.

A mixture of the compound from Step 50b (25.6 mg, 0.0727 mmol), Boc₂O (31.7 mg, 0.145 mmol), DMAP (8.9 mg, 0.0727 mmol), NEt₃ (29.4 mg, 0.291 mmol) in CH₂Cl₂ (2.4 mL, 0.03 M) was stirred at rt for overnight. The mixture was partitioned (CH₂Cl₂-brine). The organic was dried (Na₂SO₄), filtered and concentrated to give the residue, which was chromatographed (silica gel, EtOAc/hexanes) to give the desired product (30 mg, 92%). ESIMS m/z=352.00, 354.00 [M+H-Boc]⁺.

Step 50d.

A mixture of the compound from Step 50c (18.1 mg, 0.040 mmol), 1-methyl-5-(tributylstannyl)-1H-pyrazole (29.7 mg, 0.080 mmol) and tetrakis(triphenylphosphine)palladium(0) (9.2 mg, 0.008 mmol) was stirred at 90° C. for overnight. The mixture was concentrated and the residue was chromatographed (silica gel, EtOAc/hexanes) to give the desired product (12.8 mg, 71%). ESIMS m/z=354.16 [M+H-Boc]⁺.

Step 50e.

A mixture of the compound from Step 50d (12.8 mg, 0.0282 mmol), TFA (0.4 mL) and CH₂Cl₂ (1.6 mL) was stirred at 90° C. for 1.5 hours. The mixture was concentrated and the residue was chromatographed (silica gel, CH₂Cl₂/MeOH) to give the title product (9.3 mg, 93%). ESIMS m/z=354.16 [M+H]⁺. 1H NMR (500 MHz, CD₃OD) δ 7.89 (d, J=3.2 Hz, 1H), 7.72 (d, J=3.2 Hz, 1H), 7.63 (ddd, J=7.1, 5.6, 2.9 Hz, 2H), 7.32 (d, J=2.3 Hz, 1H), 7.12-7.01 (m, 2H), 6.90 (s, 1H), 5.63 (d, J=2.3 Hz, 1H), 5.49 (s, 1H), 3.78 (s, 3H), 1.97 (s, 3H).

Example 50

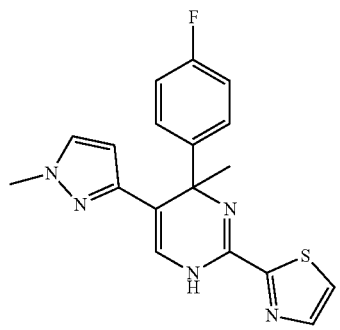 [SMILES: Cn1ccc(C2=CNC(c3nccs3)=NC2(C)c2ccc(F)cc2)n1]

Example 51

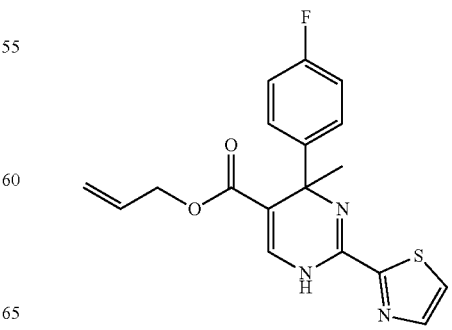

Step 51a.

A mixture of compound 1-(4-fluorophenyl)ethanone (10.0 g, 72.4 mmol), N-methylhydroxylamine hydrochloride (6.7 g, 79.7 mmol) and $K_2CO_3$ (12.0 g, 0.92 mmol) in DMF (100 mL) was stirred for 24 hours at 40° C. It was partitioned (DCM-brine). The organic was dried ($Na_2SO_4$), filtered and concentrated to give the desired compound as a yellow solid (8 g, 66.7%). $^1$H NMR (400 MHz, DMSO) δ 2.25 (3H, s), 3.53 (3H, s), 7.26-7.37 (2H, m), 7.44-7.62 (2H, m).

Step 51b.

A mixture of compound from step 51a (8.0 g, 48 mmol) and allyl propiolate ((7.9 g, 71.8 mmol) in THF (150 mL) was stirred overnight at 40° C. The solvent was removed in vacuum. The residue was purified by Flash-Prep-HPLC (C18, MeCN/water) to give the title compound as a yellow oil (6.3 g, 47.5%). ESIMS m/z=278.15 $[M+H]^+$.

Step 51c.

A solution of m-CPBA (3.7 g, 22 mmol) in 50 mL of DCM was added to a solution of allyl 3-(4-fluorophenyl)-2,3-dimethyl-2,3-dihydroisoxazole-4-carboxylate (5.0 g, 18 mmol) in 50 mL of DCM and the solution was stirred for 2 h at rt. It was concentrated and chromatographed (silica, ethyl acetate/petroleum ether) to afford the desired compound as yellow oil (2.8 g, 62.6%). ESIMS m/z=249.10 $[M+H]^+$.

Step 51d.

A mixture of step 51c (3.0 g, 12 mmol), thiazole-2-carboximidamide hydrochloride (3.0 g, 12 mmol) and $K_2CO_3$ in 10 mL of DMF was stirred at 80° C. over night. The mixture was washed with water and extracted with DCM. The organic layer was dried ($Na_2SO_4$), concentrated and chromatographed (silica, ethyl acetate/petroleum ether) to give the title compound as a yellow solid (400 mg, 9.3%). ESIMS m/z=357.95 $[M+H]^+$; $^1$H NMR (300 MHz, DMSO-$d_6$) δ 10.13 (d, J=5.6 Hz, 1H), 8.14-7.76 (m, 2H), 7.73-7.27 (m, 3H), 7.12 (q, J=8.5 Hz, 2H), 5.97-5.67 (m, 1H), 5.24-5.02 (m, 2H), 4.45 (q, J=6.9, 5.4 Hz, 2H), 1.95 (3, 3H).

Example 52

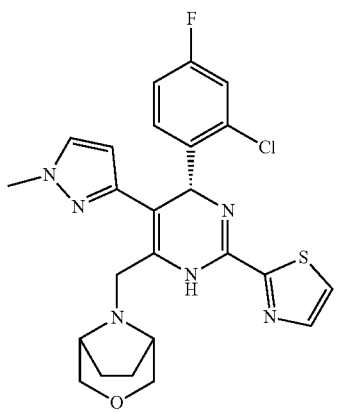 [SMILES: Cn1ccc(C2=C(CN3C4CCC3COC4)NC(c3nccs3)=N[C@H]2c2ccc(F)cc2Cl)n1]

Step 52a.

A solution of ethyl (R)-2-hydroxypropanoate (5 g, 42.3 mmol) and 2,2,6-trimethyl-4H-1,3-dioxin-4-one (6 g, 42.3 mmol) was stirred for 4 hours at 120° C. The mixture was concentrated under vacuum to give desired product (9 g, crude) as yellow oil, which was used in the next step without further purification. ESI MS m/z=203.25 $[M+H]^+$.

Step 52b.

A solution of the compound from step 52a (5 g, 24.5 mmol), 2-chloro-4-fluorobenzaldehyde (4.3 g, 27.3 mmol), TsOH (cat) and HOAc (cat) in toluene (60 mL) was stirred at 110° C. overnight. The mixture was concentrated. The residue was chromatographed (silica, ethyl acetate/petroleum ether) to give the desired product (5.93 g, 70.0%) as yellow solid. ESI MS m/z=343.00 $[M+H]^+$.

Step 52c.

A solution of the compound from step 52b (5 g, 14.6 mmol), thiazole-2-carboximidamide HCl salt (2.38 g, 14.6 mmol) and $K_2CO_3$ (2.01 g, 14.6 mmol) in DMF (20 mL) was stirred for 2 hours at 80° C. It was diluted with EtOAc and washed with brine, filtered and concentrated. After the residue was purified by silica gel column (ethyl acetate/petroleum ether), the mixture was recrystallized from EtOH at 0° C. to give the desired product as yellow solid (1.25 g, 25.0%). ESI MS m/z=452.05 $[M+H]^+$.

Step 52d.

A solution of the compound from step 52c (950 mg, 2.10 mmol), (Boc)$_2$O (915.6 mg, 4.20 mmol) and DMAP (307 mg, 2.51 mmol) in DCM (30 mL) was stirred for 1 hour at rt. It was concentrated and residue was chromatographed (silica, ethyl acetate/petroleum ether) to give the desired compound as yellow solid (1.07 g, 92%). ESI MS m/z=552.30 $[M+H]^+$.

Step 52e.

A solution of the compound from step 52d (965 mg, 1.75 mmol) in a solution of NaOH [40 mL, 2M in $H_2O$/MeOH (1:5)] was stirred for 18 hours at rt. After being acidified with aq HCl (4N) to pH 5, the mixture was extracted with DCM. The organic layer was washed with aq. NH$_4$Cl and $H_2O$, dried ($Na_2SO_4$), filtered and concentrated. The residue was chromatographed (silica, ethyl acetate/petroleum ether) to give the desired compound as yellow solid (620 mg, 78%). ESI MS m/z=452.15 $[M+H]^+$.

Step 52f.

A solution of the compound from step 52e (250 mg, 0.55 mmol) in DCM (10 mL) was treated with NBS (295 mg, 1.66 mmol) for 6 hours at rt. The reaction was quenched by the addition of water (2 mL) and extracted with DCM. The organic layer was dried ($Na_2SO_4$), filtered and concentrated. The residue was chromatographed (Cis column, MeCN/$H_2O$) to give the desired compound as yellow solid (103.5 mg, 33%). ESI MS m/z=566.10, 568.10 $[M+H]^+$. $^1$H NMR (400 MHz, DMSO-$d_6$) δ 8.04 (m, 2H), 7.98 (d, 1H), 7.57 (m, 1H), 7.23 (m, 1H), 6.35 (s, 1H), 4.45 (m, 2H), 1.15 (s, 9H).

Step 52g.

To a solution of the compound from step 52f (25 mg, 0.044 mmol) and 3-oxa-8-azabicyclo[3.2.1]octane hydrochloride (7.93 mg, 0.053 mmol) in DCM (1.5 ml) at rt was added DIPEA (0.019 ml, 0.110 mmol). The resuting clear solution was stirred at rt for 4 h. More 3-oxa-8-azabicyclo[3.2.1]octane hydrochloride (3.3 mg, 0.5 eq) was added at rt. After 2 h, the mixture was directly chromatographed (silica, ethyl acetate/hexanes) to give the desired compound as yellow solid (20 mg, 76%). ESI MS m/z=597.08, 599.07, 601.07 $[M+H]^+$. $^1$H NMR (400 MHz, CDCl$_3$) δ 7.79 (d, J=3.1 Hz, 1H), 7.39 (d, J=3.2 Hz, 1H), 7.21-7.14 (m, 0H), 7.08 (dd, J=8.5, 2.6 Hz, 1H), 6.81 (td, J=8.4, 2.6 Hz, 1H), 6.36 (s, 1H), 4.05 (q, J=7.1 Hz, 0H), 3.76 (t, J=9.8 Hz, 1H), 3.51-3.43 (m, 1H), 3.33 (s, 1H), 3.24 (s, 1H), 3.09 (s, 1H), 1.98 (s, 1H), 1.19 (t, J=7.1 Hz, 1H), 1.16 (s, 5H).

Step 52h.

To a solution of the compound from step 52g (10 mg, 0.017 mmol) and 1-methyl-3-(tributylstannyl)-1H-pyrazole (12.4 mg, 0.033 mmol) in toluene (1.0 ml) at rt was added Pd(Ph$_3$P)$_4$ (1.9 mg, 1.672 μmol). The mixture was degassed 3 times before being heated at 130° C. using a microwave reactor for 30 min. The reaction was repeated once. The reaction mixtures were combined and chromatographed (silica, ethyl acetate/hexanes) to give the desired compound as yellow solid (15 mg, 75%). ESI MS m/z=599.16, 601.16 [M+H]+. 1H NMR (400 MHz, CDCl3) δ 7.77 (d, J=3.2 Hz, 1H), 7.65-7.51 (m, 1H), 7.52-7.34 (m, 1H), 7.34-7.29 (m, 1H), 7.19 (s, 2H), 7.02 (dd, J=8.6, 2.7 Hz, 1H), 6.81 (s, 1H), 6.71-6.59 (m, 2H), 4.77 (s, 0H), 4.09-3.94 (m, 1H), 3.79 (s, 3H), 3.71 (t, J=6.0 Hz, 0H), 3.62-3.50 (m, 1H), 3.48 (s, 2H), 3.21 (d, J=13.3 Hz, 1H), 2.20 (s, 1H), 1.97 (s, 1H), 1.86 (s, 2H), 1.69-1.48 (m, 1H), 1.35-1.09 (m, 3H), 1.14 (s, 9H), 0.84 (t, J=7.3 Hz, 1H).

Step 52i.

A clear yellow-orange solution of the compound from step 52h (15.0 mg, 0.025 mmol) in TFA/CH2Cl2 (1/3, 1.0 ml) was stirred at 0° C. for 1 h and then at rt for 1.5 h. The mixture was concentrated. The residue was co-evaporated with toluene, then with DCM and a little bit of DIPEA. The residue was chromatographed (silica, hexanes/ethyl acetate) to afford the title compound as yellow foam (11.0 mg, 88%). ESI MS m/z=499.15, 501.15 [M+H]+.

Example 53

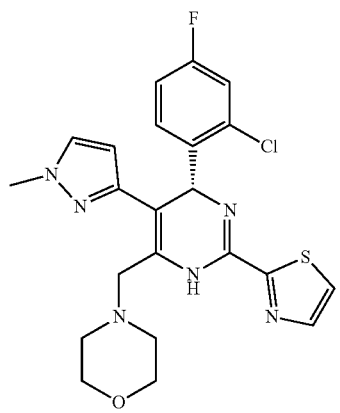 [SMILES: Cn1ccc(C2=C(CN3CCOCC3)NC(c3nccs3)=N[C@H]2c2ccc(F)cc2Cl)n1]

Step 53a.

To a solution of the compound from step 52f (30 mg, 0.053 mmol) and morpholine (5.54 mg, 0.064 mmol) in DCM (1.5 ml) at rt was added DIPEA (0.023 ml, 0.133 mmol). The resuting clear solution was stirred at rt overnight. The mixture was directly chromatographed (silica, ethyl acetate/hexanes) to give the desired compound as yellow solid (27.8 mg, 92%). ESI MS m/z=571.06, 573.06, 575.05 [M+H]+.

Step 53b.

To a solution of the compound from step 53a (27.8 mg, 0.049 mmol) and 1-methyl-3-(tributylstannyl)-1H-pyrazole (36.1 mg, 0.097 mmol) in toluene (2.0 ml) at rt was added Pd(Ph3P)4 (5.62 mg, 4.86 μmol). The mixture was degassed 3 times before being heated at 130° C. using a microwave reactor for 60 min. The reaction mixture was directly chromatographed (silica, ethyl acetate/hexanes) to give the desired compound as yellow solid (24.0 mg, 86%). ESI MS m/z=573.19, 575.19 [M+H]+.

Step 53c.

A clear yellow-orange solution of the compound from step 53b (24.0 mg, 0.042 mmol) in TFA/CH2Cl2 (1/3, 1.2 ml) was stirred at rt for 4 h. The mixture was concentrated. It was co-evaporated with DCM containing some Et3N. The residue was chromatographed (silica, hexanes/EtOAc) to afford the title compound as yellow foam (14.6 mg, 74%). ESI MS m/z=473.14, 475.13 [M+H]+.

Example 54

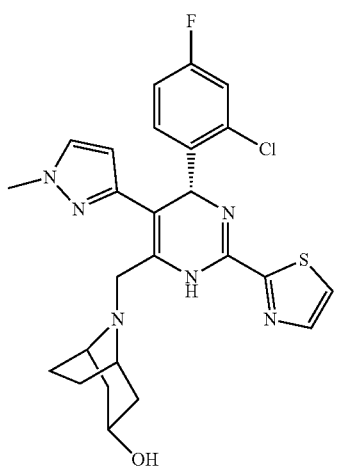 [SMILES: Cn1ccc(C2=C(CN3C4CCC3CC(O)C4)NC(c3nccs3)=N[C@H]2c2ccc(F)cc2Cl)n1]

Step 54a.

To a solution of the compound from step 52f (25 mg, 0.044 mmol) and (1R,3S,5S)-8-(13-chloranyl)-8-azabicyclo[3.2.1]octan-3-ol (9.40 mg, 0.057 mmol) in DCM (1.5 ml) at rt was added DIPEA (0.023 ml, 0.133 mmol). The resuting clear solution was stirred at rt overnight. The mixture was directly chromatographed (silica, ethyl acetate/hexanes/MeOH) to give the desired compound as yellow solid (25.0 mg, 92%). ESI MS m/z=611.06, 633.09, 615.09 [M+H]+.

Step 54b.

To a solution of the compound from step 54a (25.0 mg, 0.041 mmol) and 1-methyl-3-(tributylstannyl)-1H-pyrazole (30.3 mg, 0.082 mmol) in toluene (2.0 ml) at rt was added Pd(Ph3P)4 (4.72 mg, 4.09 μmol). The mixture was degassed 3 times before being heated at 135° C. using a microwave reactor for 45 min. The reaction mixture was directly chromatographed (silica, MeOH/dichloromethane) to give the desired compound as yellow solid (14.4 mg, 57%). ESI MS m/z=613.22, 615.21 [M+H]+.

Step 54c.

A clear yellow-orange solution of the compound from step 54b (14.4 mg, 0.023 mmol) in TFA/CH2Cl2 (1/3, 1.2 ml) was stirred at rt for 4 h. The mixture was concentrated. It was co-evaporated with DCM containing some Et3N. The residue was chromatographed (silica, MeOH/dichloromethane) to afford the title compound as yellow foam (12.0 mg, 100%). ESI MS m/z=513.17, 515.16 [M+H]+.

Example 55

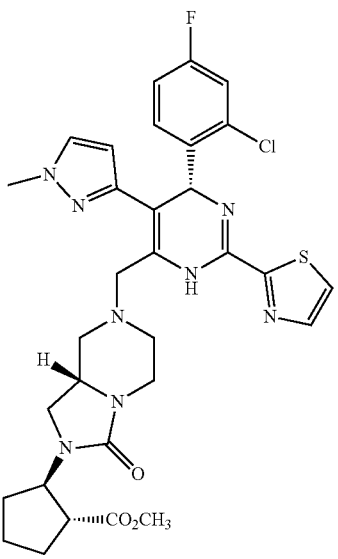 [SMILES: COC(=O)[C@@H]1CCC[C@H]1N1C[C@@H]2CN(CC3=C(c4ccn(C)n4)[C@H](c4ccc(F)cc4Cl)N=C(c4nccs4)N3)CCN2C1=O]

Step 55a.

To a solution of the compound from step 52f (30 mg, 0.053 mmol) and (1R,2R)-2-((S)-3-oxohexahydroimidazo[1,5-a]pyrazin-2 (3H)-yl)cyclopentane-1-carboxylic acid (prepared according to WO 2015/132276, 17.46 mg, 0.069 mmol) in DCM (1.5 ml) at rt was added DIPEA (0.028 ml, 0.159 mmol). The resuting clear solution was stirred at rt overnight. More (1R,2R)-2-((S)-3-oxohexahydroimidazo[1,5-a]pyrazin-2 (3H)-yl)cyclopentane-1-carboxylic acid (0.2 eq, 2.7 mg) was added. The mixture was stirred at rt for 3 h before being acidified to pH ~2 with 0.5 N HCl aq. and diluted with EtOAc. The organic layer was washed with brine, dried over $Na_2SO_4$ (s), filtered and concentrated. The residue was dried under vacuum to give the desired compound as yellow solid (39.0 mg, 100%). ESI MS m/z=737.13, 739.13 $[M+H]^+$.

Step 55b.

To a solution of the compound from step 55a (26.0 mg, 0.035 mmol) and 1-methyl-3-(tributylstannyl)-1H-pyrazole (26.1 mg, 0.070 mmol) in toluene (2.0 ml) at rt was added $Pd(Ph_3P)_4$ (4.07 mg, 3.52 µmol). The mixture was degassed 3 times before being heated at 140° C. using a microwave reactor for 60 min. More $Pd(Ph_3P)_4$ (4.07 mg, 3.52 µmol) was added. The mixture was heated at 140° C. using a microwave reactor for another 30 min. It was diluted with MTBE and 0.25 N NaOH aq. The aqueous layer was extracted with MTBE before being acidified to pH ~2. It was extracted with EtOAc and then DCM. The combined organic layers were washed with brine, dried over $Na_2SO_4$ (s), filtered and concentrated. The residue was dried under vacuum to give the desired compound as yellow solid (21.3 mg, 82%). ESI MS m/z=739.26, 741.26 $[M+H]^+$.

Step 55c.

A clear yellow solution of the compound from step 55b (32.0 mg, 0.043 mmol) in MeOH (2 ml) at rt was treated with 4 N HCl in 1,4-dioxane (0.216 ml, 0.866 mmol). The mixture was stirred at rt for 1 h before being concentrated. The residue was chromatographed (silica, MeOH/dichloromethane) to afford the desired compound as yellow solid (10.0 mg, 31%). ESI MS m/z=753.28, 755.28 $[M+H]^+$.

Step 55d.

A clear yellow-orange solution of the compound from step 55c (10.0 mg, 0.013 mmol) in $TFA/CH_2Cl_2$ (1/2, 1.0 ml) was stirred at rt for 1 h. The mixture was concentrated. It was co-evaporated with DCM containing some DIPEA. The residue was chromatographed (silica, MeOH/dichloromethane) to afford the title compound as yellow solid (7.0 mg, 81%).

ESI MS m/z=653.23, 655.22 $[M+H]^+$.

Example 56

Step 56a.

To a solution of the Example 55 (5.0 mg, 7.65 µmol) in THF (0.5 ml) and Water (0.18 ml) at rt was added LiOH (0.077 ml, 0.038 mmol). The mixture was stirred at rt overnight before being acidified to pH ~2 with 0.5 N HCl aq and diluted with EtOAc. The organic layer was washed with brine, dried over $Na_2SO_4$ (s), filtered and concentrated. The residue was dried under vacuum to afford the title compound as yellow solid (4.0 mg, 82%). ESI MS m/z=639.21, 641.21 $[M+H]^+$.

Example 57

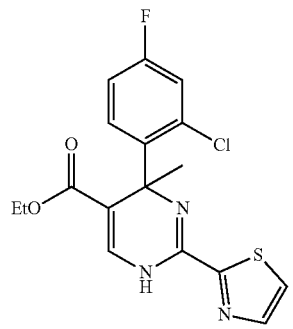 [SMILES: CCOC(=O)C1=CNC(c2nccs2)=NC1(C)c1ccc(F)cc1Cl]

The title compound (31 mg) was prepared following the similar procedure in the preparation of the title compound in example 49 by replacing 1-(4-fluorophenyl)ethan-1-one with 1-(2-chloro-4-fluorophenyl)ethan-1-one in step 49a. ESIMS m/z=380.13, 382.13 $[M+H]^+$. $^1H$ NMR (500 MHz, $CD_3OD$) δ 7.95 (d, J=3.2 Hz, 1H), 7.79-7.70 (m, 2H), 7.44 (s, 1H), 7.18 (dd, J=8.6, 2.8 Hz, 1H), 7.15-7.07 (m, 1H), 4.03-3.87 (m, 2H), 2.00 (s, 3H), 1.07 (t, J=7.1 Hz, 3H).

BIOLOGICAL ACTIVITY

Methods: HepAD38 cells are maintained as previously reported (Ladner et al, *Antimicrob. Agents Chemother.* 1997, 4, 1715). Briefly, cells are passaged upon attaining confluency in DMEM/F12 media in the presence of 10% FBS, Penn/Strep, 250 µg/mL G418, and 1 µg/ml tetracycline. Novel compounds are screened by first washing cells three times with PBS to remove tetracycline, and plating in 96 well plates at 35,000 cells/well. Compounds dissolved in DMSO are then diluted 1:200 into wells containing cells. Five days after compound addition, material is harvested for analysis. For an extended 8 day analysis, cells are plated and treated as described above, but media and compound are refreshed on d2 and d5 post initial treatment.

On harvest day, virion DNA is obtained by lysing with Sidestep Lysis and Stabilization Buffer and then quantified via quantitative real time PCR. Commercially available ELISA kits are used to quantitate the viral proteins HBsAg (Alpco) or HbeAg (US Biological) by following the manufacturer's recommended protocol after diluting samples to match the linear range of their respective assays. Irrespective of readout, compound concentrations that reduce viral product accumulation in the cell lysates or supernatants by relative to no drug controls (EC50) are reported; $EC_{50}$ ranges are as follows: A<1 µM; B 1-10 µM; C>10 µM.

Additionally, on day of harvest, compound toxicity is evaluated by treating cells with ATPlite 1 Step according to the manufacturer's protocol. Compound concentrations that reduce total ATP levels in wells by 50% relative to no drug controls ($CC_{50}$) are reported; $CC_{50}$ ranges are as follows: A>30 µM; B 10-30 µM; C<10 µM.

TABLE 1

Summary of Activities

| Compd. Number | HepAD38 $EC_{50}$ (µM) | $CC_{50}$ (µM) ATPlite |
|---|---|---|
| 1 | B | B |
| 2 | B | A |
| 3 | A | A |
| 4 | C | A |
| 5 | B | A |
| 6 | C | A |
| 7 | B | A |
| 8 | C | A |
| 9 | B | A |
| 10 | B | A |
| 11 | A | A |
| 12 | A | A |
| 13 | A | A |
| 13a | B | A |
| 13b | A | A |
| 14 | A | A |
| 15 | A | A |
| 16 | A | A |
| 16a | A | A |
| 16b | A | A |
| 17 | A | A |
| 18 | A | B |
| 19 | B | A |
| 20 | B | A |
| 21 | C | A |
| 22 | C | A |
| 25 | C | A |
| 26 | C | A |
| 27 | C | A |
| 28 | C | A |
| 29 | C | A |
| 30 | C | A |
| 31 | B | A |
| 32 | A | A |
| 33 | B | A |
| 34 | A | A |
| 35 | A | A |
| 36 | A | A |
| 37 | C | B |
| 38 | A | A |
| 39 | A | A |
| 40 | B | A |
| 41 | A | B |
| 42 | A | A |
| 43 | A | A |
| 44 | B | A |
| 45 | B | B |
| 46 | C | B |
| 47 | C | |
| 48 | C | |
| 49 | B | |
| 50 | B | |
| 51 | B | |
| 52 | A | |
| 53 | A | |

TABLE 1-continued

Summary of Activities

| Compd. Number | HepAD38 $EC_{50}$ (µM) | $CC_{50}$ (µM) ATPlite |
|---|---|---|
| 54 | B | |
| 55 | B | |
| 56 | B | |
| 57 | B | |

While this invention has been particularly shown and described with references to preferred embodiments thereof, it will be understood by those skilled in the art that various changes in form and details may be made therein without departing from the scope of the invention encompassed by the appended claims.

The invention claimed is:

1. A compound represented by Formula (I):

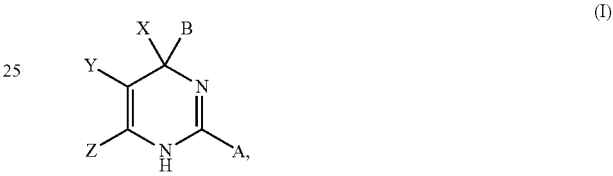

or a pharmaceutically acceptable salt thereof, wherein:
A is selected from the groups below by removal of one hydrogen atom,

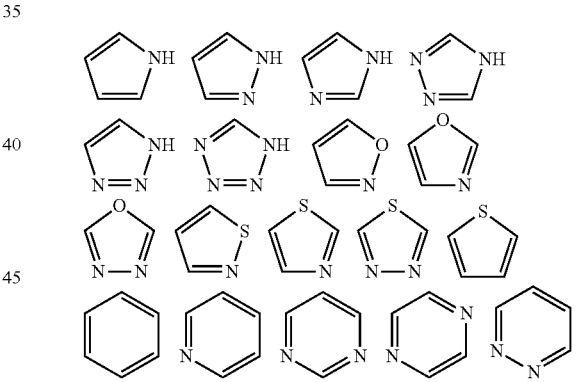

wherein each group is optionally substituted and is connected to the dihydropypyrimidine core through a carbon atom;
B is selected from the group consisting of hydrogen, CN, optionally substituted —$C_1$-$C_6$ alkyl, and optionally substituted —$C_3$-$C_6$ cycloalkyl;
X is optionally substituted phenyl;
Y is

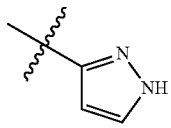

which is optionally substituted;

Z is hydrogen or —CH$_2$M; wherein M is hydrogen, —CN, —NO$_2$, —OR$_1$, protected hydroxy, —CR'R$_{1a}$R$_{2a}$, —NR$_1$R$_2$, protected amino, —CO$_2$R$_1$, or —C(O)NR$_1$R$_2$; R' is selected from the group consisting of hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, —CN, —OR$_1$, and —NR$_1$R$_2$;

R$_{1a}$ and R$_{2a}$ are independently selected from the group consisting of hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocyclic, optionally substituted aryl and optionally substituted heteroaryl; alternatively, R$_{1a}$ and R$_{2a}$ are taken together with the carbon atom to which they are attached to form an optionally substituted C$_3$-C$_{10}$-cycloalkyl or an optionally substituted 3 to 10-membered heterocyclic;

R$_1$ and R$_2$ at each occurrence are independently selected from the group consisting of hydrogen, optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocyclic, optionally substituted aryl and optionally substituted heteroaryl;

alternatively, R$_1$ and R$_2$ are taken together with the atom to which they are attached to form an optionally substituted 3- to 10-membered heterocyclic; and R$_3$ at each occurrence is selected from the group consisting of optionally substituted —C$_1$-C$_8$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocyclic, optionally substituted aryl and optionally substituted heteroaryl.

2. The compound of claim 1, wherein Z is

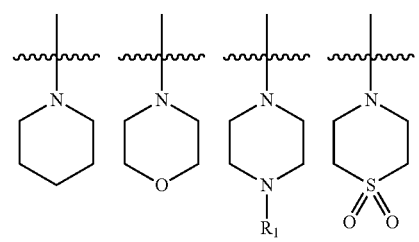

or CH$_2$M, wherein M is selected from the groups set forth below:

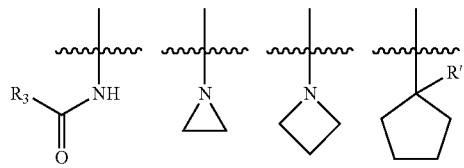
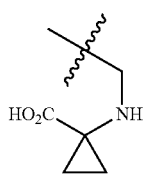

-continued

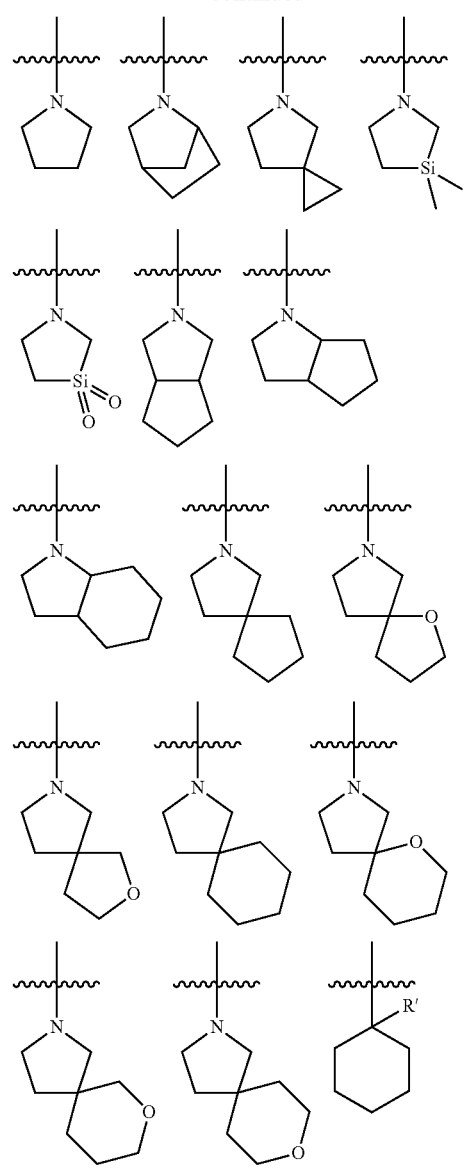
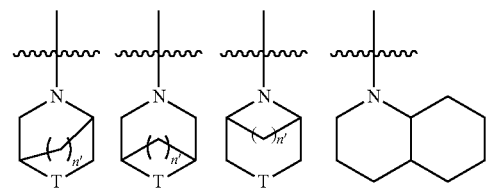

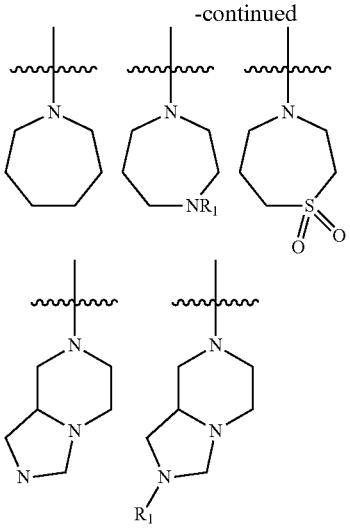

wherein each of the above shown groups is optionally substituted when possible; T is O, $NR_1$ or $CR_{1a}R_{2a}$; n' is 1, 2 or 3; R' is selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, —CN, —$OR_1$, and —$NR_1R_2$; $R_{1a}$ and $R_{2a}$ are independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl and optionally substituted heteroaryl; alternatively, $R_{1a}$ and $R_{2a}$ are taken together with the carbon atom to which they are attached to form an optionally substituted $C_3$-$C_{10}$-cycloalkyl or an optionally substituted 3 to 10-membered heterocyclic; and $R_1$ and $R_2$ are as defined in claim 1.

3. A pharmaceutical composition, comprising a compound according to claim 1, in combination with a pharmaceutically acceptable carrier or excipient.

4. A method of treating an HBV infection in a subject in need thereof, comprising administering to the subject a therapeutically effective amount of a compound of claim 1.

5. The method of claim 4, further comprising administering to the individual at least one additional therapeutic agent selected from the group consisting of a HBV polymerase inhibitor, interferon, viral entry inhibitor, viral maturation inhibitor, literature-described capsid assembly modulator, reverse transcriptase inhibitor, TLR-agonist, inducer of cellular viral RNA sensor, therapeutic vaccine, and agents of distinct or unknown mechanism, and a combination thereof.

6. The method of claim 5, wherein the compound and the at least one additional therapeutic agent are co-formulated.

7. The method of claim 5, wherein the compound and the at least one additional therapeutic agent are co-administered.

8. The compound of claim 1 wherein Y is

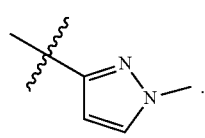 [SMILES: *c1ccn(C)n1]

9. The compound of claim 8 wherein A is

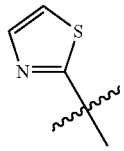

10. The compound of claim 1 wherein Z is $R_1R_2N$—$CH_2$—, wherein $R_1$, $R_2$ and the nitrogen atom to which they are attached form a heterocycloalkyl group which is optionally substituted with one or more groups selected from carboxy; alkoxycarbonyl; halo, azolyl, cyano and R—$SO_2NH$—C(O)—, where R is $C_1$-$C_6$-alkyl.

11. The compound of claim 1 wherein Z is selected from the following groups:

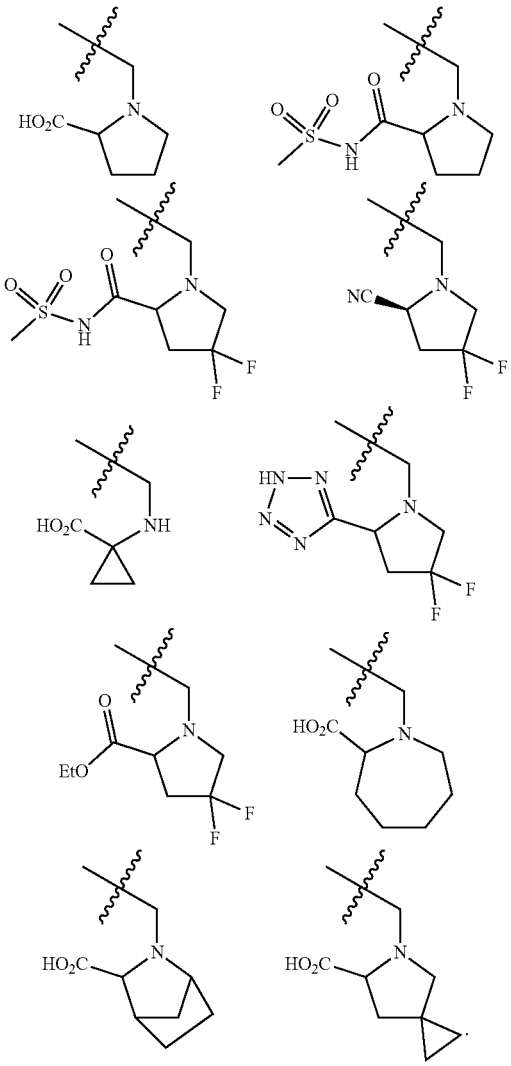

12. The compound of claim 1 wherein X is phenyl substituted with one or more halogen atoms independently selected from fluoro and chloro.

13. The compound of claim 12 wherein X is 2-chloro-4-fluorophenyl.

14. The compound of claim 1 wherein Y is
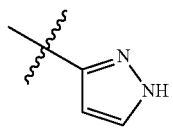 [SMILES: *c1cc[nH]n1]
which is optionally substituted with one or more groups selected from optionally substituted methyl, halo, —CN, —OR$_1$, and —NR$_1$R$_2$, wherein R$_1$ and R$_2$ are as defined in claim 1.
* * * * *